US006576613B1

(12) United States Patent
Brunck et al.

(10) Patent No.: US 6,576,613 B1
(45) Date of Patent: *Jun. 10, 2003

(54) TITLE INHIBITORS OF UROKINASE

(75) Inventors: Terence K. Brunck, San Diego, CA (US); Susan Y. Tamura, San Diego, CA (US); Edwin L. Madison, San Diego, CA (US)

(73) Assignee: Corvas International, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/121,921

(22) Filed: Jul. 24, 1998

(51) Int. Cl.$^7$ .............................................. C07K 5/06
(52) U.S. Cl. ............................ 514/19; 530/331; 514/18
(58) Field of Search ..................... 514/18, 19; 530/331

(56) References Cited

U.S. PATENT DOCUMENTS

| | | | |
|---|---|---|---|
| 5,153,176 A | | 10/1992 | Abe et al. ....................... 514/18 |
| 5,283,293 A | * | 2/1994 | Webb ....................... 525/332.2 |
| 5,508,385 A | | 4/1996 | Abe et al. .................... 530/331 |

FOREIGN PATENT DOCUMENTS

| | | |
|---|---|---|
| WO | WO 94/08941 | 4/1994 |
| WO | 97/47314 | 12/1997 |

OTHER PUBLICATIONS

Bajusz, et al., "Design and Synthesis of Peptide Inhibitors of Blood Coagulation", Folia Hematology, Internationales Magazin Klinische Und Experimentelle Blutforschung. vol. 109, No. 1, Jan. 1, 1982, pp. 16–21.

Ostrowski, et al., "Selective inhibition of proteolytic enzymes in an in vivo mouse model for experimental matastasis", Caner Research, vol. 46, Aug. 1986, pp. 4121–4128.

Patel, et al., "Transistion–state affinity chromatography of trypsin–like proteinases with dipeptidyl argininal ligands", Biochim.Biophys.Acta, vol. 748, 1983, pp. 321–330.

Achbarou et al., "Urokinase overproduction results in increased skeletal metastasis by prostate cancer cells in vivo," Cancer Research 54:2372–2377 (1994).

Alonso et al., "Effects of synthetic urokinase inhibitors on local invasion and metastasis in a murine mammary tumor model," Breast Cancer Research and Treatment 40:209–223 (1996).

Avery et al., "Systemic amiloride inhibits experimentally induced neovascularization," Arch Ophthalmol 108:1474–1476 (1990).

Billstrom et al., "The urokinase inhibitor p–aminobenzamidine inhibits growth of a human prostate tumor in SCID mice," Int. J. Cancer 61:542–547 (1995).

Bindal et al., "Prognostic significance of proteolytic enzymes in human brain tumors," Journal of Neuro–Oncology 22:101–110 (1994).

Bridges et al., "The synthesis of three 4–substituted benzo[b]thiophene–2–carboxamidines as potent and selective inhibitors of urokinase," Bioorganic & Medicinal Chemistry 1(6):403–410 (1993).

Choong et al., "Urokinase–plasminogen–activator levels an prognosis in 69 soft–tissue sarcomas," Int. J. Cancer 69:268–272 (1996).

Crowley et al., "Prevention of metastasis by inhibition of the urokinase receptor," Proc. Natl. Acad. Sci. USA 90:5021–5025 (1993).

Duffy et al., "Urokinase–plasminogen activator, a marker for aggressive breast carcinomas," Cancer 62:531–533 (1988).

Duffy et al., "Urokinase–plasminogen activator, a new and independent prognostic marker in breast cancer," Cancer Research 50:6827–6829 (1990).

Evans et al., "Suppression of pulmonary metastases of rat mammary cancer by recombinant urokinase plasminogen activator inhibitor," American Surgeon 61:692–697 (1995).

Goodson et al., "High–affinity urokinase receptor antagonists identified with bacteriophage peptide display," Proc. Natl. Acad. Sci. USA 91:7129–7133 (1994).

Harvey et al., "Secretion of plasminogen activators by human colorectal and gastric tumor explants," Clin. Expl. Metastasis 6(6):431–450 (1988).

Hasui et al., "The content of urokinase–type plasminogen activator antigen as a prognostic factor in urinary bladder cancer," Int. J. Cancer 50:871–873 (1992).

Hildenbrand et al., "Urokinase and macrophages in tumour angiogenesis," British Journal of Cancer 72:818–823 (1995).

Hofmann et al., "Clinical relevance of urokinase plasminogen activator, its receptor, and its inhibitor in patients with renal cell carcinoma," Cancer 78(3):487–492 (1996).

Jankun et al., "Inhibitors of urokinase reduce size of prostate cancer xenografts in severe combined immunodeficient mice," Cancer Research 57:559–563 (1997).

Kobayashi et al. "Impact of urokinase–type plasminogen activator and its inhibitor type 1 on prognosis in cervical cancer of the uterus," Cancer Research 54:6539–6548 (1994).

Kobayashi et al., "Inhibition of metastasis of lewis lung carcinoma by a synthetic peptide within growth factor–like domain of urokinase in the experimental and spontaneous metastasis model," Int. J. Cancer 57:727–733 (1994).

(List continued on next page.)

Primary Examiner—Christopher S. F. Low
Assistant Examiner—David Lukton
(74) Attorney, Agent, or Firm—Suzanne L. Biggs; Pillsbury Winthrop LLP

(57) ABSTRACT

Novel inhibitors of urokinase are provided which have an arginine or arginine mimic aldehyde or an arginine ketoamide group at P1. These compounds are useful in vitro for monitoring plasminogen activator levels and in vivo in treatment of conditions which are ameliorated by inhibition of or decreased activity of urokinase.

54 Claims, 13 Drawing Sheets

OTHER PUBLICATIONS

Kobayashi et al., "Inhibition of the soluble and the tumor cell receptor–bound plasmin by urinary trypsin inhibitor and subsequent effects on tumor cell invasion and metastasis," *Cancer Research* 54:844–849 (1994).

Kobayashi et al., "Inhibitory effect of a conjugate between human urokinase and urinary trypsin inhibitor on tumor cell invasion in vitro," *Journal of Biological Chemistry* 270(14):8361–8366 (1995).

Kobayashi et al., "Saturation of tumour cell surface receptors for urokinase–type plasminogen activator by amino–terminal fragment and subsequent effect on reconstituted basement membranes invasion," *Br. J. Cancer* 67:537–544 (1993).

Kook et al., "The effect of antisense inhibition of urokinase receptor in human squamos cell carcinoma on malignancy," *EMBO J.* 13(17):3983–3991 (1994).

Kuhn et al., "Urokinase (uPA) and PAI–1 predict survival in advanced ovarian cancer patients (FIGO III) after radical surgery and platinum–based chemotherapy," *Gynecological Oncology* 55:401–409 (1994).

Lu et al., "Blockage of the urokinase receptor on the cell surface: Construction and characterization of a hybrid protein consisting of the N–terminal fragment of human urokinase and human albumin," *FEBS Letters* 356:56–59 (1994).

Lu et al., "Blockage of urokinase receptor reduces in vitro the motility and the deformability of endothelial cells," *FEBS Letters* 380:21–24 (1996).

Min et al., "Urokinase receptor antagonist inhibit angiogenesis and primary tumor growth in syngeneic mice," *Cancer Research* 56:2428–2433 (1996).

Mueller et al., "Overexpression of plasminogen activator inhibitor 2 in human melanoma cells inhibits spontaneous metastasis in scid/scid mice," *Proc. Natl. Acad. Sci. USA* 92:205–209 (1995).

Nekarda et al., "Tumour–associated proteolytic factors uPA and PAI–1 and survival in totally resected gastric cancer," *Lancet* 343:117 (1994).

Oka et al., "immunohistochemical evidence of urokinase–type plasminogen activator in primary and metastatic tumors of pulmonary adenocarcinoma," *Cancer Research* 51:3522–3525 (1991).

Ossowski et al., "Antibodies to plasminogen activator inhibit human tumor metastasis," *Cell* 35:611–619 (1983).

Ossowski et al., "Experimental model for quantitative study of metastasis," *Cancer Research* 40:2300–2309 (1980).

Ossowski, "In vivo invasion of modified chorioallantoic membrane by tumor cells: The role of cell surface–bound urokinase," *Journal of Cell Biology* 107(6):2437–2445 (1988).

Ossowski, "Plasminogen activator dependent pathways in the dissemination of human tumor cells in the chick embryo," *Cell* 52:321–328 (1988).

Paysant et al., "Regulation of the uPAR/uPA system expressed on monocytes by the deactivating cytokines, IL–4, IL–10 and IL–13: Consequences on cell adhesion to vitronectin and fibrinogen," *British Journal of Haematology* 100:45–51 (1998).

Plesner et al., "Structure, function and expression on blood and bone marrow cells of the urokinase–type plasminogen activator receptor, uPAR," *Stem Cells* 5:398–408 (1997).

Quax et al., "Metastatic behavior of human melanoma cell lines in nude mice correlates with urokinase–type plasminogen activator, its type–1 inhibitor, and urokinase–mediated matrix degradation," *Journal of Cell Biology* 115(1):191–199 (1991).

Rabbani et al., "Prevention of prostate–cancer metastasis in vivo by a novel synthetic inhibitor of urokinase–type plasminogen activator (uPA)," *Int. J. Cancer* 63:840–845 (1995).

Shireman et al., "Elevations of tissue–type plasminogen activator and differential expression of urokinase–type plasminogen activator in diseased aorta," *Journal of Vascular Surgery* 25(1):157–164 (1997).

Simon et al., "Mac–1 (CD11b/CD18) and urokinase receptor (CD87) form a functional unit on monocytic cells," *Blood* 88(8):3185–3194 (1996).

Takano et al., "A diaminoanthraquinone inhibitor of angiogenesis," *Journal of Pharmacology and Experimental Therapeutics* 271(2):1027–1033 (1994).

Towle et al., "Inhibition of urokinase by 4–substituted benzo[b]thiophene–2–carboxamidines: An important new class of selective synthetic urokinase inhibitor," *Cancer Research* 53:2553–2559 (1993).

Wilhelm et al., Antisense inhibition of urokinase reduces spread of human ovarian cancer in mice, *Clin. Exp. Metastasis* 13:296–302 (1995).

Xing et al., "Prevention of breast cancer growth, invasion, and metastasis by antiestrogen tamoxifen alone or in combination with urokinase inhibitor B–428," *Cancer Research* 57:3585–3593 (1997).

\* cited by examiner 2-8
(Example 8,
Step 7)

$\xrightarrow{viii}$ 2-9
(Example 8,
Step 8)

TITLE INHIBITORS OF UROKINASE

FIELD OF THE INVENTION

Urokinase is an enzyme involved in the metastasis of tumor cells, neovascularization, and other activities. The purpose of the present invention is to provide novel inhibitors of urokinase that can be used to inhibit the activity of urokinase and thereby attenuate its deleterious effects.

BACKGROUND AND INTRODUCTION TO THE INVENTION

Urinary-type plasminogen activator (uPA; urokinase) is a serine protease within the trypsin/chymotrypsin family. In its physiological state, uPA is found in three forms: single chain pro-uPA, two chain uPA, and low molecular weight uPA (lacks N-terminal domains). The zymogen, pro-uPA, is converted to u-PA by cleavage of the peptide bond at K158-I159. The resultant two chain uPA is linked by disulfide bridges, has an Mr of about 50 kD, and a C-terminal serine proteinase domain.

The activity of uPA is focused to cell surfaces upon binding to its receptor, uPAR. uPAR is a single-chain glycosyl phosphatidyl inositol (GPI)-anchored membrane receptor. The N-terminal 92 amino acids of uPAR play a dominant role in binding to uPA and pro-uPA. Receptor for uPA has been located on T-cells, NK cells, monocytes, and neutrophils, as well as vascular endothelial cells, fibroblasts, smooth muscle cells, keratinocytes, placental trophoblasts, hepatocytes, and a wide variety of tumor cells.

After conversion of pro-uPA to uPA, which occurs primarily at the uPAR on the cell surface, uPA activates plasminogen to plasmin. Activation occurs upon cleavage at residues PGR-VV for human plasminogen, or at residues SGR-IV for bovine plasminogen. Because plasminogen also is present on the cell surface, this activation cascade focuses the activity of u-PA and plasmin on the plasma membrane. Plasmin has many roles, including activation of additional uPA and other enzymes, digestion of fibrin, and digestion of components of the extracellular matrix (ECM). Digestion of the ECM surrounding a tumor removes the ECM as a physical barrier to metastasizing cells, which are then free to leave primary tumors and invade secondary sites. A review of the role of the uPA/uPAR system in cancer metastasis is provided in "The Urokinase-type Plasminogen Activator System in Cancer Metastasis: A Review", Andreasen et al., Int. J. Canc. 72:1–22 (1997).

A correlation between a high level of uPA and a high rate of metastasis, and poor prognosis, has been noted in certain tumors, especially breast cancer [Quax et al., J. Cell Biol. 115:191–199 (1991); Duffy et al., Cancer Res. 50:6827–6829 (1990)]. For instance, tumors of the lung [Oka et al., Cancer Res. 51:3522–3525 (1991)], bladder [Hasui et al., Int. J. Cancer 50:871–873 (1992)], stomach [Nekarda et al., Lancet 343:117 (1994)], cervical cancer [Kobayashi et al., Cancer Res. 54:6539–6548 (1994)], ovary [Kuhn et al., Gynecol. Oncol. 55:401–409 (1994)], kidney [Hofmann et al., Cancer 78:487–492 (1996)], brain [Bindahl et al., J. Neuro-Oncol. 22:101–110 (1994)], and soft tissue sarcoma [Choong et al., Int. J. Cancer (Pred. Oncol.) 69:268–272 (1996)] have exhibited a high level of uPA and/or uPA activity and a high rate of metastases. Overproduction of uPA has been reported to result in increased skeletal metastasis by prostate cancer cells in vivo [Achbarou et al., Cancer Res. 54:2372–2377 (1994)]

Inhibition or lowering of uPA activity, or disruption/inhibition of the interaction between uPA and its receptor (uPAR) has been shown to have a positive effect on maintenance of the extracellular matrix and an inhibitory effect on metastasis [Ossowski and Reich, Cell 35:611–619 (1983); Ossowski, Cell 52:321–328 (1988); Ossowski, J. Cell Biol. 107:2437–2445 (1988); Wilhelm et al., Clin. Exp. Metastasis 13:296–302 (1995); Achbarou et al., Cancer Res. 54:2372–2377 (1994); Crowley et al., Proc. Natl. Acad. Sci. USA 90:5021–5025 (1993); Kook et al., EMBO J. 13:3983–3991 (1994)]. The results of such experimental studies suggest that uPA-catalyzed plasminogen activation is rate-limiting for tumor progression, local tumor invasion and/or formation of distant metastasis. [Andreasen et al., Int. J. Canc. 72:1–22 (1997)].

The effects of the uPA system on cell migration and invasion are thought to be due to both a proteolytic effect of plasmin-mediated degradation of the extracellular matrix, as well as more a direct interaction of the uPA receptor with components of the extracellular matrix. Degradation of the extracellular matrix permits a metastasizing cell to invade the matrix, whereas interaction between uPA receptor and the matrix itself assists a cell in its migration. Localization of the uPA/plasmin system on the cell surface, or the leading edge of metastasizing cells, is consistent with postulated role of uPA in metastasis [Plesner et al., Stem Cells 15:398–408 (1997)].

Interaction of uPAR with vitronectin, a component of the extracellular matrix, mediates cell adhesion and can be enhanced when uPAR is bound by uPA. Cell surface adhesion molecules, integrins, also appear to be involved in this adhesion function, particularly beta-1 and beta-2 integrins [Paysant et al., Br. J. Haematol. 100:45–51 (1998); Simon et al., Blood 88:3185–3194 (1996)]. The CD11b/CD18 integrin can associate with the uPA-uPAR complex and promote adhesion of cells bearing these receptors, e.g., neutrophils, leukocytes.

The uPA/uPAR system also is involved in the establishment of new vasculature, or neovascularization, which is required for sustaining primary and metastatic tumor growth. Pathological neovascularization also is a characteristic of retinal disease, rubeosis iritis, proliferative vitreo retinopathy inflammatory disease, diabetic retinopathy, chronic uveitis, Fuch's heterochromic iridocyclitis, neovascular glaucoma, corneal or optic nerve neovascularization, vascular disease, pterygium, glaucoma surgery bleb failure, hyperkeratosis, cheloid and polyp formation (see EP451, 130). Undesired angiogenesis also can occur in the following conditions or can be a result of the following activities: macular degeneration, retinopathy of prematurity, corneal graft rejection, retrolental fibroplasia, epidemic keratoconjunctivitis, Vitamin A deficiency, contact lens overwear, atopic keratitis, superior limbic keratitis, pterygium keratitis sicca, sogrens disease, acne rosacea, phylectenulosis, syphilis, Mycobacteria infections other than leprosy, lipid degeneration, chemical burns, bacterial or fungal ulcers, Herpes simplex or zoster infections, protozoan infections, Kaposi's sarcoma, Mooren ulcer, Terrien's marginal degeneration, marginal keratolysis, trauma, rheumatoid arthritis, systemic lupus, polyarteritis, Wegeners sarcoidosis, sleritis, Steven's Johnson disease, radial keratotomy, sickle cell anemia, sarcoid, pseudoxanthoma elasticum, Pagets disease, vein or artery occlusion, carotid obstructive disease, chronic uveitis, chronic vitritis, Lyme's disease, Eales disease, Bechets disease, myopia, optic pits, Stargarts disease, pars planitis, chronic retinal detachment, hyperviscosity syndromes, toxoplasmosis, post-laser complications, abnormal proliferation of fibrovascular tissue, hemangiomas, Osler-Wever-Rendu, solid tumors, blood borne tumors, AIDS, ocular neovascular disease, osteoarthritis, chronic inflammation, Crohn's disease, ulceritive colitis, tumors of rhabdomyosarcoma, tumors of retinoblastoma, tumors of Ewing sarcoma, tumors of neuroblastoma, tumors of osteosarcoma, leukemia, psoriasis, atherosclerosis, pemphigoid, as recited An antagonist of uPA/uPAR binding (EGF-like domain of uPA fused to Fc of IgG) was said to inhibit neovascularization and growth of the murine B16 melanoma. [Min et al., Cancer Res. 56:2428–2433 (1996)]. Consistent with this finding is the correlation noted between microvessel density, vascular invasion and uPA levels in breast carcinomas [Hildenbrand et al., Brit. J. Cancer 72:818–823 (1995)]. The known uPA inhibitor amiloride also was said to inhibit a variety of neovascularization pathologies [Glaser et al., EP 451,130; Avery et al., Arch. Ophthalmol. 108:1474–1476 (1990)].

There are two primary physiological inhibitors of uPA, PAI-1 and PAI-2, which are members of the serpin family of proteinase inhibitors. The binding of serpins to their cognate proteases involves a large number of interactions between amino acids of each protein, including those in the serpin reactive loop (S-A-R-M-A (SEQ.ID. NO. 1) for PAI-1, T-G-R-T-G (SEQ.ID. NO. 2) for PAI-2). Introduction of exogenous PAI-2 into experimental animals was reported to inhibit the rate of lung metastasis [Evans and Lin, Amer. Surg. 61:692–697 (1995); Mueller et al., Proc. Natl. Acad. Sci. USA 92:205–209 (1995)]. The ability of PAI-1 to inhibit metastasis has not yet been consistently shown. The gene for PAI-1, and means for its recombinant expression, are disclosed in Loskutoff et al., U.S. Pat. No. 4,952,512. Recombinant and native human PAI-2 is disclosed in Stephens et al., U.S. Pat. No. 5,422,090.

The most widely studied u-PA inhibitors may be within the 4-substituted benzo[b]thiophene-2-carboxamidine class of inhibitors, of which B428 (4-iodo-benzo[b]thiophene-2-carboxamidine) and B623 are members [Towle et al., Cancer Res. 53:2553–2559 (1993); Bridges et al., Bioorg. Med. Chem. 1:403–410 (1993); Bridges et al., U.S. Pat. No. 5,340,833]. Infusion of B-428 in experimental rats inoculated with tumor cells was said to inhibit uPAR gene expression, decrease the primary tumor volume and decrease metastases [Xing et al., Cancer Res. 57:3585–3593 (1997)]. Daily intraperitoneal treatment of mice bearing tumors with B428 or B623 was said to block metastasis to muscle and fat, but did not inhibit tumor-induced angiogenesis or reduce the rate of spontaneous lung metastasis. In fact, B623 enhanced the formation of lung metastasis (Alonso et al., Breast Cancer Res. Treat. 40:209–223 (1996)]. Infusion of B428 in a syngeneic model of rat prostate cancer also lead to a decrease in primary tumor volume and tumor weight, and decrease in metastasis [Rabbani et al., Int. J. Cancer 63:840–845 (1995)].

Other known inhibitors of uPA include p-aminobenzamidine, which is a competitive inhibitor of uPA, and amiloride. Both compounds have been shown to reduce tumor size in experimental animals [Jankan et al., Cancer Res. 57:559–563 (1997); Billstrom et al., Int. J. Cancer 61:542–547 (1995)]. Recently, epigallo-cathecin-3 gallate (EGCG), a polyphenol found in green tea, was reported to bind uPA and inhibit its activity [Jankun et al., Nature 387:561 (1997)]. Those researchers concluded EGCG is a weaker inhibitor of uPA than amiloride, but suggested EGCG can be consumed in much higher doses than amiloride without toxic effect. A competitive inhibitor of uPA, α-N-benzylsulfonyl-p-aminophenylalanine, is disclosed by Pye et al. in U.S. Pat. No. 4,165,258.

Other approaches at inhibiting the uPA/uPAR system include development of a bifunctional hybrid molecule consisting of the uPAR-binding domain of uPA and PAI-2, which is said to inhibit uPA and bind uPAR in vitro [Ballance et al., Eur. J. Biochem. 207:177–183 (1992)]. Antagonists of uPAR also have been studied [Doyle and Rosenberg, U.S. Pat. No. 5,656,726; Min et al., Cancer Res. 56:2428–2433 (1996)], as have antisense oligonucleotides complementary to uPA [Wilhelm et al., Clin. Exp. Metast. 13:296–302 (1995); Iversen and Scholar, U.S. Pat. No. 5,552,390]. Antibodies directed against uPAR, and said to inhibit the binding of uPA to UPAR, are disclosed by Dano et al. in U.S. Pat. No. 5,519,120. Small molecules said to inhibit urokinase, along with a variety of other serine proteases, include those disclosed by Abe et al. in U.S. Pat. Nos. 5,508,385 and 5,153,176, and by Takano et al. in J. Pharmacol. Exp. Therapeut. 271:1027–1033 (1994).

Compounds have been developed to directly inhibit the binding of u-PA to uPAR (Crowley et al., Proc. Natl. Acad. Sci. USA 90:5021–5025 (1993); Goodson et al., Proc. Natl. Acad. Sci. USA 91:7129–7133 (1994); Kobayashi et al., Brit. J. Cancer 67:537–544 (1993), and Int. J. Cancer 57:727–73f3 (1994), and J. Biol. Chem. 270:8361–8366 (1995); Lu et al., FEBS Lett. 356:56–59 (1994) and FEBS Lett. 380:21–24 (1996)].

Additionally, pro-hepatocyte growth factor (HGF), a cell migration stimulating protein, is a substrate of uPA [Naldinie et al., EMBO J. 11:4825–4833 (1992)]. Direct cleavage of a 66 kDa extracellular matrix protein and fibronectin by uPA also has been reported, which suggests a more direct role for uPA in facilitating cell migration [Quigley et al., Proc. Natl. Acad. Sci. 84:2776–2780 (1987)]. Thus, inhibition of uPA may affect these activities, as well.

SUMMARY OF THE INVENTION

The present invention is directed to novel peptide aldehyde and ketoamide compounds. The peptide aldehyde compounds have an arginine or arginine mimic at P1. The ketoamide compounds have an arginine ketoamide group at P1. These compounds are potent inhibitors of urokinase and thereby are useful in decreasing its deleterious effects.

Thus in one aspect, the present invention is directed to compounds of the formula (I):

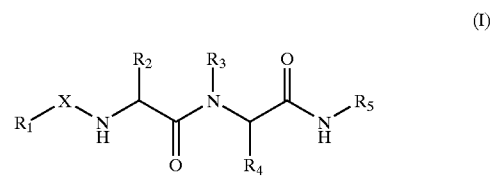

(I)

wherein:
(a) X is selected from the group consisting of —S(O)$_2$—, —N(R')—S(O)$_2$—, —(C=O)—, —OC(=O)—, —NH—C(=O)—, —P(O)(R')—, and a direct link, wherein R' is independently hydrogen, alkyl of 1 to about 4 carbon atoms, aryl of about 6 to about 14 carbon atoms or aralkyl of about 6 to about 16 carbon atoms, with the proviso that when X is —P(O)(R')—, then R' is not hydrogen;
(b) R$_1$ is selected from the group consisting of:
  (1) alkyl of 1 to about 12 carbon atoms which is optionally substituted with Y$_1$,
  (2) alkyl of 1 to about 3 carbon atoms substituted with cycloalkyl of about 5 to about 8 carbon atoms which is optionally mono-, di- or tri-substituted on the ring with $Y_1$, $Y_2$, and/or $Y_3$, (3) cycloalkyl of 3 to about 15 carbon atoms, which is optionally mono-, di-, or tri-substituted on the ring with $Y_1$, $Y_2$, and/or $Y_3$, (4) heterocycloalkyl of 4 to about 10 ring atoms with the ring atoms selected from carbon and heteroatoms, wherein the heteroatoms are selected from the group consisting of oxygen, nitrogen, and $S(O)_i$, wherein i is 0, 1 or 2, which is optionally mono-, di-, or tri-substituted on the ring with $Y_1$, $Y_2$, and/or $Y_3$, (5) heterocyclo of 4 to about 10 ring atoms with the ring atoms selected from carbon and heteroatoms, wherein the heteroatoms are selected from the group consisting of oxygen, nitrogen, and $S(O)_i$, wherein i is 0, 1, or 2, including,

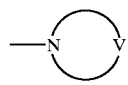

wherein

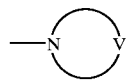

is a 5 to 7 member heterocycle having 3 to 6 ring carbon atoms, where V is —$CH_2$—, —O—, —S(=O)—, —$S(O)_2$— or —S—, which is optionally mono-, di-, or tri-substituted on the ring carbons with with $Y_1$, $Y_2$, and/or $Y_3$, (6) alkenyl of about 2 to about 6 carbon atoms which is optionally substituted with cycloalkyl of about 5 to about 8 carbon atoms, which is optionally mono-, di-, or tri-substituted on the ring with $Y_1$, $Y_2$, and/or $Y_3$, (7) aryl of about 6 to about 14 carbon atoms which is optionally mono-, di- or tri-substituted with $Y_1$, $Y_2$, and/or $Y_3$, (8) heteroaryl of 5 to 14 atoms with the ring atoms selected from carbon and heteroatoms, wherein the heteroatoms are selected from oxygen, nitrogen, and sulfur, and which is optionally mono-, di- or tri-substituted with $Y_1$, $Y_2$, and/or $Y_3$, (9) aralkyl of about 7 to about 15 carbon atoms which is optionally mono-, di-, or tri-substituted on the aryl ring with $Y_1$, $Y_2$, and/or $Y_3$,

(10) heteroaralkyl of 6 to 11 atoms with the ring atoms selected from carbon and heteroatoms, wherein the heteroatoms are selected from oxygen, nitrogen, and sulfur, and which is optionally substituted on the alkyl chain with hydroxy or halogen and optionally mono-, di- or tri-substituted on the ring with $Y_1$, $Y_2$, and/or $Y_3$,

(11) aralkenyl of about 8 to about 15 carbon atoms which is optionally mono-, di-, or tri-substituted on the aryl ring with $Y_1$, $Y_2$, and/or $Y_3$,

(12) heteroaralkenyl of 7 to 12 atoms with the ring atoms selected from carbon and heteroatoms, wherein the heteroatoms are selected from oxygen, nitrogen, and sulfur, and which is optionally mono-, di- or tri-substituted on the ring carbons with $Y_1$, $Y_2$, and/or $Y_3$,

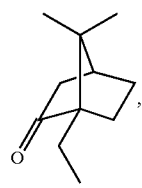

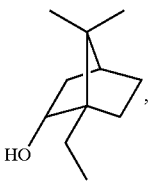

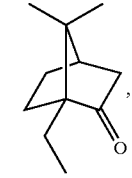

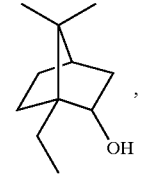

(17) fused carbocyclic alkyl of about 9 to about 15 carbon atoms;

(18) difluoromethyl or perfluoroalkyl of 1 to about 12 carbon atoms,

(19) perfluoroaryl of about 6 to about 14 carbon atoms,

(20) perfluoroaralkyl of about 7 to about 15 carbon atoms, and

(21) hydrogen when X is a direct link; wherein each $Y_1$, $Y_2$, and $Y_3$ is independently selected and is (i) selected from the group consisting of halogen, cyano, nitro, tetrazolyl, guanidino, amidino, methylguanidino, —$CF_3$, —$CF_2CF_3$, $CH(CF_3)_2$, —C(OH) $(CF_3)_2$, —$OCF_3$, —$OCF_2H$, $OCF_2CF_3$, —OC(O) $NH_2$, —OC(O)$NHZ_1$, —OC(O)$NZ_1Z_2$, —NHC(O)$Z_1$, —NHC(O)$NH_2$, —NHC(O)$NZ_1$, —HC(O)$NZ_1Z_2$, —C(O)OH, —C(O)$OZ_1$, —C(O)$NH_2$, —C(O)$NHZ_1$, —C(O)$NZ_1Z_2$, —P(O)$_3H_2$, —P(O)$_3(Z_1)_2$, —$S(O)_3H$, —$S(O)_mZ_1$, —$Z_1$, —$OZ_1$, —OH, —$NH_2$, —$NHZ_1$, —$NZ_1Z_2$, N-morpholino, —$S(CF_2)_qCF_3$, and —$S(O)_m(CF_2)_q CF_3$, wherein m is 0, 1 or 2, q is an integer from 0 to 5, and $Z_1$ and $Z_2$ are independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms, or (ii) $Y_1$ and $Y_2$ are selected together to be —O[C($Z_3$)($Z_4$)]$_r$O—, wherein r is an integer from 1 to 4 and $Z_3$ and $Z_4$ are independently selected from the group consisting of hydrogen, alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms, (c) $R_2$ is selected from the group consisting of H, —$CH_3$, —$C_2H_5$, —$(CH_2)_2OH$, , —$CH(R_6)OH$, and —$CH_2NH$—X'—$R_6$ wherein X' is selected from the group consisting of —$S(O)_2$—, —$S(O)_2$—N(R")—, —(C=O)—, —C(=O)—O—, —C(=O)—NH—, —P(O)(R")—, and a direct link, wherein R" is hydrogen, alkyl of 1 to about 4 carbon atoms, aryl of about 6 to about 14 carbon atoms or aralkyl of about 6 to about 16 carbon atoms with the proviso that when X' is —P(O)(R")—, then R" is not hydrogen, and wherein $R_6$ is selected from from the group consisting of:
(1) alkyl of 1 to about 12 carbon atoms, optionally substituted with $Y_1$,
(2) alkyl of 1 to about 3 carbon atoms substituted with cycloalkyl of about 5 to about 8 carbon atoms, which is optionally mono-, di-, or tri-substituted on the ring with $Y_1$, $Y_2$, and/or $Y_3$,
(3) cycloalkyl of 3 to about 15 carbon atoms, which is optionally mono-, di-, or trisubstituted on the ring with $Y_1$, $Y_2$, and/or $Y_3$,
(4) heterocycloalkyl of 4 to about 10 ring atoms with the ring atoms selected from carbon and heteroatoms, wherein the heteroatoms are selected from the group consisting of oxygen, nitrogen, and $S(O)_i$, wherein i is 0, 1 or 2, which is optionally mono-, di-, or tri-substituted on the ring with $Y_1$, $Y_2$, and/or $Y_3$,
(5) heterocyclo of 4 to about 10 ring atoms with the ring atoms selected from carbon and heteroatoms, wherein the heteroatoms are selected from the group consisting of oxygen, nitrogen, and $S(O)_i$, wherein i is 0, 1, or 2, including

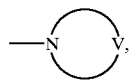

wherein

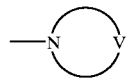

is a 5 to 7 member heterocycle having 3 to 6 ring carbon atoms, where V is —$CH_2$—, —O—, —S(=O)—, —$S(O)_2$— or —S—, which is optionally mono-, di-, or tri-substituted on the ring carbons with with $Y_1$, $Y_2$, and/or $Y_3$,
(6) alkenyl of about 2 to about 6 carbon atoms which is optionally substituted with cycloalkyl of about 5 to about 8 carbon atoms, which is optionally mono-, di-, or tri-substituted on the ring with $Y_1$, $Y_2$, and/or $Y_3$,
(7) aryl of about 6 to about 14 carbon atoms which is optionally mono-, di- or tri-substituted with $Y_1$, $Y_2$, and/or $Y_3$,
(8) heteroaryl of 5 to 14 atoms with the ring atoms selected from carbon and heteroatoms, wherein the heteroatoms are selected from oxygen, nitrogen, and sulfur, and which is optionally mono-, di- or tri-substituted with $Y_1$, $Y_2$, and/or $Y_3$,
(9) aralkyl of about 7 to about 15 carbon atoms which is optionally mono-, di-, or tri-substituted on the aryl ring with $Y_1$, $Y_2$, and/or $Y_3$,
(10) heteroaralkyl of 6 to 11 atoms with the ring atoms selected from carbon and heteroatoms, wherein the heteroatoms are selected from oxygen, nitrogen, and sulfur, and which is optionally substituted on the alkyl chain with hydroxy or halogen and optionally mono-, di- or tri-substituted on the ring with $Y_1$, $Y_2$, and/or $Y_3$,
(11) aralkenyl of about 8 to about 15 carbon atoms which is optionally mono-, di-, or tri-substituted on the aryl ring with $Y_1$, $Y_2$, and/or $Y_3$,
(12) heteroaralkenyl of 7 to 12 atoms with the ring atoms selected from carbon and heteroatoms, wherein the heteroatoms are selected from oxygen, nitrogen, and sulfur, and which is optionally mono-, di- or tri-substituted on the ring carbons with $Y_1$, $Y_2$, and/or $Y_3$, and
(13) hydrogen;

(d) $R_3$ is selected from H or methyl, or $R_3$ and $R_4$ are selected together as set forth in (f), (e) $R_4$ is in the S configuration and is selected from the group consisting of H, —$CH_2$—S—$CH_3$, —$CH_2OH$, —$CH_2CN$, lower alkyl of 1 to about 3 carbon atoms, —$CH_2C\equiv CH$, —$CH_2CH=CH_2$ and —H=$CH_2$ or $R_3$ and $R_4$ are selected together as set forth in (f), (f) $R_3$ and $R_4$ are selected together to be in the S configuration to give a group at P2 selected from the group consisting of prolyl, pipecholyl, azetidine-2-carbonyl, 4-hydroxyprolyl, 3-hydroxyprolyl, and 3,4-dehydroprolyl, (g) $R_5$ is selected from the group consisting of

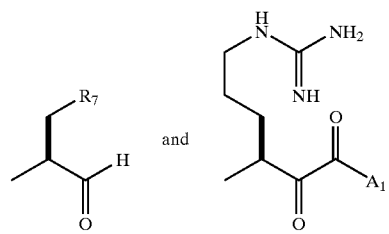

wherein $R_7$ is selected from

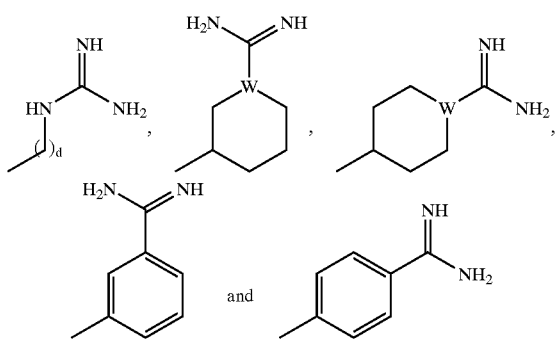

wherein d is an integer from 1 to 3 and W is —N— or —CH—; and (h) $A_1$ is —$NHR_8$, wherein $R_8$ is alkyl of 1 to about 12 carbon atoms, aryl of about 6 to about 14 carbon atoms or aralkyl of about 6 to about 15 carbon atoms, all optionally mono-, di or tri-substituted with $Y_1$, $Y_2$ and/or $Y_3$ or is hydrogen; and pharmaceutically acceptable salts thereof.

The compounds of the present invention can be divided into parts termed $P_1'$, $P_1$, $P_2$, $P_3$ and $P_4$ as shown in the following formulas Ia and Ib:

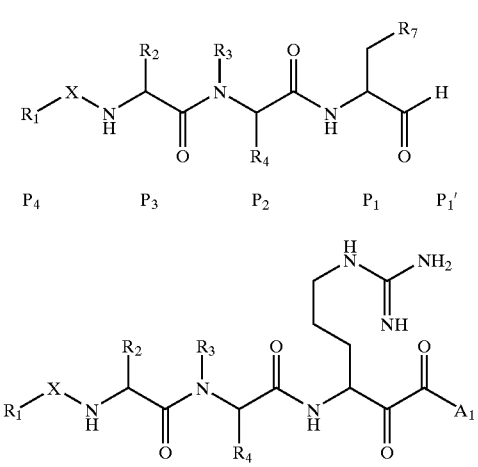

wherein X, $R_1$, $R_2$, $R_3$, $R_4$, $R_7$ and $A_1$ are as defined in connection with formula (I). Thus, the portion of a compound of formula (I) referred to as $P_1$ or P1 is the moiety

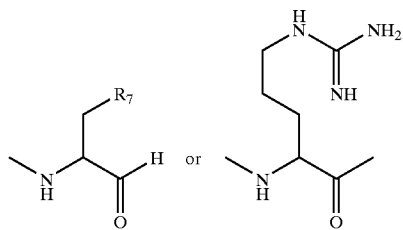

The portion of a compound of formula (I) referred to as $P_2$ or P2 is the moiety

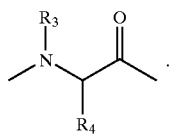

The portion of a compound of formula (I) referred to as $P_3$ or P3 is the moiety

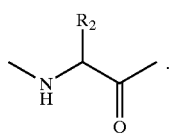

Peptidyl arginine aldehydes have been reported to exist in equilibrium structures in aqueous solutions. Bajusz, S., et al., J. Med. Chem., 33: 1729 (1990). These structures, as shown below, include the arginine aldehyde, A, aldehyde hydrate, B, and two amino cyclol forms, C and D. The R group would represent the remainder of a given compound embodied in the present invention. The peptide aldehydes of the present invention include within their definition all the equilibrium forms.

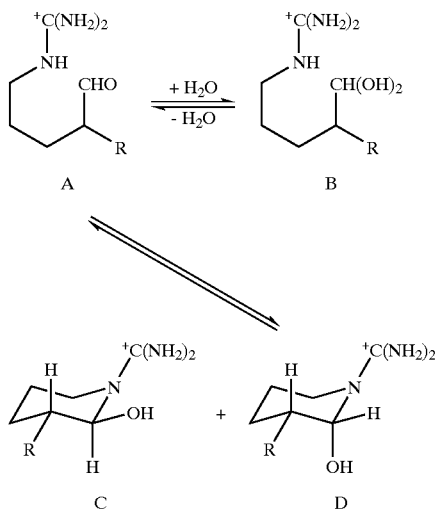

Among other factors, the present invention is based on our finding that the novel compounds of our invention are active as inhibitors of urokinase.

In another aspect, the present invention is directed to pharmaceutical compositions comprising a therapeutically effective amount of a compound of the present invention and a pharmaceutically acceptable carrier.

In yet another aspect, the present invention is directed to methods of using the compounds and pharmaceutical compositions of the present invention for inhibition of urokinase.

DEFINITIONS

In accordance with the present invention and as used herein, the following terms are defined to have following meanings, unless explicitly stated otherwise:

The term "alkenyl" refers to unsaturated aliphatic groups having at least one double bond.

The term "alkyl" refers to saturated aliphatic groups including straight-chain, branched-chain and cyclic (including polycyclic) groups.

The terms "alkoxy" and "alkoxyl" refer to a group having the formula, R—O—, wherein R is an alkyl group.

The term "alkoxycarbonyl" refers to —C(O)OR wherein R is alkyl.

The term "aralkenyl" refers to an alkenyl group substituted with an aryl group.

The term "aralkyl" refers to an alkyl group substituted with an aryl group. Suitable aralkyl groups include benzyl, phehethyl, and the like, all of which may be optionally substituted.

The term "aryl" refers to an aromatic group which has at least one ring having a conjugated pi electron system and includes a carbocyclic aryl, heterocyclic aryl and biarylgroups, all of which may be optionally substituted.

The term "aryloxy" refers to a group having the formula, R—O—, wherein R is an aryl group.

The term "aralkoxy" refers to a group having the formula, R—O—, wherein R is an aralkyl group.

The term "amino acid" refers to both natural, unnatural amino acids in their D and L stereo isomers if their structures allow such stereoisomeric forms, and their analogs. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr) and valine (Val). Unnatural amino acids include, but are not limited to azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4 diaminoisobutyric acid, demosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, N-methylisoleucine, N-methylvaline, norvaline, norleucine, ornithine and pipecolic acid. Amino acid analogs include the natural and unnatural amino acids which are chemically blocked, reversibly or irreversibly, or modified on their N-terminal amino group or their side-chain groups, as for example, methionine sulfoxide, methionine sulfone, S-(carboxymethyl)-cysteine, S-(carboxymethyl)-cysteine sulfoxide and S-(carboxymethyl)-cysteine sulfone.

The term "amino acid analog" refers to an amino acid wherein either the C-terminal carboxy group, the N-terminal amino group or side-chain functional group has been chemically modified to another functional group. For example, aspartic acid-(beta-methyl ester) is an amino acid analog of aspartic acid; N-ethylglycine is an amino acid analog of glycine; or alanine carboxamide is an amino acid analog of alanine.

The term "amino acid residue" refers to radicals having the structure: (1) —C(O)—R—NH—, wherein R typically is —CH(R')—, wherein R' is H or a carbon containing substituent; or (2)

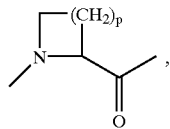

wherein p is 1, 2 or 3 representing the azetidinecarboxylic acid, proline or pipecolic acid residues, respectively.

"Biaryl" refers to phenyl substituted by carbocyclic or heterocyclic aryl as defined herein, ortho, meta or para to the point of attachment of the phenyl ring.

"Brine" refers to an aqueous saturated solution of sodium chloride.

"Carbocyclic aryl" refers to aromatic groups wherein the ring atoms on the aromatic ring are carbon atoms. Carbocyclic aryl groups include monocyclic carbocyclic aryl groups and naphthyl groups, all of which may be optionally substituted. Suitable carbocyclic aryl groups include phenyl and naphthyl. Suitable substituted carbocyclic aryl groups include indene and phenyl substituted by one to two substituents such being advantageously lower alkyl, hydroxy, lower alkoxy, lower alkoxycarbonyl, halogen, trifluoromethyl, difluoromethyl, nitro, and cyano. Substituted naphthyl refers to naphthyl, more preferably 1- or 2-naphthyl, substituted by $Y_1$, $Y_2$ and/or $Y_3$ as defined in connection with formula (I) hereinabove.

"Cycloalkenyl" refers to a cyclic alkenyl group. Suitable cycloalkenyl groups include, for example, cyclopentenyl and cyclohexenyl.

"Cycloalkyl" refers to a cyclic alkyl group having at least one ring and includes polycyclic groups, including fused ring cyclic alkyl groups. Suitable cycloalkyl groups include, for example, cyclohexyl, cyclopropyl, cyclopentyl, and cycloheptyl.

"Cyclohexylmethyl" refers to a cyclohexyl group attached to $CH_2$.

"Fused carbocyclic" refers to a multicyclic fused carbocyclic ring having both aromatic and non-aromatic rings. Suitable fused carbocyclic rings include fluorenyl, tetralin and the like.

"Fused carbocyclic alkyl" refers to an alkyl group substituted with a fused carbocyclic ring moiety, preferably multicyclic fused carbocyclic ring including both aromatic and non-aromatic rings. Suitable fused carbocyclic alkyl groups include fluorenylmethyl, and the like.

The term "halogen" refers to fluorine, chlorine, bromine and iodine.

"Heteroaralkenyl" refers to an alkenyl group substituted with a heteroaryl, and includes those heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems. Preferably the alkenyl group has from 2 to about 6 carbon atoms.

"Heteroaralkyl" refers to an alkyl group substituted with a heteroaryl, such as picolyl, and includes those heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems. Preferably the alkyl group has from 1 to about 6 carbon atoms.

"Heteroaryl" refers to aryl groups having from 1 to 9 carbon atoms and the remainder of the ring atoms are heteroatoms, and includes those heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems. Suitable heteroatoms include oxygen, nitrogen, and $S(O)i$, wherein i is 0, 1 or 2, and suitable heterocyclic aryls include furanyl, thienyl, pyridyl, pyrrolyl, pyrimidyl, pyrazinyl, imidazolyl, and the like.

"Heterocyclo" refers to a reduced heterocyclic ring system comprised of carbon, nitrogen, oxygen and/or sulfur atoms, and includes those heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems.

"Heterocycloalkyl" refers to an alkyl group substituted with a heterocyclo group, and includes those heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems. Preferably the alkyl group has from about 1 to about 6 carbon atoms.

The term "lower" referred to herein in connection with organic radicals or groups defines such radicals or groups with one and up to and including 5 carbon atoms, preferably up to and including 4 carbon atoms, and advantageously one or two carbon atoms. Such radicals or groups may be straight chain or branched chain.

"Perfluoroalkyl" refers to an alkyl group which has every hydrogen replaced with fluorine.

"Perfluoroaryl" refers to an aryl group which has every hydrogen replaced with fluorine.

"Perfluoroarylalkyl" refers to an aralkyl group in which every hydrogen on the aryl moiety is replaced with fluorine.

"Pharmaceutically acceptable salt" includes salts of the compounds of the present invention derived from the combination of such compounds and an organic or inorganic acid. In practice the use of the salt form amounts to use of the base form. The compounds of the present invention are useful in both free base and salt form, with both forms being considered as being within the scope of the present invention.

The term "Arg-al" refers to the residue of L-argininal which has the formula:

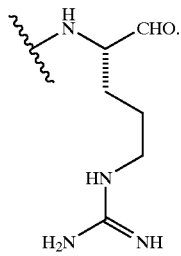

The term "Arg-ol" refers to the residue of L-argininol which has the formula:

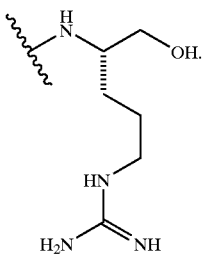

"(S)-N$^g$-nitroarginol hydrochloride" refers to the compound which has the formula:

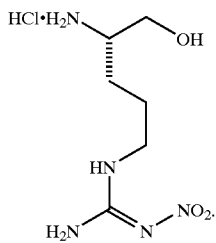

The term "N-α-t-butoxycarbonyl-N$^g$-nitro-L-arginine" refers to the compound which has the formula:

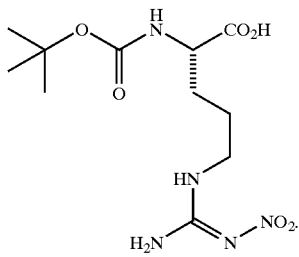

The term "L-N$^g$-nitroarginal ethyl cyclol" refers to a group having the formula:

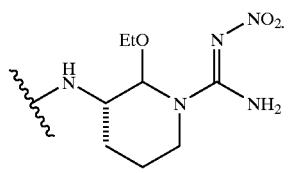

See also U.S. Pat. No. 5,514,777.
"Bn" refers to benzyl.
"Boc" refers to t-butoxycarbonyl.
"BzlSO$_2$" refers to benzylsulfonyl.
"Cbz" or "CBz" refers to benzyloxycarbonyl.
"DCA" refers to dichloroacetic acid.
"DCC" refers to N,N'-dicyclohexylcarbodiimide.
"DCM" refers to dichloromethane.
"DMF" refers to N,N-dimethylformamide.
"DMSO" refers to dimethyl sulfoxide.
"DMAP" refers to 4-N,N-dimethylaminopyridine.
"EDC" refers to 1-ethyl-3-(3-dimethylamino-propyl) carbodiimide hydrochloride salt.
"Et$_3$N" refers to triethylamine.
"EtOH" refers to ethanol.
"HBTU" refers to 2-(1H-benzotriazol-1-yl)-1,1,3,3-tetramethyluronium hexafluorophosphate.
"HCl" refers to hydrochloric acid.
"HOAc" refers to acetic acid
"HPLC" refers to high pressure liquid chromatography.
"HOBt" refers to 1-hydroxybenzotriazole monohydrate.
"i-BuOCOCl" refers to isobutylchloroformate.
"LiAlH$_4$" refers to lithium aluminum hydride.
"LiAlH$_2$(OEt)$_2$" refers to lithium aluminum hydride diethoxide.
"Me" refers to methyl.
"NMM" refers to N-methylmorpholine.
"PhB(OH)$_2$" refers to phenylboronic acid.
"PyBOP" refers to benzotriazole-ly-oxy-tris-pyrrolidino-phosphonium hexafluorophosphate.
"TFA" refers to trifluoroacetic acid.
"THF" refers to tetrahydrofuran.
"TLC" refers to thin layer chromatography.

DETAILED DESCRIPTION OF THE INVENTION

1. Preferred Compounds

Figure 1:
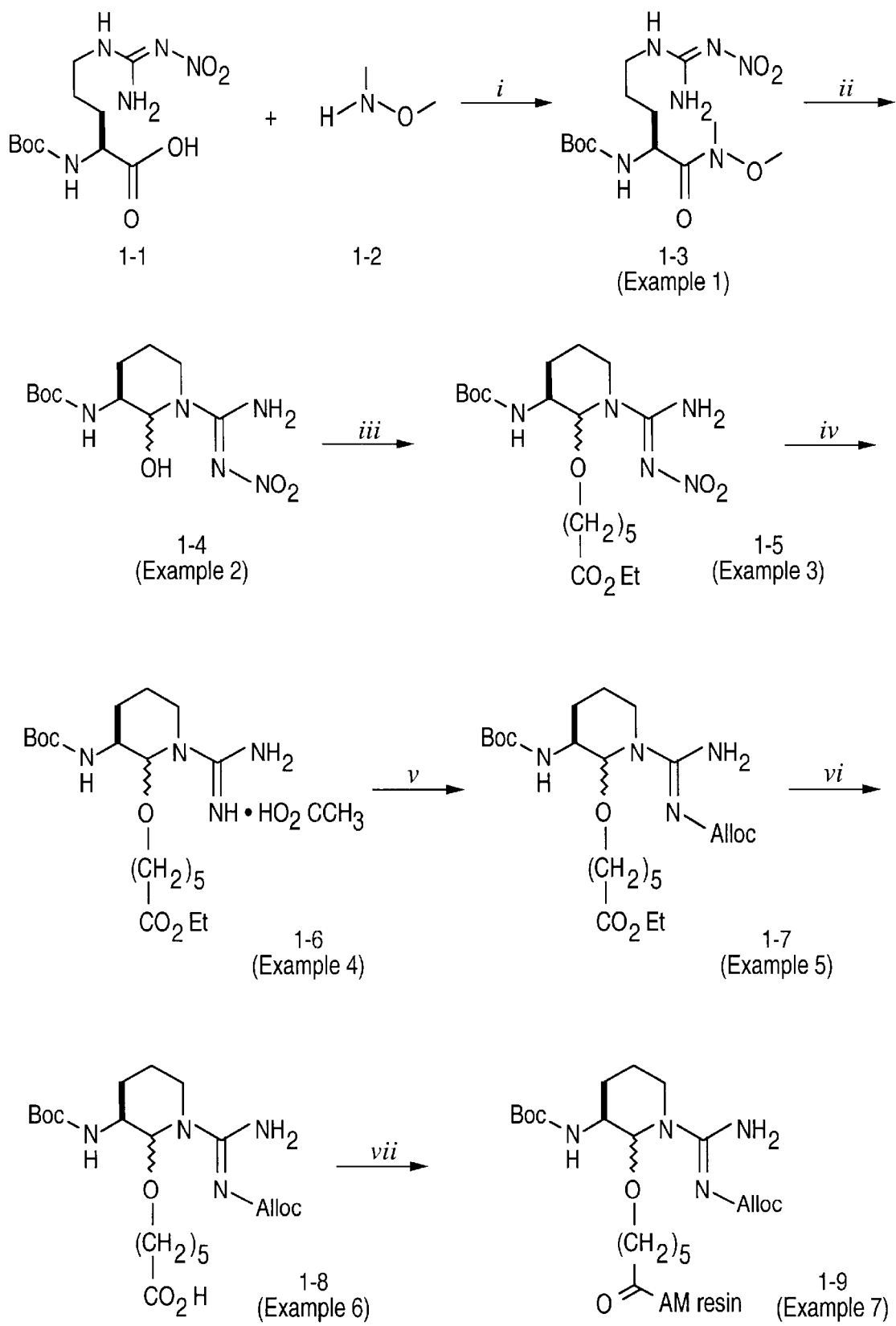
FIG. 1 depicts a reaction scheme for synthesis of an intermediate useful in the solid phase synthesis of compounds of the present invention having an argininal at P1. In this figure, "i" through "vii" are defined as: i) 4-methylmorpholine, EDC, and 1-hydroxybenzotriazole in anhydrous acetonitrile; stirring at room temperature 16 hours, 78% recovery after workup; (ii) lithium aluminum hydride/tetrahydrofuran at −78° C. under N$_2$ one hour; warming to room temperature, cooling to −78° C. and quench with sodium bisulfate, yield 76% after workup; iii) ethyl 6-hydroxyhexanoate in acetonitrile, aqueous HCl; capping excess ethyl 6-hydroxyhexanoate with acetic anhydride and pyridine, 93.7% yield after workup; iv) ethanol/water/acetic acid (4:1:1), 10% palladium on carbon, H$_2$ at 40 psi for 16 hours, 94.4% yield after workup; v) DCM, 1 N NaOH, pH 11–13, allylchloroformate, 80% yield after workup; vi) ethanol, 3N LiOH, 1N HCl to pH 2–3, 83% yield after workup; and vii) amino methylated polystyrene resin ("AM resin"), PyBOP in DMF, diisopropylethylamine, coupling determined by Kaiser test; capping with DMF/acetic acid/triethylamine (8:1:1), 92% yield after workup. See also Examples 1 to 7.

Compounds of the present invention have the formula:

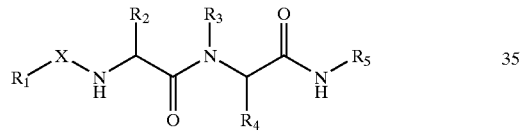

(I)

wherein:
- (a) X is selected from the group consisting of $-S(O)_2-$, $-N(R')-S(O)_2-$, $-(C=O)-$, $-OC(=O)-$, $-NH-C(=O)-$, $-P(O)(R')-$, and a direct link, wherein R' is independently hydrogen, alkyl of 1 to about 4 carbon atoms, aryl of about 6 to about 14 carbon atoms or aralkyl of about 6 to about 16 carbon atoms, with the proviso that when X is $-P(O)(R')-$, then R' is not hydrogen;
- (b) $R_1$ is selected from the group consisting of:
  - (1) alkyl of 1 to about 12 carbon atoms which is optionally substituted with $Y_1$,
  - (2) alkyl of 1 to about 3 carbon atoms substituted with cycloalkyl of about 5 to about 8 carbon atoms which is optionally mono-, di- or tri-substituted on the ring with $Y_1$, $Y_2$, and/or $Y_3$,
  - (3) cycloalkyl of 3 to about 15 carbon atoms, which is optionally mono-, di-, or tri-substituted on the ring with $Y_1$, $Y_2$, and/or $Y_3$,
  - (4) heterocycloalkyl of 4 to about 10 ring atoms with the ring atoms selected from carbon and heteroatoms, wherein the heteroatoms are selected from the group consisting of oxygen, nitrogen, and S(O)i, wherein i is 0, 1 or 2, which is optionally mono-, di-, or tri-substituted on the ring with $Y_1$, $Y_2$, and/or $Y_3$,
  - (5) heterocyclo of 4 to about 10 ring atoms with the ring atoms selected from carbon and heteroatoms, wherein the heteroatoms are selected from the group consisting of oxygen, nitrogen, and $S(O)_i$, wherein i is 0, 1, or 2, including,

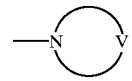

wherein

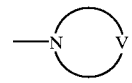

is a 5 to 7 member heterocycle having 3 to 6 ring carbon atoms, where V is $-CH_2-$, $-O-$, $-S(=O)-$, $-S(O)_2-$ or $-S-$, which is optionally mono-, di-, or tri-substituted on the ring carbons with with $Y_1$, $Y_2$, and/or $Y_3$,
  - (6) alkenyl of about 2 to about 6 carbon atoms which is optionally substituted with cycloalkyl of about 5 to about 8 carbon atoms, which is optionally mono-, di-, or tri-substituted on the ring with $Y_1$, $Y_2$, and/or $Y_3$,
  - (7) aryl of about 6 to about 14 carbon atoms which is optionally mono-, di- or tri-substituted with $Y_1$, $Y_2$, and/or $Y_3$,
  - (8) heteroaryl of 5 to 14 atoms with the ring atoms selected from carbon and heteroatoms, wherein the heteroatoms are selected from oxygen, nitrogen, and sulfur, and which is optionally mono-, di- or tri-substituted with $Y_1$, $Y_2$, and/or $Y_3$,
  - (9) aralkyl of about 7 to about 15 carbon atoms which is optionally mono-, di-, or tri-substituted on the aryl ring with $Y_1$, $Y_2$, and/or $Y_3$,
  - (10) heteroaralkyl of 6 to 11 atoms with the ring atoms selected from carbon and heteroatoms, wherein the heteroatoms are selected from oxygen, nitrogen, and sulfur, and which is optionally substituted on the alkyl chain with hydroxy or halogen and optionally mono-, di- or tri-substituted on the ring with $Y_1$, $Y_2$, and/or $Y_3$,
  - (11) aralkenyl of about 8 to about 15 carbon atoms which is optionally mono-, di-, or tri-substituted on the aryl ring with $Y_1$, $Y_2$, and/or $Y_3$,
  - (12) heteroaralkenyl of 7 to 12 atoms with the ring atoms selected from carbon and heteroatoms, wherein the heteroatoms are selected from oxygen, nitrogen, and sulfur, and which is optionally mono-, di- or tri-substituted on the ring carbons with $Y_1$, $Y_2$, and/or $Y_3$,

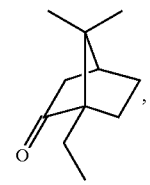

(13)

-continued

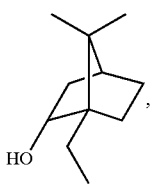
(14)

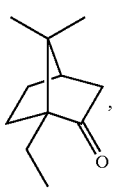
(15)

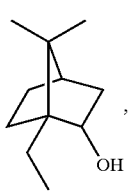
(16)

(17) fused carbocyclic alkyl of about 9 to about 15 carbon atoms;
(18) difluoromethyl or perfluoroalkyl of 1 to about 12 carbon atoms,
(19) perfluoroaryl of about 6 to about 14 carbon atoms,
(20) perfluoroaralkyl of about 7 to about 15 carbon atoms, and
(21) hydrogen when X is a direct link; wherein each $Y_1$, $Y_2$, and $Y_3$ is independently selected and is
  (i) selected from the group consisting of halogen, cyano, nitro, tetrazolyl, guanidino, amidino, methylguanidino, —$CF_3$, —$CF_2CF_3$, $CH(CF_3)_2$, —$C(OH)(CF_3)_2$, —$OCF_3$, —$OCF_2H$, $OCF_2CF_3$, —$OC(O)NH_2$, —$OC(O)NHZ_1$, —$OC(O)NZ_1Z_2$, —$NHC(O)Z_1$, —$NHC(O)NH_2$, —$NHC(O)NZ_1$, —$NHC(O)NZ_1Z_2$, —$C(O)OH$, —$C(O)OZ_1$, —$C(O)NH_2$, —$C(O)NHZ_1$, —$C(O)NZ_1Z_2$, —$P(O)_3H_2$, —$P(O)_3(Z_1)_2$, —$S(O)_3H$, —$S(O)_mZ_1$, —$Z_1$, —$OZ_1$, —$OH$, —$NH_2$, —$NHZ_1$, —$NZ_1Z_2$, N-morpholino, —$S(CF_2)_qCF_3$, and —$S(O)_m(CF_2)_qCF_3$, wherein m is 0, 1 or 2, q is an integer from 0 to 5, and $Z_1$ and $Z_2$ are independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms, or
  (ii) $Y_1$ and $Y_2$ are selected together to be —$O[C(Z_3)(Z_4)]_rO$—, wherein r is an integer from 1 to 4 and $Z_3$ and $Z_4$ are independently selected from the group consisting of hydrogen, alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms,
(c) $R_2$ is selected from the group consisting of H, —$CH_3$, —$C_2H_5$, —$(CH_2)_2OH$, —$CH(R_6)OH$, and —$CH_2NH$—X'—$R_6$ wherein X' is selected from the group consisting of —$S(O)_2$—, —$S(O)_2$—N(R")—, —(C=O)—, —C(=O)—O—, —C(=O)—NH—, —P(O)(R")—, and a direct link, wherein R" is hydrogen, alkyl of 1 to about 4 carbon atoms, aryl of about 6 to about 14 carbon atoms or aralkyl of about 6 to about 16 carbon atoms with the proviso that when X' is —P(O)(R")—, then R" is not hydrogen, and wherein $R_6$ is selected from from the group consisting of:
(1) alkyl of 1 to about 12 carbon atoms, optionally substituted with $Y_1$,
(2) alkyl of 1 to about 3 carbon atoms substituted with cycloalkyl of about 5 to about 8 carbon atoms, which is optionally mono-, di-, or tri-substituted on the ring with $Y_1$, $Y_2$, and/or $Y_3$,
(3) cycloalkyl of 3 to about 15 carbon atoms, which is optionally mono-, di-, or trisubstituted on the ring with $Y_1$, $Y_2$, and/or $Y_3$,
(4) heterocycloalkyl of 4 to about 10 ring atoms with the ring atoms selected from carbon and heteroatoms, wherein the heteroatoms are selected from the group consisting of oxygen, nitrogen, and $S(O)_i$, wherein i is 0, 1 or 2, which is optionally mono-, di-, or tri-substituted on the ring with $Y_1$, $Y_2$, and/or $Y_3$,
(5) heterocyclo of 4 to about 10 ring atoms with the ring atoms selected from carbon and heteroatoms, wherein the heteroatoms are selected from the group consisting of oxygen, nitrogen, and $S(O)_i$, wherein i is 0, 1, or 2, including

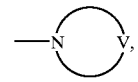

wherein

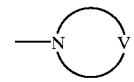

is a 5 to 7 member heterocycle having 3 to 6 ring carbon atoms, where V is —$CH_2$—, —O—, —S(=O)—, —$S(O)_2$— or —S—, which is optionally mono-, di-, or tri-substituted on the ring carbons with with $Y_1$, $Y_2$, and/or $Y_3$,
(6) alkenyl of about 2 to about 6 carbon atoms which is optionally substituted with cycloalkyl of about 5 to about 8 carbon atoms, which is optionally mono-, di-, or tri-substituted on the ring with $Y_1$, $Y_2$, and/or $Y_3$,
(7) aryl of about 6 to about 14 carbon atoms which is optionally mono-, di- or tri-substituted with $Y_1$, $Y_2$, and/or $Y_3$,
(8) heteroaryl of 5 to 14 atoms with the ring atoms selected from carbon and heteroatoms, wherein the heteroatoms are selected from oxygen, nitrogen, and sulfur, and which is optionally mono-, di- or tri-substituted with $Y_1$, $Y_2$, and/or $Y_3$,
(9) aralkyl of about 7 to about 15 carbon atoms which is optionally mono-, di-, or tri-substituted on the aryl ring with $Y_1$, $Y_2$, and/or $Y_3$,
(10) heteroaralkyl of 6 to 11 atoms with the ring atoms selected from carbon and heteroatoms, wherein the heteroatoms are selected from oxygen, nitrogen, and sulfur, and which is optionally substituted on the alkyl chain with hydroxy or halogen and optionally mono-, di- or tri-substituted on the ring with $Y_1$, $Y_2$, and/or $Y_3$,

(11) aralkenyl of about 8 to about 15 carbon atoms which is optionally mono-, di-, or tri-substituted on the aryl ring with $Y_1$, $Y_2$, and/or $Y_3$,

(12) heteroaralkenyl of 7 to 12 atoms with the ring atoms selected from carbon and heteroatoms, wherein the heteroatoms are selected from oxygen, nitrogen, and sulfur, and which is optionally mono-, di- or tri-substituted on the ring carbons with $Y_1$, $Y_2$, and/or $Y_3$, and

(13) hydrogen;

(d) $R_3$ is selected from H or methyl, or $R_3$ and $R_4$ are selected together as set forth in (f), (e) $R_4$ is in the S configuration and is selected from the group consisting of H, —$CH_2$—S—$CH_3$, —$CH_2OH$, —$CH_2CN$, lower alkyl of 1 to about 3 carbon atoms, —$CH_2C\equiv CH$, —$CH_2CH=CH_2$ and —$CH=CH_2$ or $R_3$ and $R_4$ are selected together as set forth in (f), (f) $R_3$ and $R_4$ are selected together to be in the S configuration to give a group at P2 selected from the group consisting of prolyl, pipecholyl, azetidine-2-carbonyl, 4-hydroxyprolyl, 3-hydroxyprolyl, and 3,4-dehydroprolyl, (g) $R_5$ is selected from the group consisting of

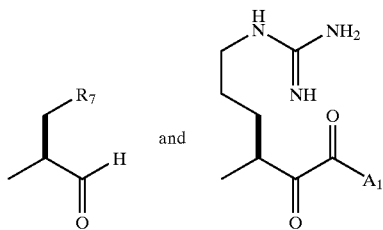

wherein $R_7$ is selected from

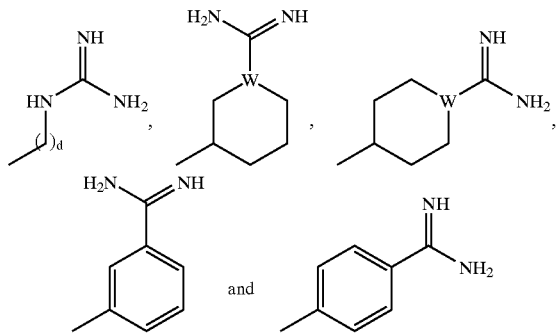

wherein d is an integer from 1 to 3 and W is —N— or —CH—; and (h) $A_1$ is —$NHR_8$, wherein $R_8$ is alkyl of 1 to about 12 carbon atoms, aryl of about 6 to about 14 carbon atoms or aralkyl of about 6 to about 15 carbon atoms, all optionally mono-, di or tri-substituted with $Y_1$, $Y_2$ and/or $Y_3$ or is hydrogen; and pharmaceutically acceptable salts thereof.

Preferred X groups include —$S(O)_2$—, —$OC(=O)$—, —NH—$C(=O)$—, and a direct link. Especially preferred are —$S(O)_2$— and —$OC(=O)$—.

Preferred $R_1$ groups include alkyls, especially isobutyl, 2-ethylhexyl, methyl, butyl, isopropyl, cyclohexylmethyl, and cyclohexylpropyl; cycloalkyl, especially (−)menthyl, (+)menthyl, and cyclohexyl; aryls, especially naphthyl and phenyl; aralkyls, especially benzyl, 3-phenylpropyl, and 2-phenylethyl; and fused carbocyclic alkyls, especially fluorenylmethyl. Especially preferred $R_1$ groups include phenyl, benzyl, 2-phenylethyl, isobutyl, and 3-phenylpropyl.

Preferred combinations of $R_1$—X— include phenyl—$S(O)_2$—, benzyl—$S(O)_2$—, 2-phenylethyl—$S(O)_2$—, 3-phenylpropyl—$S(O)_2$—, benzyl—$OC(=O)$—, and isobutyl—$OC(=O)$—.

Preferred $R_2$ groups include H, —$CH_3$, —$C_2H_5$, —$CH_2NH(X')(R_6)$ and —$CH(R_6)OH$, wherein $R_6$ is hydrogen, alkyl, especially methyl, or aralkyl. Preferred chirality at the alpha carbon is R. When chiral, preferred chirality at the beta carbon is R. Preferred $R_2$ groups are those that define the $P_3$ position as glycine, d-seryl ($R_6$ is H), (R,R)d-allothreonyl ($R_6$ is methyl), d-2-aminobutyryl, N-β-methyloxycarbonyl-d-2,3-diaminopropionyl ($CH_2NH(X')$ $R_6$ where $R_6$ is $CH_3$ and X' is (C=O)O—), N-β-(2-phenylethylcarbonyl)-d-2,3-diaminopropionyl ($CH_2NH(X)$ $R_6$ where $R_6$ is 2-phenylethyl and X' is (C=O)), and N-β-benzyloxycarbonyl-d-2,3-diaminopropionyl ($CH_2NH$ $(X')R_6$ where $R_6$ is benzyl and X is (C=O)O). Especially preferred $R_2$ groups are those which define $P_3$ as d-seryl ($R_6$ is H) or (R,R) d-allothreonyl ($R_6$ is methyl).

A preferred $R_3$ group, when $R_3$ and $R_4$ are not selected together, is hydrogen. A preferred $R_4$ group, when $R_3$ and $R_4$ are not selected together, is methyl or propargyl. When $R_3$ and $R_4$ are selected together, prolyl, 4-cis-hydroxyprolyl, 3,4-dehydroprolyl, and azetidine-2-carbonyl- are preferred selections to define a group at P2.

The preferred $R_5$ group is arginine aldehyde.

Among the claimed compounds, those having an $R_2$ element that defines d-serine or d-allothreonine at that position of the compound and an arginine aldehyde at $R_5$ are preferred. Especially preferred are such compounds also having either i) a hydrogen at $R_3$ and methyl at $R_4$ (P2 is alanine), or ii) having $R_3$ and $R_4$ selected together so that P2 is prolyl, azetidine-2-carbonyl, or 3,4-dehydroprolyl.

Preferred compounds of the present invention include:

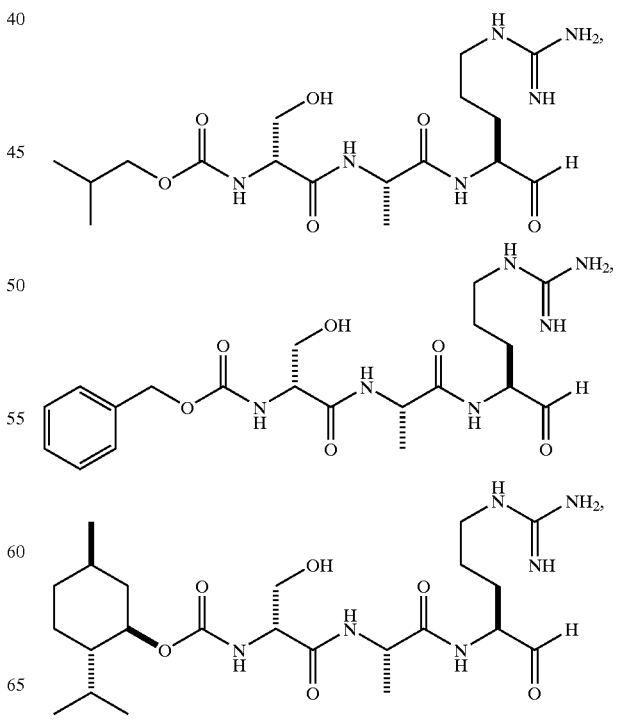

-continued

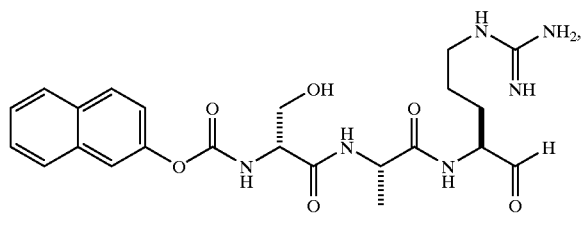

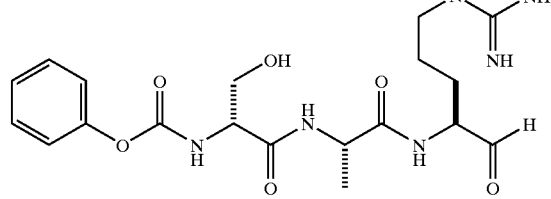

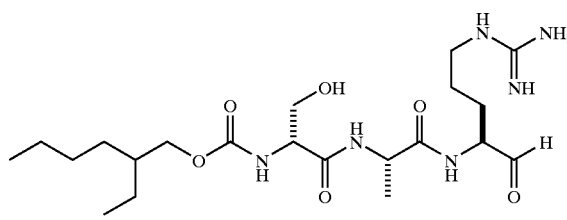

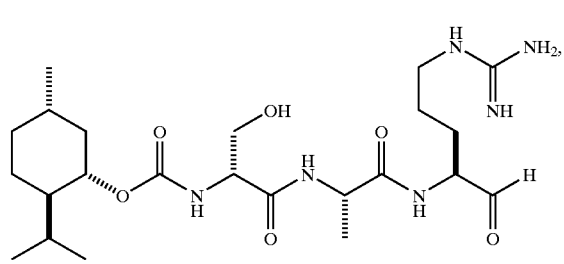

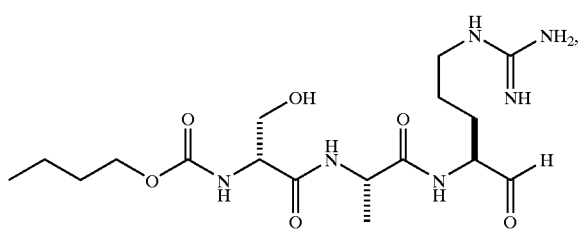

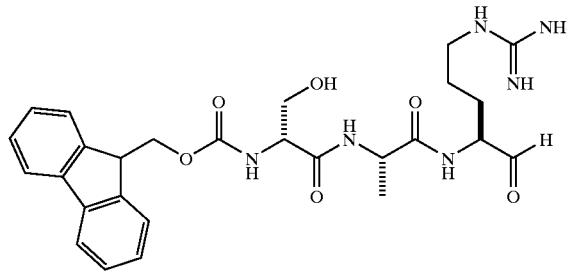

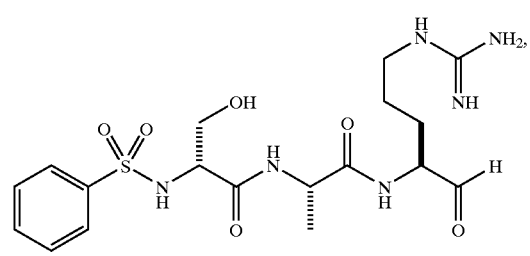

-continued

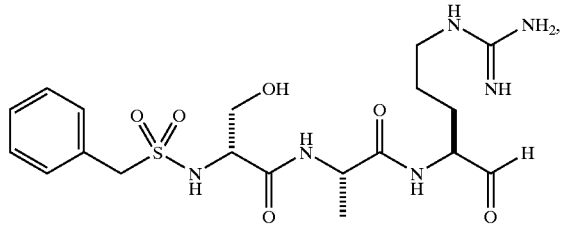

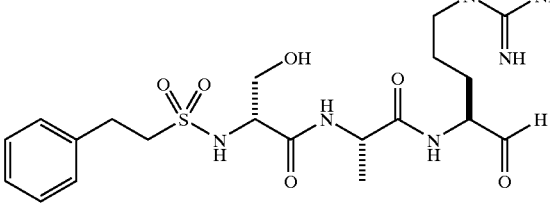

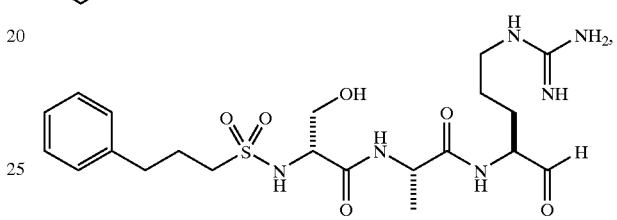

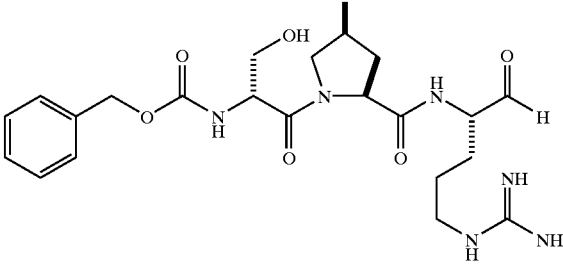

and

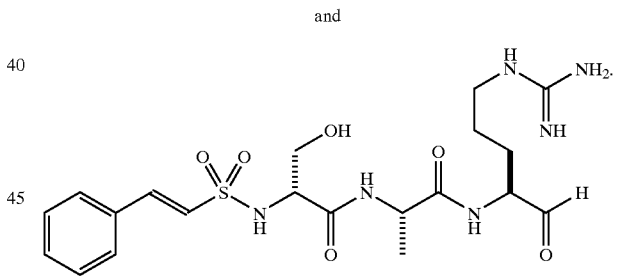

2. Preparation of Preferred Compounds

FIGS. 1 to 12 depict synthetic schemes for preparation of certain preferred compounds of the present invention.

FIG. 1 depicts synthesis of N-α-t-E-butoxycarbonyl-N-omega-allyloxycarbonyl-argininal (6-hexanoyl-amino-methylated polysyrene resin) cyclol which is useful in solid phase synthesis of compounds of the present invention having an arginine aldehyde at P1. This synthesis is described in detail by Examples 1 to 7.

Figure 2A:
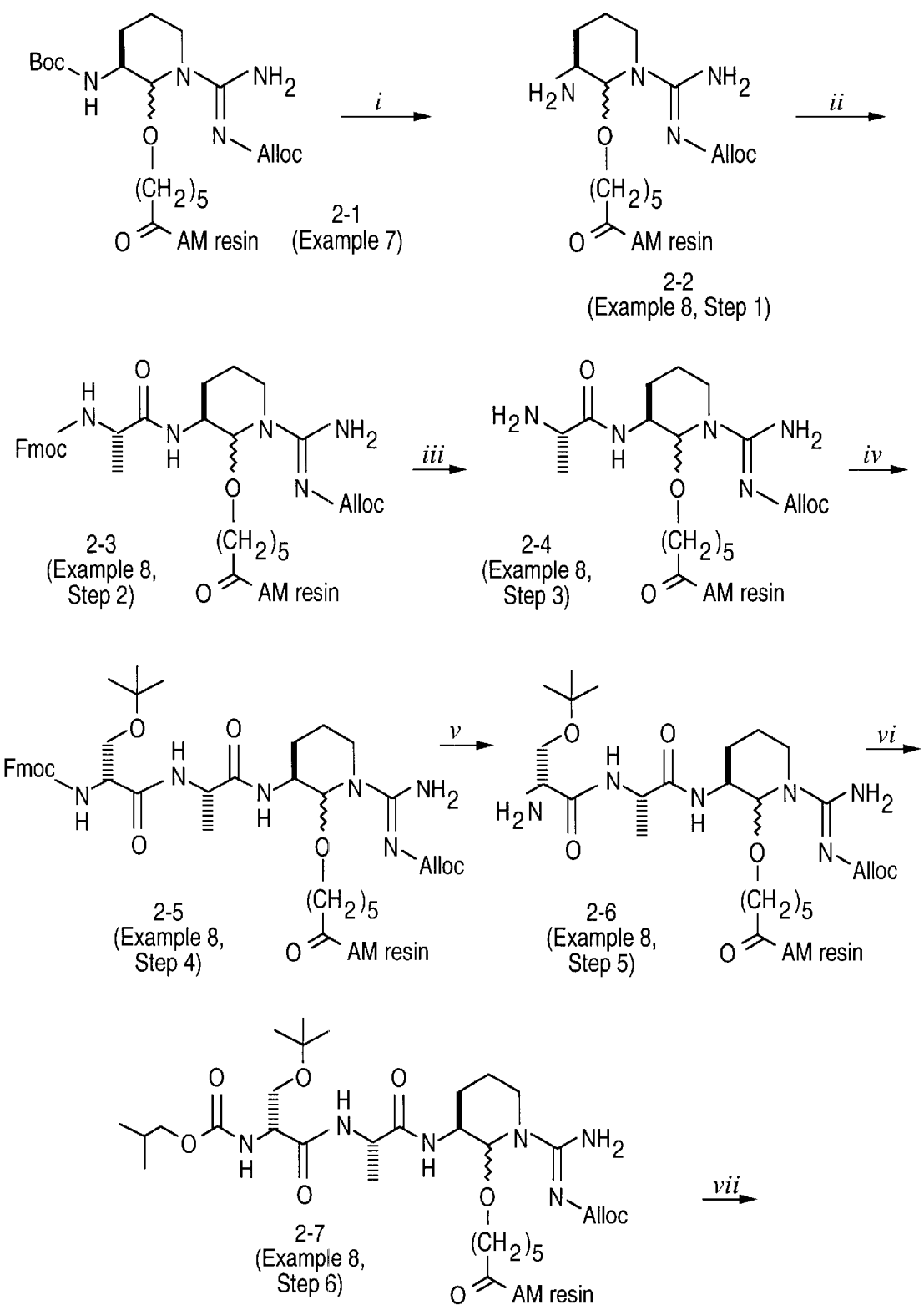
FIG. 2 depicts a reaction scheme for the solid phase synthesis of a compound of the present invention using resin 1–9 (See FIG. 1). In this figure, "i" through "viii" are defined as i) DCM, TFA, and thioanisole; ii) Fmoc-alanine, 1-hydroxybenzotriazole, TBTU, and diisopropylethylamine in DMF, 99.5% coupling efficiency; iii) 50% piperidine in DMF; iv) DMF, N-α-Fmoc-D-serine (O-t-butyl), 1-hydroxybenzotriazole, TBTU, diisopropylethylamine; v) 50% piperidine in DMF; vi) isobutylchloroformate in DMF, diisopropylethylamine; vii) methylsulfoxide, tetrahydrofuran, 1 N HCl, morpholine, tetrakis triphenylphosphine palladium; and viii) TFA/DCM/H$_2$O (6:3:1), purification by semi-preparative reverse phase HPLC. See also Example 8.
Figure 2B:
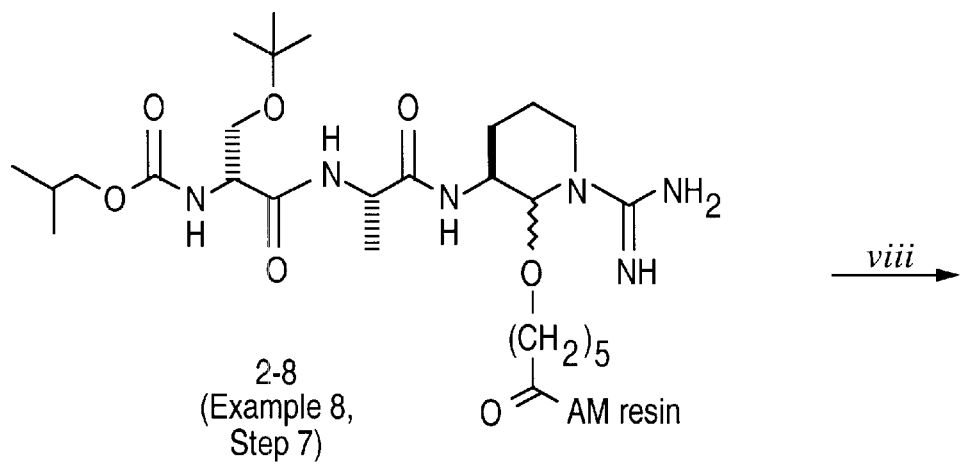
Figure 2B:
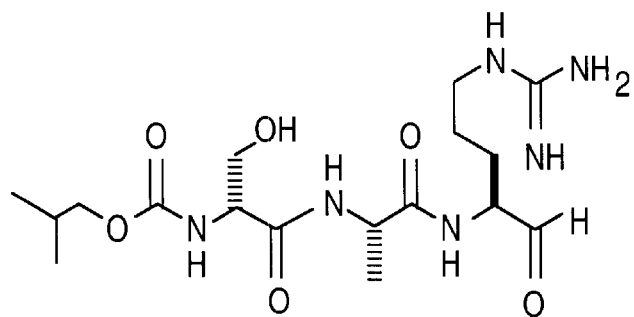
Figure 7:
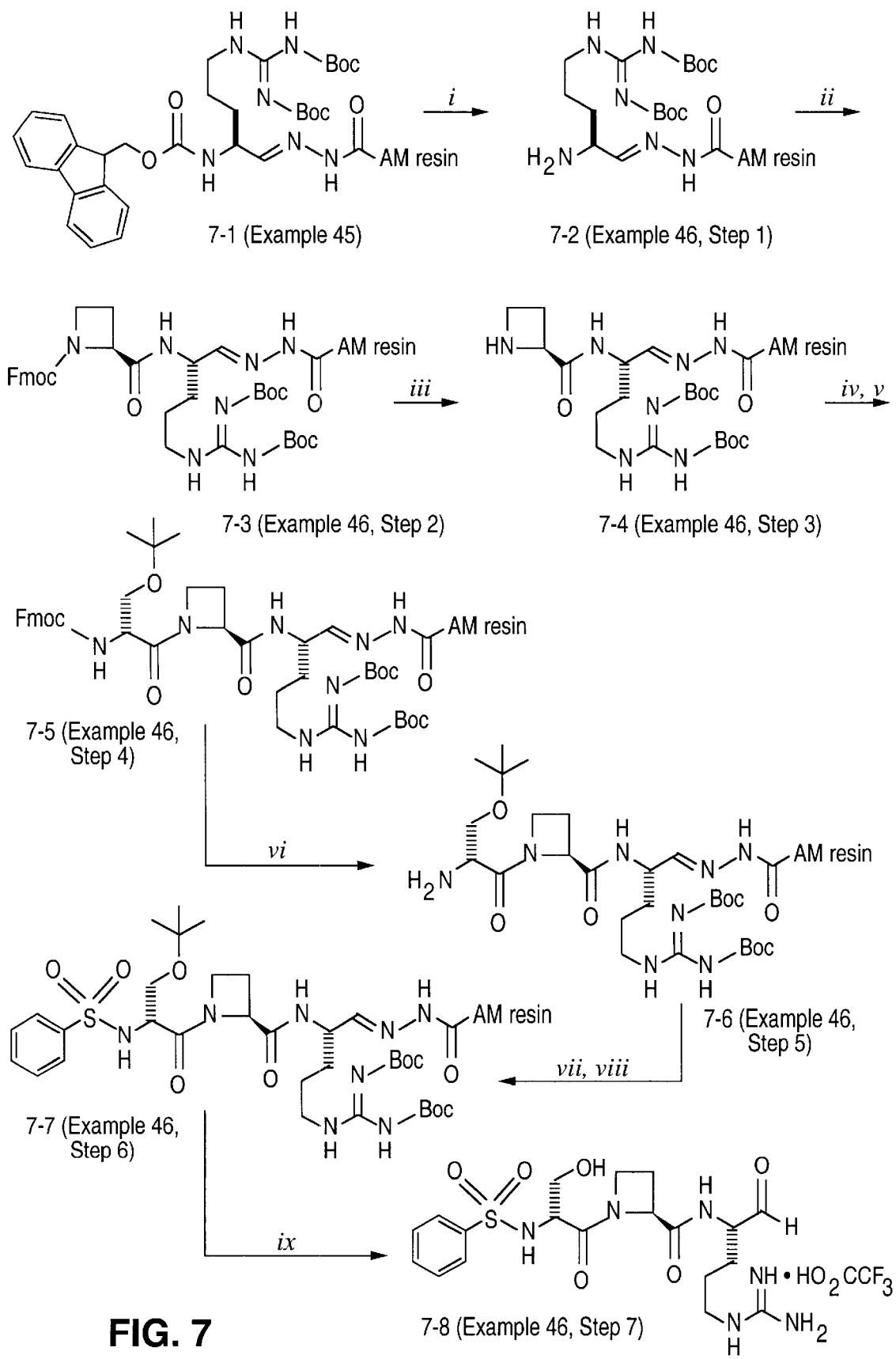
FIG. 7 depicts a reaction scheme for solid phase synthesis of compounds of the present invention having an argininal at P1 and using the intermediate of FIG. 6. In this figure, "i" through "ix" are defined as: i) 30% piperidine/DMF; ii) N-α-Fmoc-azetidine-2-carboxylic acid, 1-hydroxybenzotriazole, TBTU, and diisopropylethylamine in DMF; iii) 30% piperidine/DMF; iv) N-α-Fmoc-D-serine-t-butyl ether, 1-hydroxybenzotriazole, TBTU, and diisopropylethylamine in DMF; v) double coupling: N-α-Fmoc-serine-o-t-butyl ether, 1-hydroxybenzotriazole, TBTU and diisopropylethylamine in DMF, 97% coupling efficiency after work up; vi) 30% piperidine/DMF; vii) benzenesulfonyl chloride and diisopropylethylamine in DMF; viii) double coupling: benzenesulfonyl chloride and diisopropylethylamine in DMF, 96% coupling efficiency after workup; and ix) TFA/water (9:1), 26% yield after purification by semipreparative reverse phase HPLC. See also Examples 46 to 53.

FIG. 2 depicts solid phase synthesis of a compound of the present invention using the resin depicted in FIG. 7. This synthesis is described further in Example 8.

Figure 3:
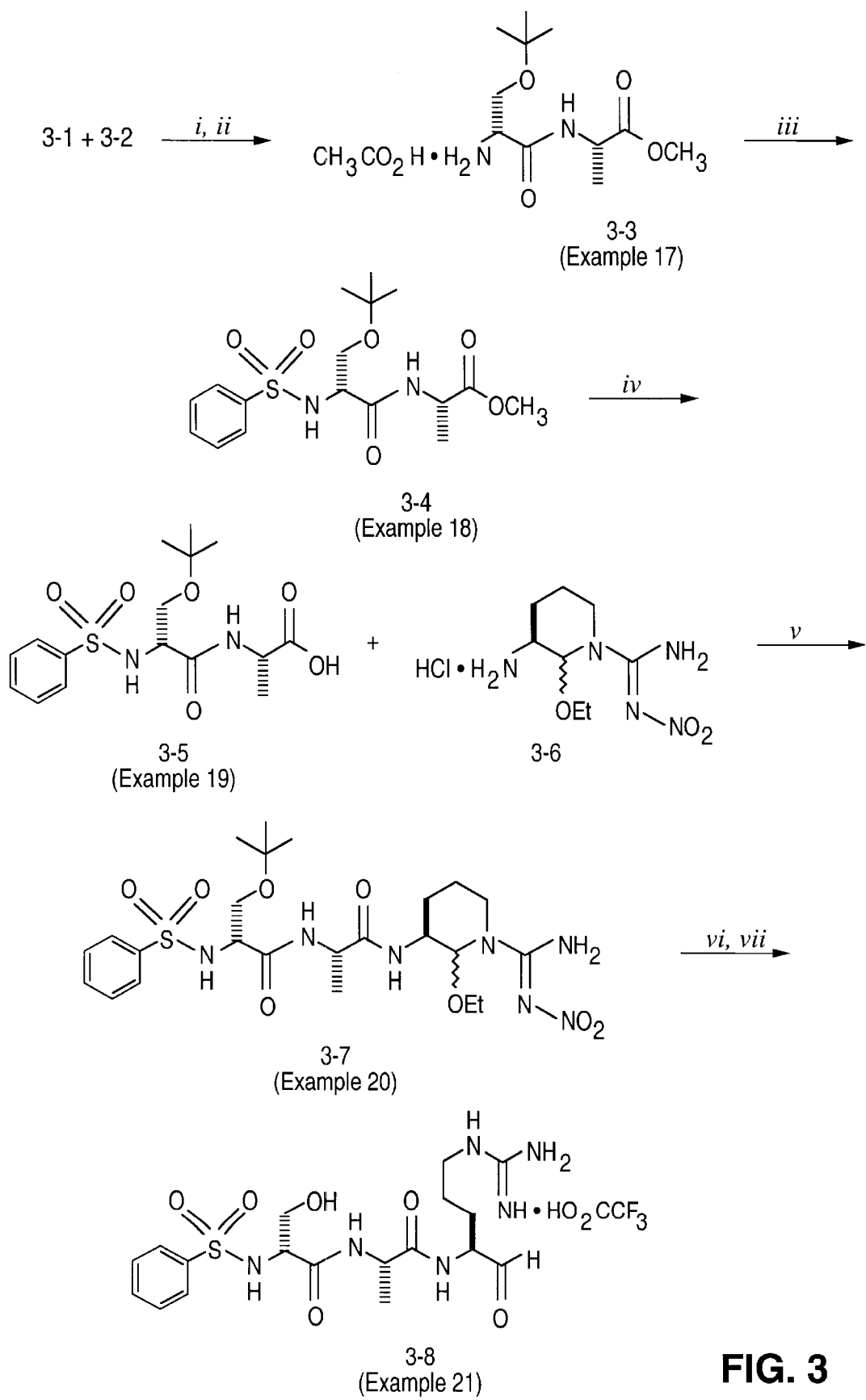
FIG. 3 depicts a reaction scheme for solution phase synthesis of a compound of the present reaction having an argininal at P1 using a L-N$^g$-nitroargininal ethyl cyclol intermediate. Compound 3-1 is N-α-Cbz-D-serine (O-t-butyl), compound 3-2 is alanine methyl ester, hydrochloride salt. In this figure, "i" through "vii" are defined as i) EDC, 1-hydroxybenzotriazole and acetonitrile, diisopropylethylamine to give Cbz-D-Ser (O-t-butyl)-Ala-OMe; (ii) ethanol/acetic acid/water (4:1:1), 10% Pd on carbon, 45 psi H$_2$ for 2 hours, 95% yield after work-up; iii) acetonitrile, benzenesulfonyl chloride, diisopropylethylamine, 43% yield after work-up; iv) methanol, 1.0 M lithium hydroxide, acidification on DOWEX ion exchange resin, eluting with methanol/water, 95% yield after work-up; v) 1-hydroxybenzotriazole, acetonitrile, diisopropylethylamine, 95% yield after work-up; vi) hydrogenation over 10% Pd on carbon in ethanol/acetic acid/water (4:1:1) at 50 psi, isolation of benzylsufonyl-D-Ser(O-t-Bu)-L-Ala-L-argininal ethyl cyclol; and vii) 6 M HCl with stirring, 6.5M ammonium acetate to pH 4, purification by preparative reverse-phase HPLC, 15% yield for three (v-vii) steps. See also Examples 17 to 20.

FIG. 3 depicts solution phase synthesis of compounds of the present invention using a L-N$^g$-nitroargininal ethyl cyclol intermediate. See also Examples 17 to 21 and 22 to 26.

Figure 4:
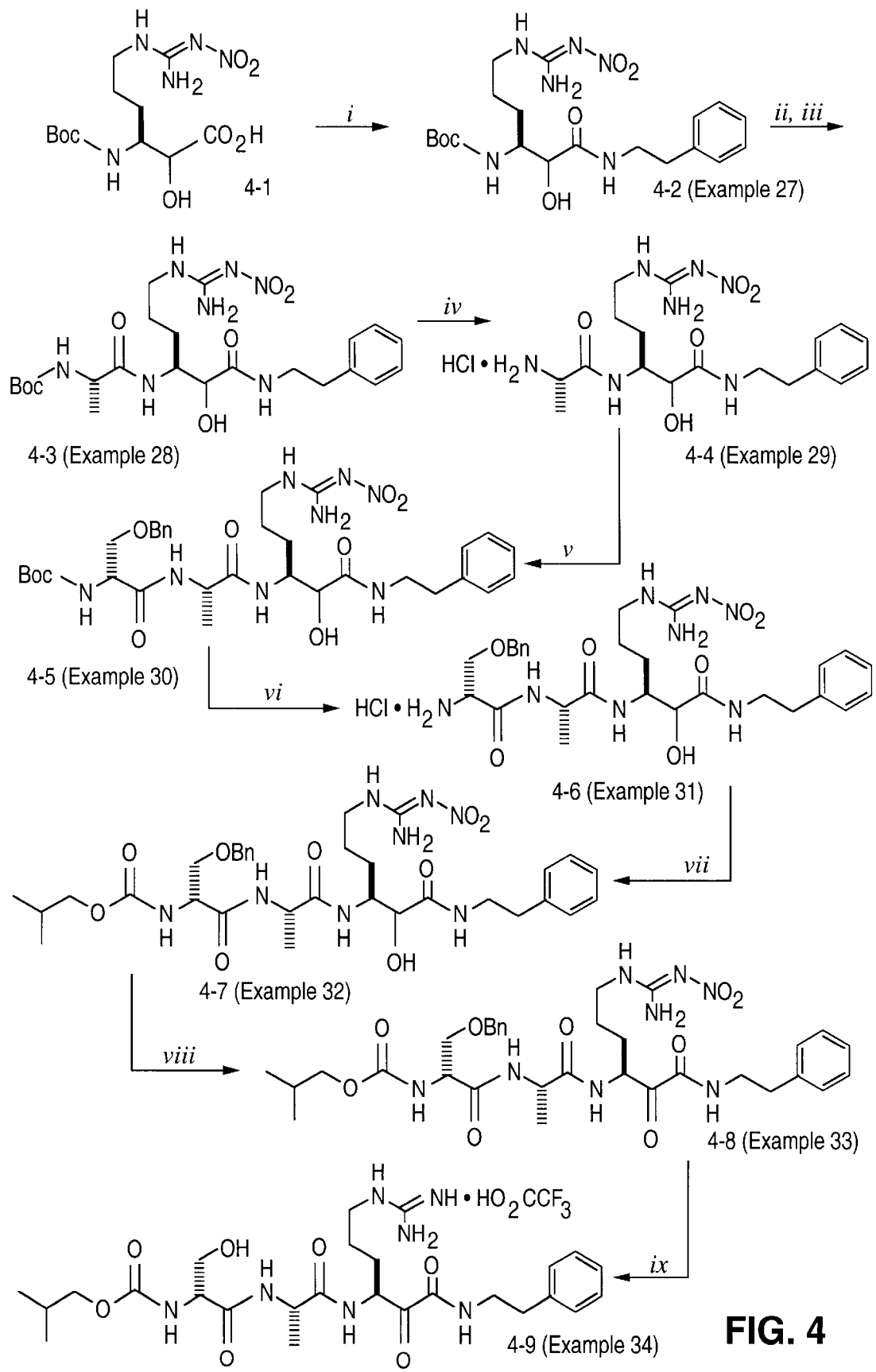
FIG. 4 depicts a reaction scheme for the synthesis of compounds of the present invention having an arginine ketoamide group at P1. In this figure "i" through "ix" are defined as: i) phenethylamine, BOP and 1-hydroxybenzotriazole, DMF, 4-methylmorpholine, 89% yield after work-up; ii) HCl in ethyl acetate, to give N$^g$-nitroArg-COH-phenethylamide hydrochloride salt; iii) t-butoxycarbonyl-Ala-OH, EDC, 1-hydroxybenzotriazole, and acetonitrile, diisopropylethylamine, 95% yield after workup; iv) HCl in ethyl acetate, 98% yield after workup; v) t-butoxycarbonylserine benzyl ether EDC and 1-hydroxybenzotriazole, acetonitrile, diisopropylethylamine, yield 92% after workup; vi) HCl in ethyl acetate, 98% yield after workup; vii) acetonitrile, isobutyl chloroformate, diisopropylethylamine, 85% yield after workup; viii) EDC, methylsulfoxide and dichloroacetic acid, 68% yield after workup; ix) anisole, HF at −20° C., 26% yield after workup and purification by preparative reverse phase HPLC. See also Examples 27 to 34.

FIG. 4 depicts a synthesis scheme for compounds of the present invention having an arginine ketoamide group at P1.

Synthesis of such a compound is further described by Examples 27 to 34.

Examples 35 to 40 describe solution phase synthesis of a preferred compound of the present invention using an L-$N^g$-nitroargininal ethyl cyclol intermediate.

Figure 5:
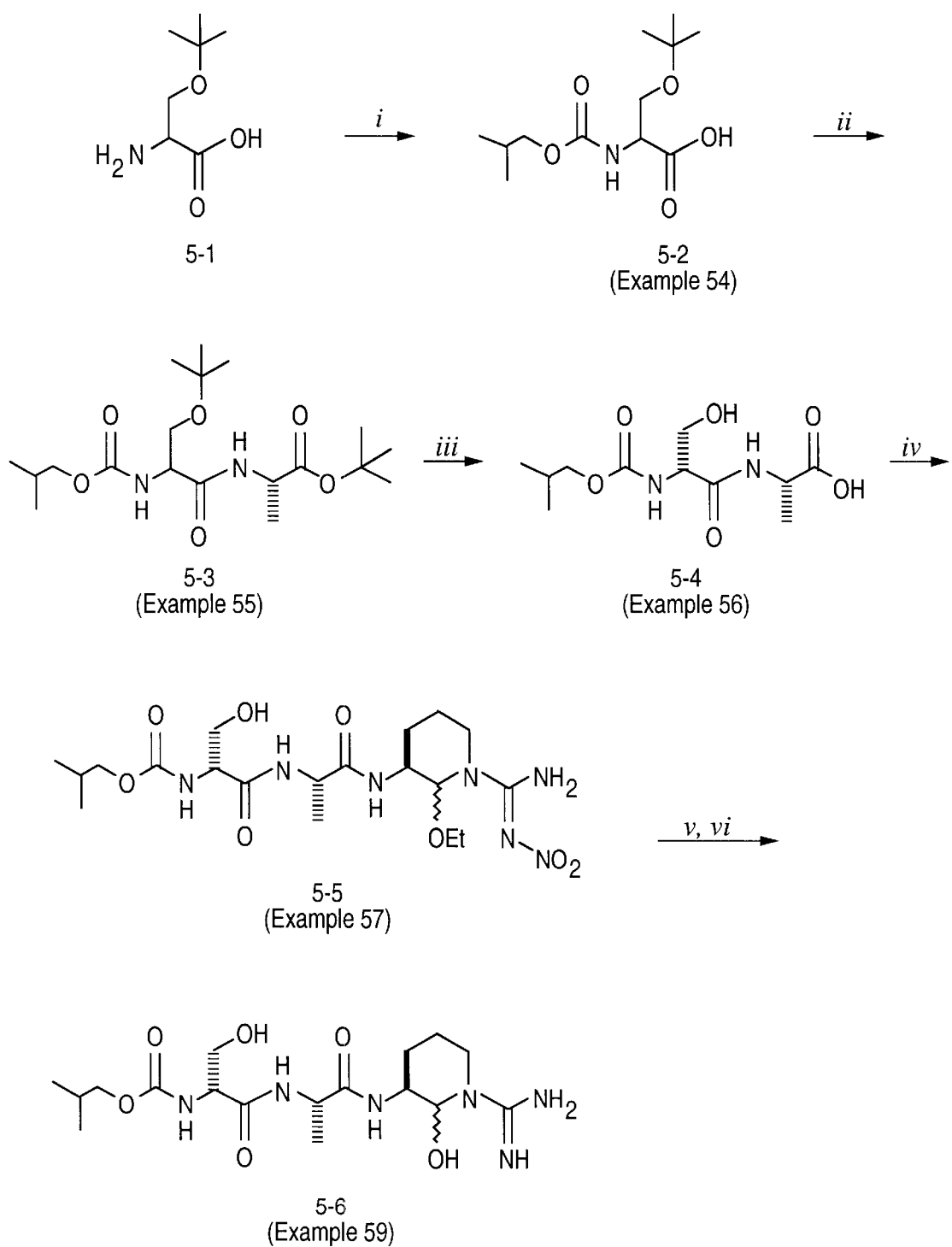
FIG. 5 depicts a reaction scheme for an alternate solution phase sythetic route to prepare Compound 1 (the compound depicted in FIG. 2) an L-N$^g$-nitroargininal ethyl cyclol intermediate. In this figure, "i" through "vi" are defined as: i) isobutyl chloroformate, sodium carbonate, water, 99.5% yield after workup; ii) alanine t-butyl ester, hydrochloride salt, EDC, and hydroxybenzotriazole in acetonitrile; diisopropylethylamine, quantitative yield after workup; iii) TFA, DCM, quantitative yield after workup; iv) N$^g$-nitroargininal ethyl cyclol, HCl salt, EDC, and hydroxybenzotriazole in acetonitrile; diisopropylethylamine, 50% yield after workup; v) ethanol/acetic acid/water (4:1:1), 10% palladium on carbon, H$_2$ at 50 psi, 4 hours; vi) 3.0M HCl; preparative reverse phase HPLC; 62% yield of compound 1 for two (v and vi) steps. See also Examples 54 to 59.

FIG. 5 depicts an alternate synthetic route to prepare the compound depicted in FIG. 2 using solution phase synthesis and an L-$N^g$-nitroargininal ethyl cyclol intermediate. See also Examples 54 to 59.

Figure 6:
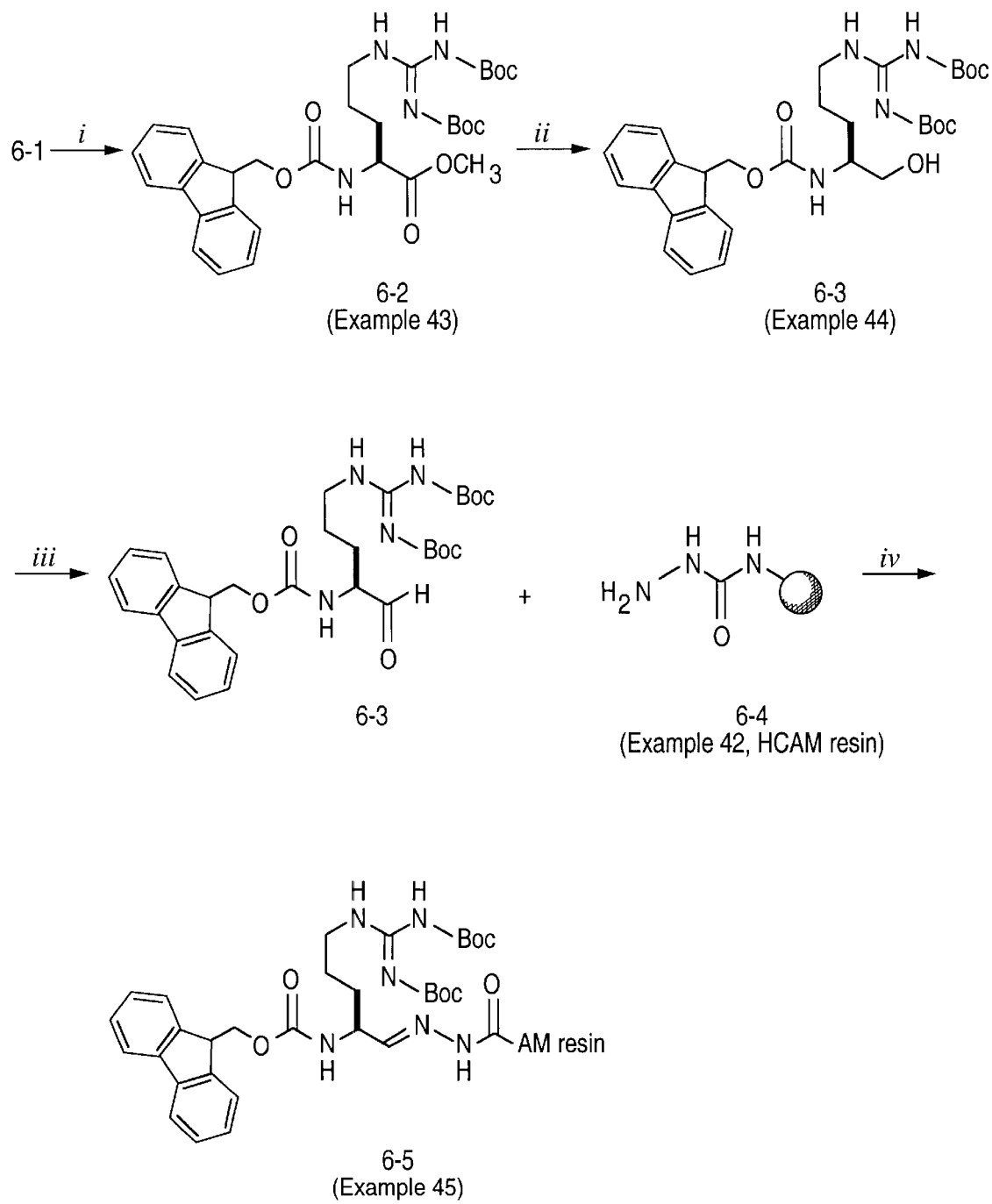
FIG. 6 depicts a reaction scheme for the synthesis of a protected argininal hydrazonylcarbonyl aminomethylated polystyrene resin used in the solid phase synthesis of compounds of the present invention having an argininal at P1. Compound 6-1 is N-α-fluorenylmethyloxycarbonyl-omega, omega-di-N-t-butoxycarbonyl-arginine. In this figure, "i" through "iv" are defined as: i) acetonitrile, potassium carbonate, methyl iodide, 50° C., ethyl acetate; ii) THF and methanol, calcium chloride, ice bath, sodium borohydride, stirring, 71% yield after workup; iii) methylsulfoxide, and toluene, ice bath, EDC and dichloroacetic acid; and iv) DCM, HCAM resin, ambient temperature 16 to 24 hours. See also Examples 41 to 45.

FIG. 6 depicts a synthesis scheme and Examples 41 to 45 further describe synthesis of argininal-hydrazonylcarbonyl aminomethylated resins which may be used to prepare compounds of the present invention.

FIG. 7 depicts a synthetic scheme for solid phase preparation of compounds of the present invention using the resin of Example 45. Examples 46 to 53 further describe such solid phase syntheses.

Figure 8:
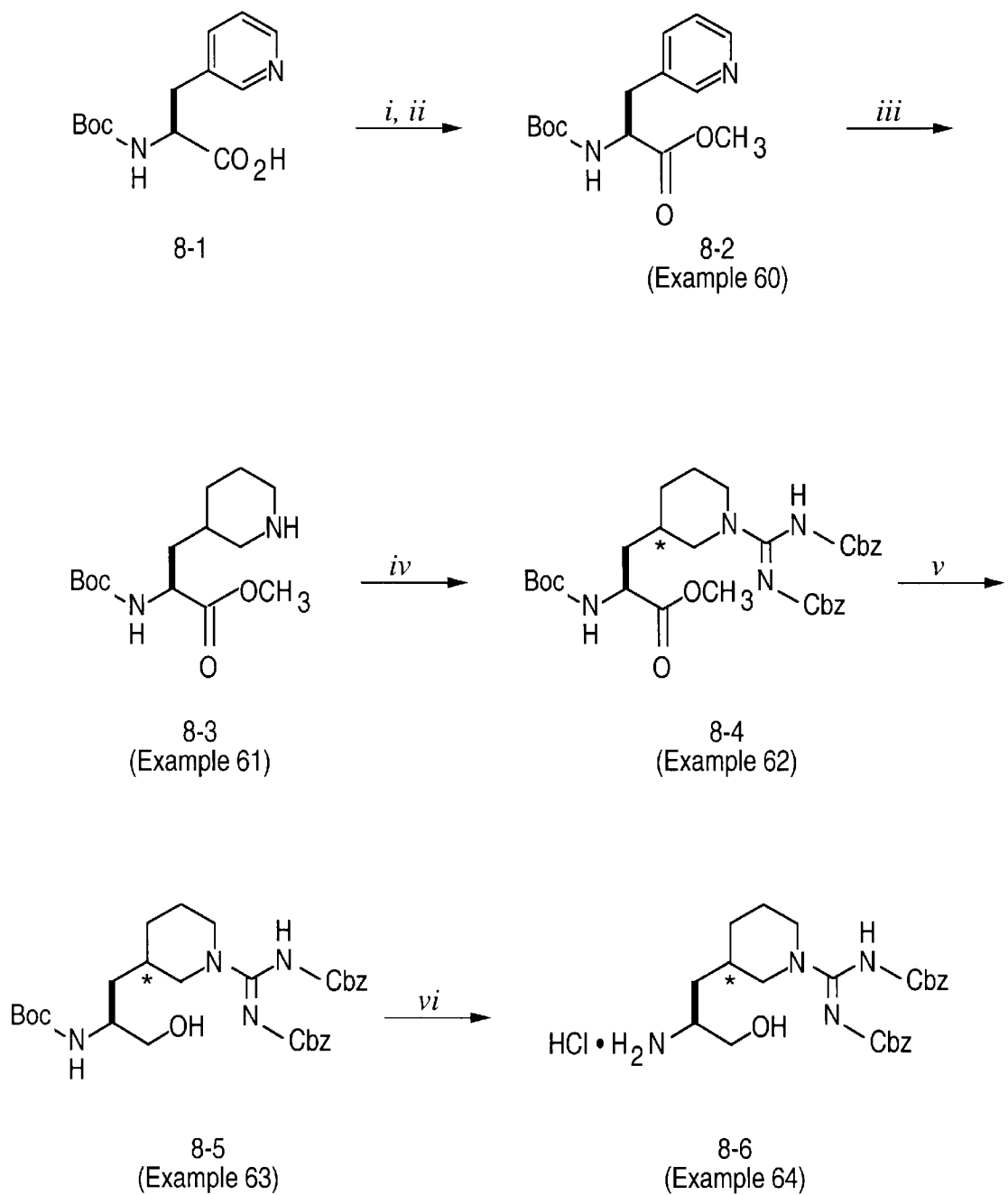
FIG. 8 depicts a reaction scheme for preparation of an intermediate used for the synthesis of compounds of the present invention having a 3-piperidinyl-(N-guanidino) alaninal at P1. In this figure, "i" through "vi" are defined as: i) thionyl chloride, methanol; ii) di-tert-butyl dicarbonate, pH 7 to 8; iii) hydrogen gas, platinum oxide in ethanol, water and acetic acid; iv) bis-benzyloxycarbonyl S-methylisothiourea, base, tetrahydrofuran; v) calcium chloride, sodium borohydride in tetrahydrofuran and ethanol; vi) HCl, ethyl acetate. "*" indicates the position of an asymmetric carbon atom. See also Examples 60 to 64.

FIG. 8 depicts a synthetic scheme for preparation of an intermediate used in synthesizing compounds of the present invention having an 3-piperidinyl-(N-guanidino)-alaninal group at P1. Examples 60 to 64 describe its preparation in further detail.

Figure 9:
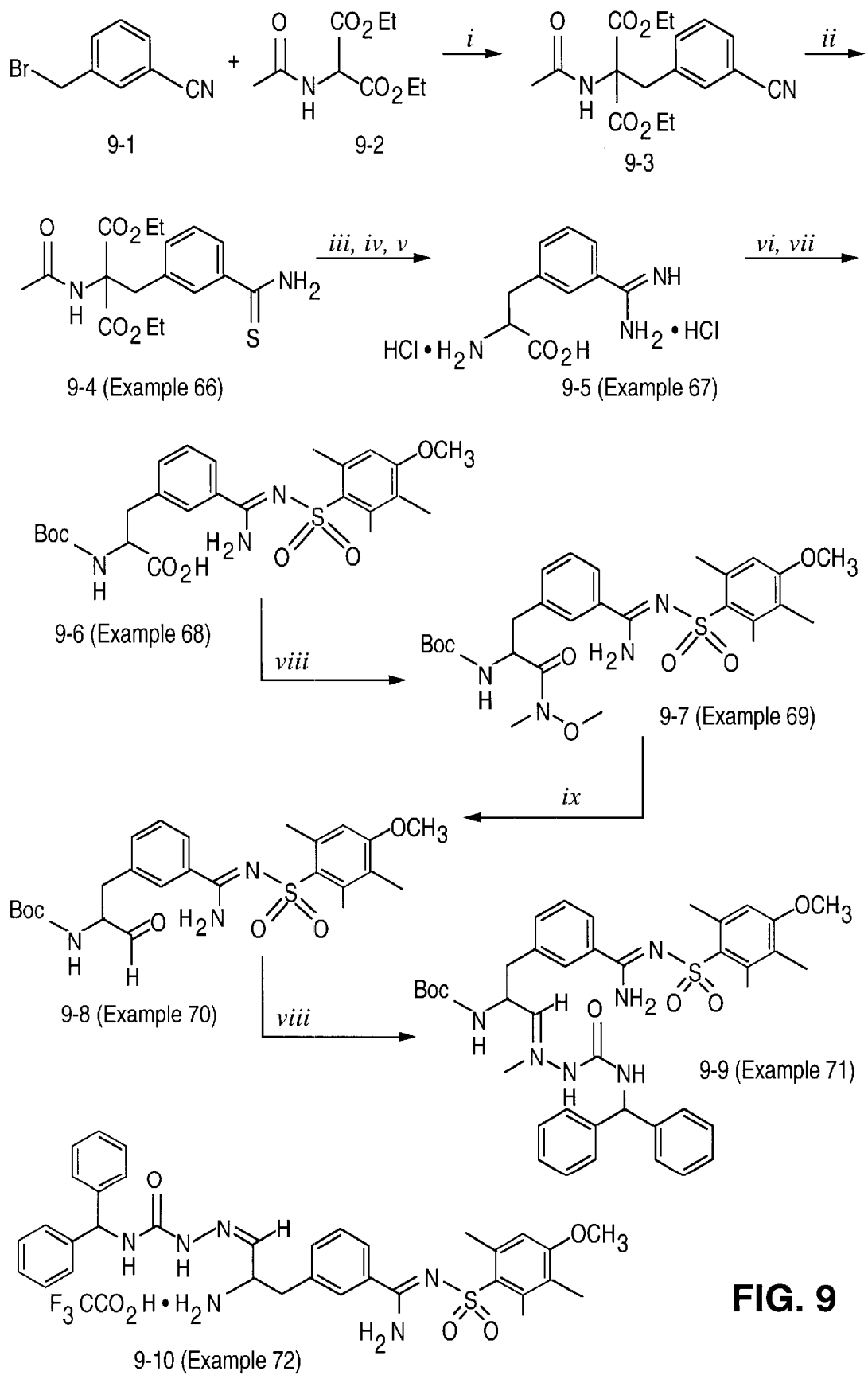
FIG. 9 depicts a reaction scheme for preparation of an intermediate used for the synthesis of compounds of the present invention having a 3-amidinophenylalaninal at P1. In this figure, "i" through "xi" are defined as i) potassium iodide, dioxane; 2.5 M sodium ethoxide in ethanol, argon atmosphere, reflux 6 hours; yield after work up 60%; ii) pyridine, triethylamine; H$_2$S(g), stirred at room temperature 16 hours, yield after work up 98%; iii) acetone, iodomethane, reflux 30 minutes, filtration, methanol; iv) ammonium acetate, reflux 1 hour, filter and dry; v) concentrated HCl, reflux 3 hours, yield after workup 30%; vi) dioxane, sodium bicarbonate, di-t-butyl dicarbonate, stir 18 hours at room temperature; vii) 4° C., 4.0 N NaOH to pH 12; 4-methoxy-2,3,6-trimethylbenzene sulfonyl chloride in dioxane; 1.0 N HCl to pH 7 to 8, water, yield after work up 68%, viii) O, N-dimethylhydroxylamine hydrochloride, hydroxybenzotriazole hydrate, 4-methylmorpholine, THF, stir 2 hours, yield after workup 69%; ix) LiAlH$_4$, THF, −78° C.; aqueous potassium bisulfate, yield after workup 86%; x) 4-benzhydrylsemicarbizide trifluoroacetate salt (the compound of Example 65), sodium acetate trihydrate in ethanol, reflux, yield after workup 89%; and xi) 50% TFA/DCM, add to ether, yield after workup 79%. See also Examples 65 to 72.

FIG. 9 depicts a reaction scheme for preparation of an intermediate which is used in the synthesis of compounds of the present invention having a 3-amidinophenylalaninal group at P1. Intermediates used in the preparation of compounds of formula (I) having a 4-amidinopherylalaninal group at P1 may be prepared according to the reaction scheme depicted in FIG. 9 and described in Examples 65 to 72, using the appropriate α-bromo-para-tolunitrile starting material.

Figure 10:
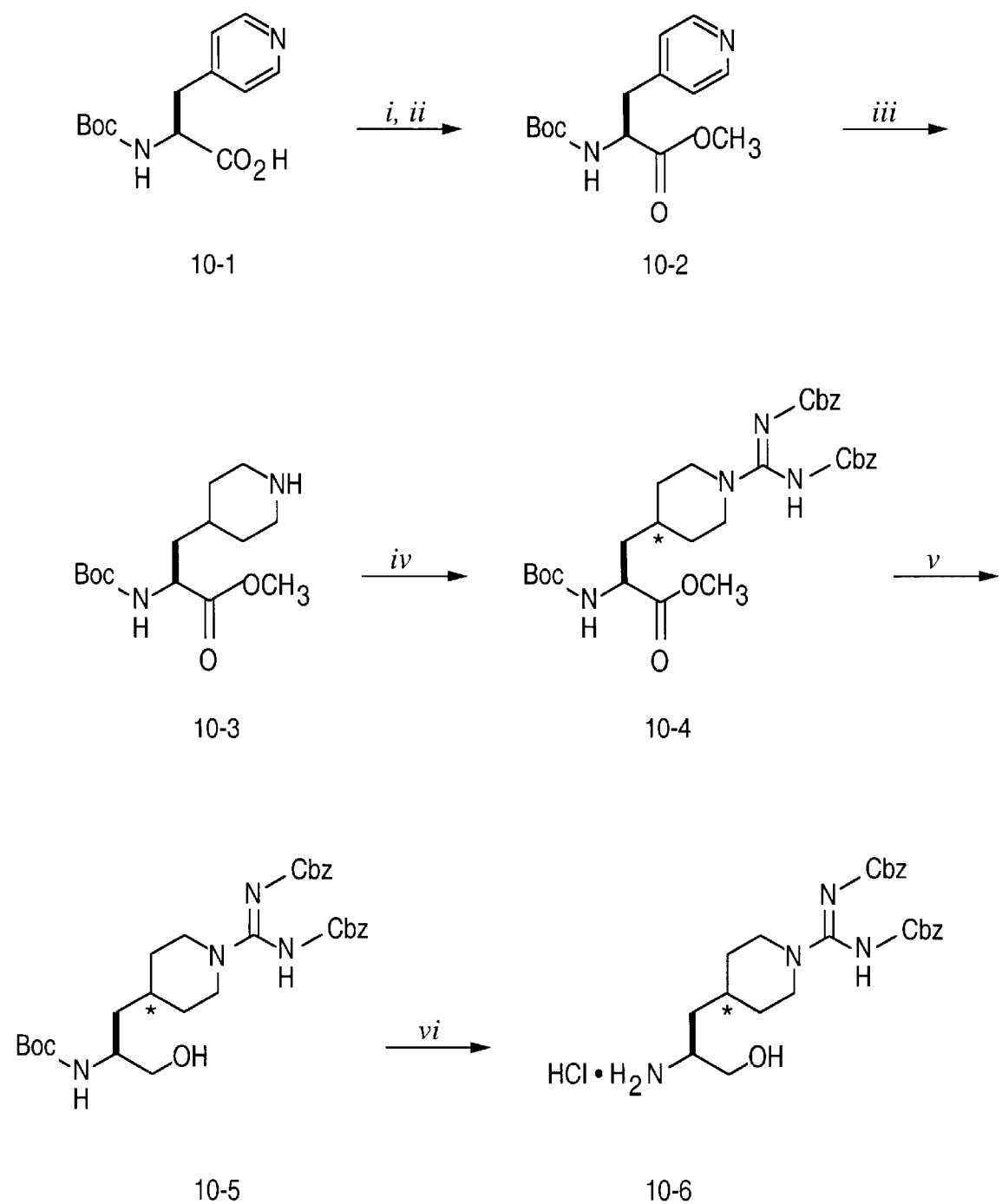
FIG. 10 depicts a reaction scheme for the preparation of an intermediate which is used in the synthesis of compounds of the present invention having a 4-piperidinyl-(N-guanidino)alaninal at P1. In this figure, "i" through "vi" are defined as i) thionyl chloride, methanol; ii) di-tert-butyl carbonate, pH 7 to 8; iii) hydrogen gas, platinum oxide in ethanol, water and acetic acid; iv) bis-benzyloxycarbonyl S-methylisothiourea, base, tetrahydrofuran; v) calcium chloride, sodium borohydride in tetrahydrofuran and ethanol; and vi) HCl in ethyl acetate. "*" indicates the position of an asymmetric carbon atom. See Example 73.

FIG. 10 depicts a reaction scheme for the preparation of an intermediate which is used in the synthesis of compounds of the present invention having a 4-piperidinyl-(N-guanidino)alaninal group at P1. This intermediate is prepared using procedures similar to those described in Examples 60 to 64 and using the appropriate starting materials.

Figure 11:
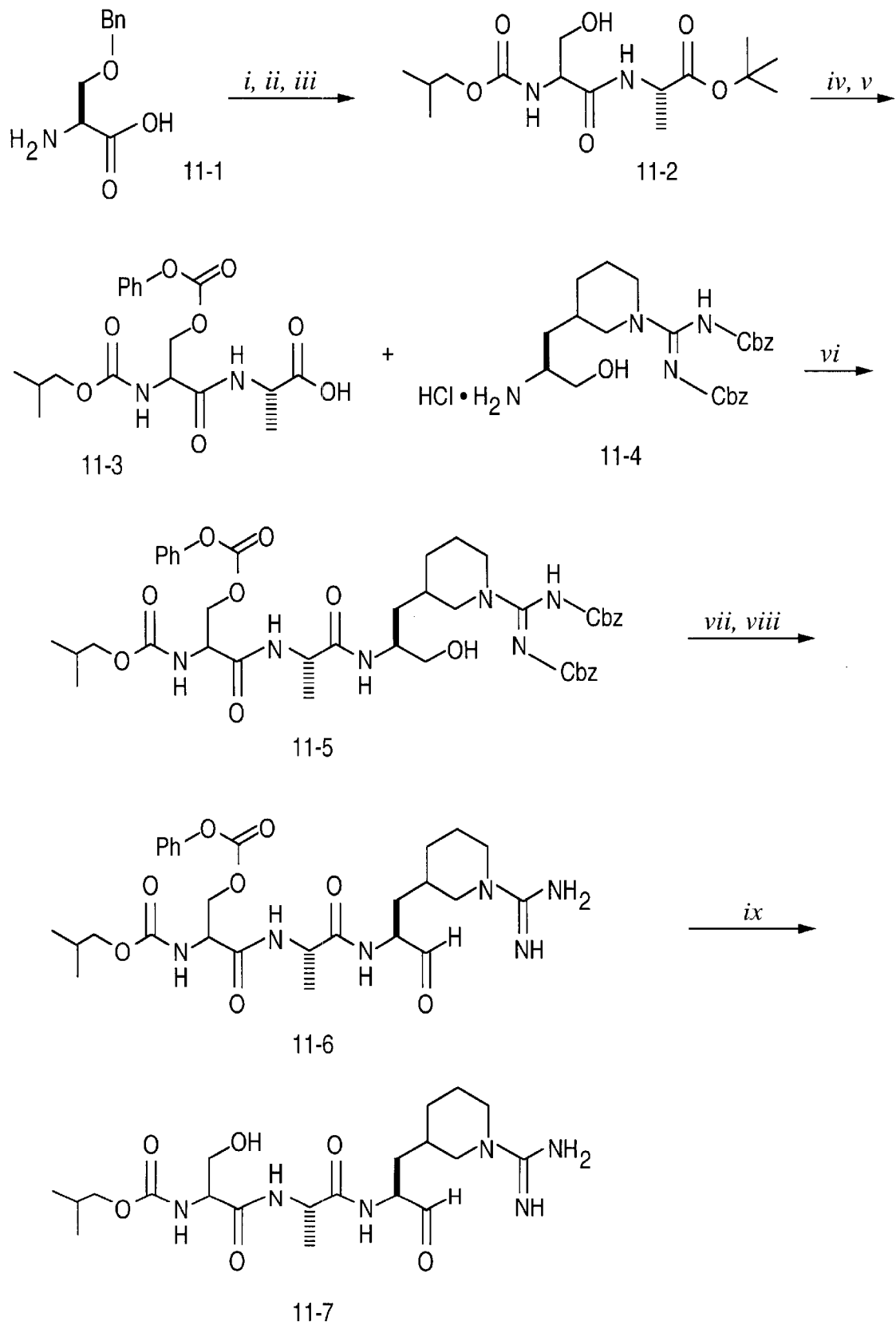
FIG. 11 depicts a reaction scheme for synthesis of a compound of the present invention having a 3-guanidino-piperidinal group at P1 using an intermediate such as 8-6 of FIG. 8. In this figure, "i" through "ix" are defined as: i) isobutylchloroformate, sodium bicarbonate, aqueous dioxane; ii) alanine t-butyl ester, EDC, HOBt, NMM; iii) $H_2$, Pd/C; iv) pyridine, phenyl chloroformate; v) TFA/DCM; vi) EDC, HOBt, NMM; vii) $H_2$, Pd/C; viii) EDC, DCA, DMSO, toluene; and ix) $H_2O$, pH 7; preparative reverse-phase HPLC. See Example 74.

FIG. 11 depicts a reaction scheme for preparation of a compound of the present invention having a 3-piperidinyl-(N-guanidino)alaninal group at P1 using an intermediate such as 8-6 of FIG. 8.

Figure 12:
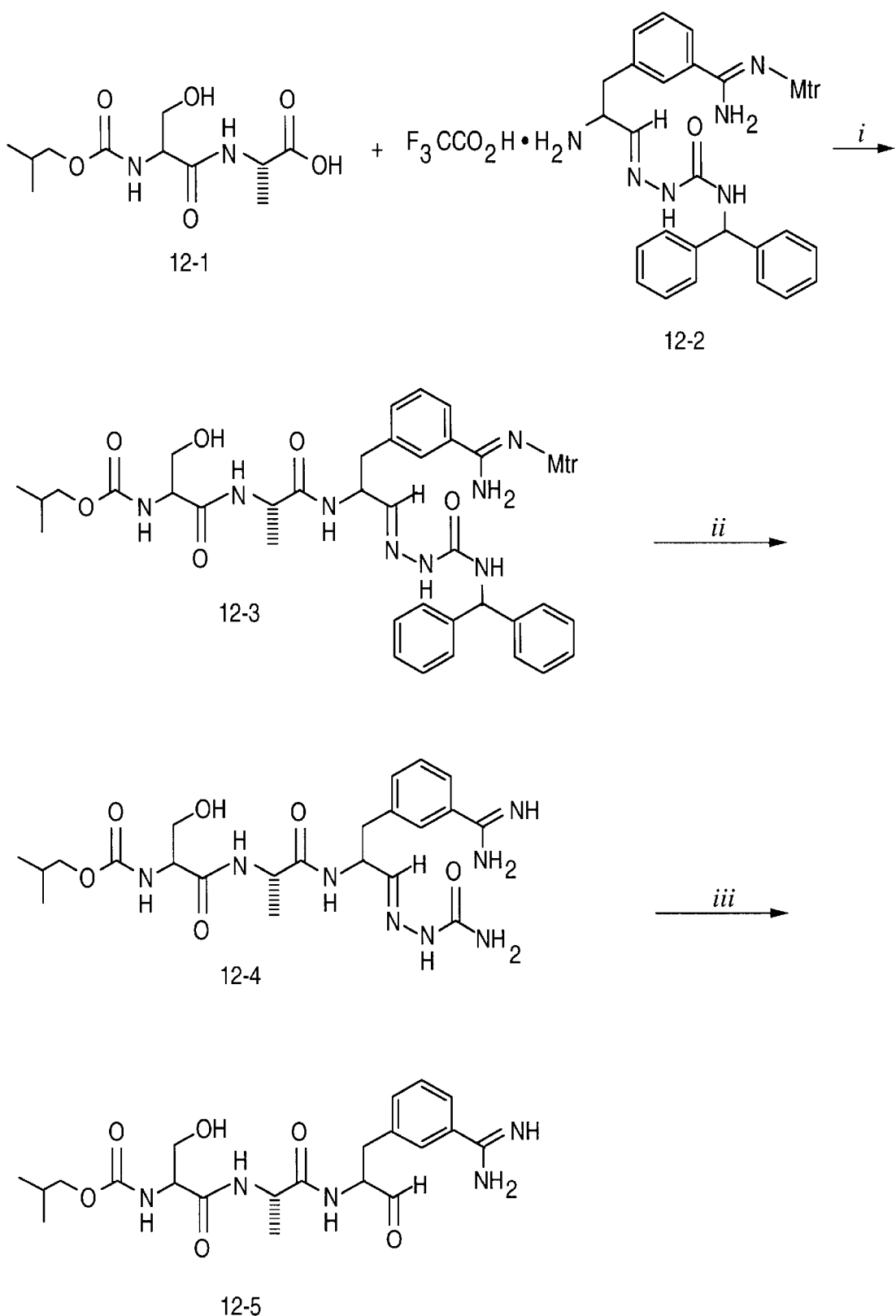
FIG. 12 depicts a reaction scheme for synthesis of a compound of the present invention having an amidino-phenylalaninal at P1 using an intermediate such as 9-10 of FIG. 9. In this figure, "i" through "iii" are defined as: i) EDC, HOBt, NMM; ii) HF, anisole; and iii) 90% aqueous TFA; preparative reverse-phase HPLC. See Example 75.

FIG. 12 depicts a reaction scheme for preparation of a compound of the present invention having a 3-amidinophenylalaninal group at P1 using an intermediate such as 9-10 of FIG. 9.

Preferred means of chemically coupling (as for example, amide bond function) include formation of a peptide bond by using conventional coupling reagents known in the art. See Bodanszky, N. *Peptide Chemistry*, pp. 55-73, Springer-Verlag, New York (1988) and references cited therein. The chemical coupling may be either by means of one-step or two-step coupling. In one-step coupling, the two coupling partners are coupled directly. Preferred coupling reagents for one-step coupling of the include DCC with HOBt, EDC with HOBt, EDC with HOAt, HBTU or TBTU. In two-step coupling, an activated ester or anhydride of the C-terminal carboxy group of one coupling partner is formed prior to its coupling to the other coupling partner.

For preparation of certain compounds having hydrogenation-sensitive substituent groups, it is preferred to avoid the use of hydrogen gas with palladium on carbon. Another preferred method for preparing compounds of the present invention containing hydrogenation sensitive groups such as alkenyl or aryl moieties substituted with halogen, cyano, nitro, or —S—$Z_1$, is to use boron tris (trifluoroacetate), $B(OCOCF_3)_3$, to cleave the $N^g$-nitro of the arginine group. The reagent is prepared by the reaction of $BBr_3$ and $CF_3COOH$ in dichloromethane at 0° C. The reagent is also commercially available. Generally, the $N^g$-nitro compound is treated with boron tris (trifluoroacetate) in trifluoroacetic acid at 0° C. See, e.g., Fieser, M. and Fieser, L. F., *Reagents for Organic Synthesis*, p. 46, John Wiley & Sons, New York (1974); Pless, J., and Bauer, W. *Angew. Chem., Internat. Ed.*, 12, 147 (1973).

In addition, another preferred reagent for selective nitro group cleavage is titanium trichloride. This reagent is commercially available. The $N^g$ nitro compound is treated with titanium trichloride in aqueous methanol containing an ammonium acetate buffer followed by exposure of the reaction mixture to air or dimethyl sulfoxide. Freidinger, R. M., Hirschmann, R., and Veber, D. F., *J. Org. Chem.*, 43, 4800 (1978).

Another preferred method for synthesizing these compounds having an L-argininal moiety is to use the di-N-t-butoxycarbonyl protecting group for the L-argininal moiety for groups incompatible with hydrogenation with palladium on carbon. For example, α-N-benzyloxycarbonyl-omega, omega'-di-N-t-butoxycarbonylarginine is dissolved in acetonitrile and treated with hydroxybenzotriazole and 1-ethyl-3-(3-dimethylamino-propyl) carbodiimide HCl salt to form α-N-benzyloxycarbonyl-omega,omega'-di-N-t-butoxycarbonyl-L-arginine lactam. The lactam is reduced by treatment with $LiAlH_4$ in THF at −70° C. to provide α-N-benzyloxycarbonyl-omega,omega;-di-N-t-butoxycarbonyl-L-argininal. This aldehyde is protected as the diethyl acetal by treatment with ethanol and HCl. The N-benzyloxycarbonyl protecting group is removed by treatment with hydrogen gas and palladium on carbon to give omega, omega'-di-N-t-butoxycarbonyl-L-argininal diethyl acetal, HCl salt. This protected L-argininal moiety can then be coupled to a desired carboxylic acid by treatment with N-hydroxybenzotriazole and 1-ethyl-3-(3-dimethylamino-propyl) carbodiimide HCl salt. The diethyl acetal and the di-Boc protecting groups are removed by treatment with hexafluorophosphoric acid in acetonitrile at 0° C. The reaction mixture is quenched by addition of 2.5 M aqueous sodium acetate until pH 4 is reached. The mixture is filtered through a 2 micron filter. Preparative HPLC using 0.1% $CF_3COOH$ in 10–40% aqueous acetonitrile provides the trifluoroacetate salt of the desired substituted L-argininal compound.

3. Selection of Preferred Compounds

Preferred compounds of the present invention are selected for their potency and selectivity toward inhibition of serine proteases, especially urokinase. Such evaluations are routinely performed in vitro, following procedures such as those set forth in Example A. As described therein, and as generally known, a target serine protease and its substrate are combined under assay conditions permitting reaction of the protease with its substrate. The assay is performed in the absence of test compound, and in the presence of increasing concentrations of the test compound. The concentration of test compound at which 50% of the serine protease activity is inhibited by the test compound is the $IC_{50}$ value (Inhibitory Concentration) or $EC_{50}$ (Effective Concentration) value for that compound. Within a series or group of test compounds, those having lower $IC_{50}$ or $EC_{50}$ values are considered more potent inhibitors of the serine protease than those compounds having higher $IC_{50}$ or $EC_{50}$ values. The $IC_{50}$ measurement is often used for more simplistic assays, whereas the $EC_{50}$ is often used for more complicated assays, such as those employing cells.

Preferred compounds within the present invention have an $IC_{50}$ value of 100 nM or less as measured in an in vitro assay for inhibition of urokinase activity. Especially preferred compounds have an $IC_{50}$ value of less than 30 nM.

The test compounds also are evaluated for selectivity toward a serine protease. As described in the Examples, and as generally known, a test compound is assayed for its potency toward a panel of serine proteases and other enzymes and an $IC_{50}$ value or $EC_{50}$ value is determined for each test compound in each assay system. A compound that demonstrates a low $IC_{50}$ value or $EC_{50}$ value for the target enzyme, e.g., urokinase, and a higher $IC_{50}$ value or $EC_{50}$ value for other enzymes within the test panel (e.g., tissue plasminogen activator, thrombin, Factor Xa), is considered to be selective toward the target enzyme. Generally, a compound is deemed selective if its $IC_{50}$ value or $EC_{50}$ value in the target enzyme assay is at least one order of magnitude less than the next smallest $IC_{50}$ value or $EC_{50}$ value measured in the selectivity panel of enzymes.

Preferred compounds of the present invention have an $IC_{50}$ value of 100 nM or less as measured in an in vitro assay for inhibition of urokinase activity. Especially preferred compounds have an $IC_{50}$ value in the in vitro urokinase inhibition assay that is at least one order of magnitude smaller than the $IC_{50}$ value measured in the in vitro tPA inhibition assay. Compounds having a selectivity ratio of $IC_{50}$ tPA assay: $IC_{50}$ urokinase assay of greater than 100 are especially preferred.

Compounds of the present invention also are evaluated for their activity in vivo. The type of assay chosen for evaluation of test compounds will depend on the pathological condition to be treated or prevented by use of the compound, as well as the route of administration to be evaluated for the test compound.

For instance, to evaluate the activity of a compound of the present invention to reduce tumor growth through inhibition of urokinase, the procedures described by Jankun et al. [Canc. Res. 57:559–563, 1997] to evaluate PAI-1 can be employed. Briefly, the ATCC cell lines DU145, which expresses a high level of uPA, and LnCaP, which does not express uPA, are injected into SCID mice. After tumors are established, the mice are given test compound according to a dosing regime determined from the compound's in vitro characteristics. The Jankun et al. compound was administered in water. Tumor volume measurements are taken twice a week for about five weeks. A compound is deemed active if an animal to which the compound was administered exhibited decreased tumor volume, as compared to animals receiving appropriate control compounds. Furthermore, a comparison of a compound's effect in animals injected with DU145 cells versus LnCaP cells can indicate whether the compound's effect was due to inhibition of urokinase or otherwise.

Another in vivo experimental model designed to evaluate the effect of p-aminobenzamidine, a purported urokinase inhibitory compound, on reducing tumor volume is described by Billström et al. [Int. J. Cancer 61:542–547, 1995].

To evaluate the ability of a compound of the present invention to reduce the occurrence of, or inhibit, metastasis, the procedures described by Kobayashi et al. [Int. J. Canc. 57:727–733d, 1994] to evaluate possible peptide antagonists of urokinase can be employed. Briefly, a murine xenograft selected for high lung colonization potential is injected into C57B1/6 mice i.v. (experimental metastasis) or s.c. into the abdominal wall (spontaneous metastasis). Various concentrations of the compound to be tested can be admixed with the tumor cells in Matrigel prior to injection. Daily i.p. injections of the test compound are made either on days 1–6 or days 7–13 after tumor inoculation. The animals are killed about three or four weeks after tumor inoculation, and the lung tumor colonies are counted. Evaluation of the resulting data permits a determination as to efficacy of the test compound, optimal dosing and route of administration.

The activity of the compounds of the present invention toward decreasing tumor volume and metastasis can be evaluated in the model described by Rabbani et al. [Int. J. Cancer 63:840–845, 1995] to evaluate the B-428 urokinase inhibitor. There, Mat LyLu tumor cells over-expressing uPA were injected into the flank of Copenhagen rats. The animals were implanted with osmotic minipumps to continuously administer various doses of test compound for up to three weeks. The tumor mass and volume of experimental and control animals were evaluated during the experiment, as were metastatic growths. Evaluation of the resulting data permits a determination as to efficacy of the test compound, optimal dosing, and route of administration. Some of these authors described a related protocol in Xing et al. [Canc. Res. 57:3585–3593, 1997].

To evaluate the inhibitory activity of a compound of the present invention toward neovascularization, a rabbit cornea neovascularization model can be employed. Avery et al. [Arch. Ophthalmol. 108:1474–1475, 1990] describe anesthetizing New Zealand albino rabbits and then making a central corneal incision and forming a radial corneal pocket. A slow release prostaglandin pellet was placed in the pocket to induce neovascularization. Test compound was administered i.p. for five days, at which time the animals were killed. The effect of the test compound is evaluated by review of periodic photographs taken of the limbus, which can be used to calculate the area of neovascular response and, therefore, limbal neovascularization. A decreased area of neovascularization as compared with appropriate controls indicates the test compound was effective at decreasing or inhibiting neovascularatization.

An angiogenesis model used to evaluate the effect of a urokinase receptor antagonist is described by Min et al. [Canc. Res. 56:2428–2433, 1996]. C57BL6 mice receive s.c. injections of a Matrigel mixture containing bFGF, as the angiogenesis-inducing agent, with and without test compound. After five days, the animals are killed and the Matrigel plugs, in which neovascularization can be visualized, are photographed. An experimental animal receiving Matrigel and an effective dose of test compound will exhibit less vascularization than a control animal or an experimental animal receiving a less- or non-effective dose of compound.

An in vivo system designed to test compounds for their ability to limit the spread of primary tumors is described by Crowley et al. [Proc. Natl. Acad. Sci. 90:5021–5025, 1993]. Nude mice are injected with tumor cells (PC3) engineered to express CAT (chloramphenicol acetyltransferase). The cells secrete large amounts of uPA and exhibit saturating amounts of uPA activity bound to uPAR on the cell surface. Compounds to be tested for their ability to decrease tumor size and/or metastases are administered to the animals, and subsequent measurements of tumor size and/or metastatic growths are made. In addition, the level of CAT detected in various organs provides an indication of the ability of the test compound to inhibit metastasis; detection of less CAT in tissues of a treated animal versus a control animal indicates less CAT-expressing cells migrated to that tissue.

In vivo experimental models designed to evaluate the urokinase inhibitory potential of a test compound, using a tumor cell line F3II, said to be highly invasive, are described by Alonso et al. [Breast Canc. Res. Treat. 40:209–223, 1996]. This group describes in vivo studies for toxicity determination, tumor growth, invasiveness, spontaneous metastasis, experimental lung metastasis, and an angiogenesis assay.

The CAM model (chick embryo chorioallantoic membrane model), first described by L. Ossowski in 1998 [J. Cell Biol. 107:2437–2445, 1988], provides another method for evaluating the urokinase inhibitory activity of an invented compound. In the CAM model, invasion of tumor cells through the chorioallantoic membrane is dependent upon the presence of catalytically active uPA. Contacting CAM with tumor cells in the presence of a urokinase inhibitory agent results in less or no invasion of the tumor cells through the membrane. Thus, the CAM assay is performed with CAM and tumor cells in the presence and absence of various concentrations of test compound. The invasiveness of tumor cells is measured under such conditions to provide an indication of the compound's urokinase inhibitory activity. A compound having urokinase inhibitory activity correlates with less tumor invasion.

4. Pharmaceutical Compositions

In another aspect, the present invention encompasses pharmaceutical compositions prepared for storage or administration which comprise a therapeutically effective amount of a compound of the present invention in a pharmaceutically acceptable carrier.

The therapeutically effective amount of a compound of the present invention will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy but will depend on such factors as weight, diet, concurrent medication and other factors which those skilled in the medical arts will recognize.

The therapeutically effective amount of the compound of the present invention can range broadly depending upon the desired affects and the therapeutic indication. Typically, dosages will be between about 0.01 mg/kg and 100 mg/kg body weight, preferably between about 0.01 and 10 mg/kg, body weight.

Pharmaceutically acceptable carriers for therapeutic use are well known in the pharmaceutical art, and are described, for example, in *Remington's Pharmaceutical Sciences*, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

The pharmaceutical compositions of the present invention may be formulated and used as tablets, capsules or elixirs for oral administration; suppositories for rectal administration; sterile solutions and suspensions for injectable administration; and the like. The dose and method of administration can be tailored to achieve optimal efficacy but will depend on such factors as weight, diet, concurrent medication and other factors which those skilled in the medical arts will recognize.

When administration is to be parenteral, such as intravenous on a daily basis, injectable pharmaceutical compositions can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, or the like. In addition, if desired, the injectable pharmaceutical compositions may contain minor amounts of nontoxic auxiliary substances, such as wetting agents, pH buffering agents, and the like. If desired, absorption enhancing preparations (e.g., liposomes) may be utilized.

5. Utility

The urokinase inhibitors of the present invention may be used both in vitro and in vivo for a number of applications, some of which are described herein below.

The compounds of the present invention are active as inhibitors of urokinase and specifically bind urokinase. Accordingly those compounds that contain sites suitable for linking to a solid/gel support may be used in vitro for affinity chromatography to purify urokinase from a sample or to remove urokinase from a sample using conventional affinity chromatography procedures. These compounds are attached or coupled to an affinity chromatography either directly or through a suitable linker support using conventional methods. See, e.g. Current Protocols in Protein Science, John Wiley & Sons (J. E. Coligan et al., eds, 1997) and Protein Purification Protocols, Humana Press (S. Doonan, ed., 1966) and references therein.

The urokinase inhibitors of the present invention are useful in in vitro assays to measure tPA activity in a sample. In assays which measure the total plasminogen activation activity in a blood sample, a urokinase inhibitor of the present invention will knock out that portion of plasminogen activation attributable to uPA, which will allow for calculation of the portion of the total plasminogen activation due to tPA activity as well as that due to uPA activity. Use of such assays to monitor tPA activity would allow better dosage control in patients receiving tPA. These assays could also be used to monitor uPA activity levels in tissue samples, such as from biopsy or to monitor uPA/tPA activities for any clinical situation where measurement of plasminogen activation activity is of assistance. These assays may also be used to monitor plasminogen activator activity where a patient has been treated with a non-endogenous compound having plasminogen activator activity, such as streptokinase and staphlyokinase.

The urokinase inhibitors are useful in vivo for treatment of pathologic conditions which would be ameliorated by decreased urokinase activity. Accordingly, these compounds will be useful in decreasing or inhibiting metastasis, neovascularization, and degradation of the extracellular matrix in tumors and other neoplasms. These compounds will be useful as therapeutic agents in treating conditions characterized by pathological neovascularation such as retinal disease, retinopathies and other conditions, including those described hereinabove in the Background and Introduction to the Invention. These compounds will inhibit the activation of metalloproteases by the uPA-plasmin cascade in synovial fluid and thus, may be used in treatment of arthritis.

Another use for the urokinase inhibitors of the present invention is as an antidote if too much exogenous urokinase has been given to a patient for therewith purposes, such as for dissolving a blood clot.

The urokinase inhibitors may be used in treating conditions characterized by inflammation due to their anti-inflammatory effects from inhibition of urokinase, thereby interfering with mediators of cell adhesion or migration. Such anti-inflammatory applications include treatment of stroke and complications of organ transplants.

The present invention includes methods for preventing a condition in a mammal suspected of having a condition which will be attenuated by inhibition of urokinase activity comprising administering to said mammal a therapeutically effective amount of a compound or a pharmaceutical composition of the present invention.

The compounds or pharmaceutical compositions of the present invention are administered in vivo, ordinarily in a mammal, preferably in a human. In employing them in vivo, the compounds or pharmaceutical compositions can be administered to a mammal in a variety of ways, including orally, parenterally, intravenously, subcutaneously, intramuscularly, colonically, rectally, nasally or intraperitoneally, employing a variety of dosage forms. Administration is preferably oral, such as by tablets capsules or elixers taken on a daily basis.

In practicing the methods of the present invention, the compounds or pharmaceutical compositions of the present invention are administered alone or in combination with one another, or in combination with other therapeutic or in vivo diagnostic agents.

As is apparent to one skilled in the medical art, a "therapeutically effective amount" of the compounds or pharmaceutical compositions of the present invention will vary depending upon the age, weight and mammalian species treated, the particular compounds employed, the particular mode of administration and the desired affects and the therapeutic indication. Because these factors and their relationship to determining this amount are well known in the medical arts, the determination of therapeutically effective dosage levels, the amount necessary to achieve the desired result of inhibiting uPA activity, will be within the ambit of one skilled in these arts. Typically, administration of the compounds or pharmaceutical composition of the present invention is commenced at lower dosage levels, with dosage levels being increased until the desired effect of inhibiting uPA activity to the desired extent is achieved, which would define a therapeutically effective amount. For the compounds of the present invention, alone or as part of a pharmaceutical composition, such doses are between about 0.01 mg/kg and 100 mg/kg body weight, preferably between about 0.01 and 10 mg/kg, body weight.

To assist in understanding, the present invention will now be further illustrated by the following examples. These examples as they relate to this invention should not, of course, be construed as specifically limiting the invention and such variations of the invention, now known or later developed, which would be within the purview of one skilled in the art are considered to fall within the cope of the invention as described herein and hereinafter claimed.

EXAMPLES

A. Preparation Of Starting Material (See FIG. 1)

Example 1

Preparation of N-α-t-butoxycarbonyl-N$^g$-nitroargininyl-N-methoxy-N-methylamide

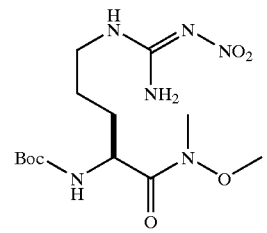

4-methylmorpholine (41.2 g, 407 mmol, 1.3 equiv.) was added to a solution of N-α-t-butoxycarbonyl-N$^g$-nitroarginine (100 g, 313 mmol), N,O-dimethylhydroxylamine hydrochloride (61.2 g, 626 mmol, 2 equiv.), EDC (77.9 g, 407 mmol, 1.3 equiv.), and 1-hydroxybenzotriazole (55.1 g, 407 mmol, 1.3 equiv.) in anhydrous acetonitrile (523 mL). The reaction was stirred at room temperature over 16 hours and solvents were removed in vacuo. The residue was partitioned between ethyl acetate and water. The aqueous phase was re-extracted with ethyl acetate (2×). The combined organic layers were washed with 1N HCl (1×), water (1×), saturated sodium bicarbonate (1×), water (1×), and then dried (magnesium sulfate), filtered, and concentrated in vacuo. The title compound was obtained in 78% mass recovery as a white foam and was used without further purification. TLC of the products indicated satisfactory purity. $R_f$=0.21 (10% methanol/dichloromethane). MS (M+H$^+$)=363.0, calculated (MW)=362.2.

$^1$H NMR (400 MHz, CDCl$_3$): d 1.47 (s, 9H), 1.55–1.68 (m, 2H), 1.71–1.83 (br, 2H), 3.23 (s, 3H), 3.25–3.35 (m, 1H), 3.55–3.68 (m, 1H), 3.75–3.80 (s, 3H), 4.66 (t, 1H), 5.63 (d, 1H).

Example 2

Preparation of N-α-t-butoxycarbonyl-N$^g$-nitro-argininal

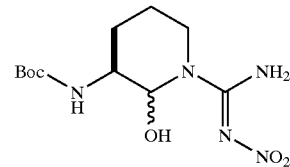

To a solution of the compound of Example 1 (25 g, 68.9 mmol, 1 equiv.), in anhydrous tetrahydrofuran (300 mL) in a 1 Liter 3-necked round bottomed flask was added dropwise 1M lithium aluminum hydride/tetrahydrofuran (100 mL, 1.45 equiv.) at −78° C. over 30 minutes under nitrogen atmosphere. The reaction was kept at −78° C. with stirring for 1 hour, and then allowed to stir at room temperature for 20 to 30 minutes. A thick slurry was observed. The reaction mixture was once again cooled to −78° C. and quenched slowly with 2M potassium bisulfate (100 mL). The precipitate was filtered out and washed with tetrahydrofuran (200 mL). The combined filtrate was concentrated in vacuo. The crude residue was partitioned with ethyl acetate and water. The organic phases were washed with 0.5 N HCl, saturated sodium bicarbonate, and brine. The residue was dried over magnesium sulfate and filtered. Evaporation of the filtrate gave 15.9 g (76% yield) of the title compound as a white solid. R$_f$=0.13 (50% hexane/ethyl acetate). The desired product was judged pure by TLC. MS: (M+H$^+$)=304.0, calculated (MW)=303.1.

$^1$H NMR (400 MHz, CDCl$_3$): d 1.47 (s, 9H), 1.55–1.68 (m, 2H), 1.71–1.83 (m, 2H), 3.19–3.35 (m, 2H), 4.41–4.48 (m, 1H), 5.82 (s, 1H).

Alternatively, the title compound can be made following the procedures set forth in Example 2 of U.S. Pat. No. 5,731,413.

Example 3

Preparation of N-α-t-butoxycarbonyl-N$^3$-nitro-argininal (6-hexanoic acid ethyl ester) cyclol

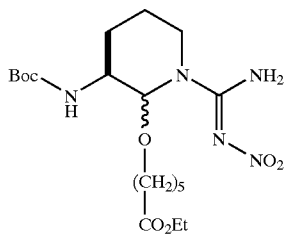

To a stirred solution of the compound of Example 2 (32.7 g, 107.9 mmol, 1 equiv.) and ethyl-6-hydroxyhexanoate (86.5 g, 539.6 mmol, 5 equiv.) in acetonitrile (20 mL), was added 3N HCl (260 µL). All the reactants went into the solution after 15 minutes at room temperature. After the mixture was stirred over 24 hours, a small aliquot was taken for TLC and Mass Spec. to determine completion. Then, acetic anhydride (55.1 g, 539.6 mmol, 5 equiv.) and pyridine (42.7 g, 539.6 mmol, 5 equiv.) were added into the reaction to cap the excess hydroxyester-linker. The reaction was allowed to continue overnight. The residue was evaporated. The residue was taken up in ethyl acetate and washed with 1N HCl (1×), water (1×), saturated sodium bicarbonate (1×), water (1×), and dried (magnesium sulfate), filtered, and concentrated. The residue was purified by flash chromatography of silica gel, using 25–33% hexane/ethyl acetate gradient and afforded 45.0 g of the title compound (93.7% yield) as a viscous oil. R$_f$=0.24 (50% hexanes/ethyl acetate). MS: (M+H$^+$)=446.0, calculated (MW)=445.2. $^1$H NMR (400 MHz, CDCl$_3$): d 1.25 (t, 3H), 1.31–1.38 (m, 2H), 1.45 (s, 9H), 1.50–1.83 (m, 8H; aliph., b, g), 2.25–2.35 (m, 2H), 2.05–3.28 (m, 1.5H), 3.30–3.45 (m, 2H), 3.55–3.65 (br, 0.5H), 3.75–3.83 (br, 1H), 4.05–4.15 (m, 2H), 4.85 (d, 1H), 5.60 (s, 1H).

Example 4

Preparation of N-α-t-butoxycarbonyl-argininal (6-hexanoic acid ethyl ester) cyclol, acetate salt

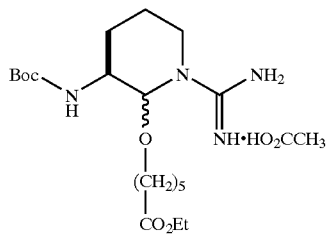

To a solution of the compound of Example 3 (45.8 g, 103.0 mmol, 1 equiv.) in ethanol/water/acetic acid (4:1:1) (200 mL) was added 10% palladium on carbon (9.2 g, 20% by weight). The mixture was hydrogenated at 40 psi for 16 hours. The solution was filtered, and the filtrate was evaporated in vacuo. The residue was taken in water and washed with ether (3×). The organic layers were re-extracted with water (1×). Aqueous phases were combined and lyophilized to afford the title compound (44.7 g, 94.4% yield). R$_f$=0.18 (dichloromethane/methanol/conc. ammonium hydroxide; 25:5:1). MS: (M+H$^+$)=401.0, calculated (MW)=400.2. $^1$H NMR (400 MHz, CDCl$_3$): d 1.25 (t, 3H), 1.31–1.38 (m, 2H), 1.45 (s, 9H), 1.50–1.83 (m, 8H; aliph., b, g), 2.25–2.35 (m, 2H), 3.05–3.28 (m, 1.5H), 3.32–3.48 (m, 2H), 3.55–3.61 (br, 0.5H), 3.63–3.73 (m, 1H), 4.08–4.15 (m, 2H), 4.89 (d, 1H), 5.14 (d, 1H).

Example 5

Preparation of N-α-t-butoxycarbonyl-N-omega-allyloxycarbonyl-argininal (6-hexanoic Acid Ethyl Ester) Cyclol

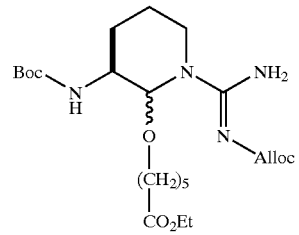

To a suspension of the compound of Example 4 (44.7 g, 97.3 mmol, 1 equiv.) in dichloromethane (292 mL) at 0° C. was added a solution of 1N sodium hydroxide (291.9 mL, 291.9 mmol, 3 equiv.) portion-wise to maintain pH=11–13. Allylchloroformate (15.3 g, 126.5 mmol, 1.3 equiv.) was added in three-portions into the reaction. After monitoring the reaction by TLC and MS for 1 hour, the mixture was extracted with dichloromethane (3×), dried (magnesium sulfate), filtered, and evaporated. The crude residue was purified immediately by flash chromatography of silica gel, using hexane and ethyl acetate as eluent. The title compound (41.5 g) was obtained (88.0% yield) as a viscous oil. R$_f$=0.30 (50% hexanes/ethyl acetate) MS: (M+H$^+$)=485.0, calculated (MW)=484.2. $^1$H NMR (400 MHz, CDCl$_3$): d 1.24 (t, 3H), 1.31–1.38 (m, 2H), 1.45 (s, 9H), 1.50–1.83 (m, 8H; aliph., b, g), 2.25–2.33 (m, 2H), 2.90–3.12 (m, 1.5H), 3.30–3.45 (m, 2H), 3.55–3.65 (br, 0.5H), 3.75–3.83 (br, 1H), 4.05–4.15 (m, 2H), 4.57 (d, 2H), 4.83 (s, 1H), 5.25 (q, 2H), 5.90–6.05 (m, 1H).

Example 6

Preparation of N-α-t-butoxycarbonyl-N-δ-Alloc-N-α-t-butoxycarbonyl-N-omega-allyloxycarbonyl-argininal (6-hexanoic Acid) Cyclol

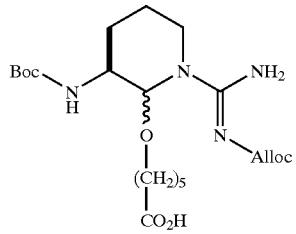

To a solution of the compound of Example 5 (40.3 g, 83.2 mmol) in ethanol (83.2 mL) was added 3N lithium hydroxide (55.5 mL, 166.4 mmol, 2 equiv.). Following stirring at room temperature for 2½ hours, the reaction mixture was concentrated in vacuo. The residue was dissolved in water and washed with ether (3×). The aqueous phase was acidified to pH=2–3 with 1N HCl and extracted with dichloromethane. The solution was dried (magnesium sulfate), filtered, and evaporated to afford 31.5 g of the title compound (83.0% yield) as a white glassy foam. $R_f$=0.33 (ethyl acetate). MS: (M+H$^+$)=457.1, calculated (MW)=456.2. $^1$H NMR (400 MHz, CDCl$_3$): d 1.45 (s, 9H), 1.52–1.87 (m, 10H; aliph., b, g), 2.32–2.43 (m, 2H), 3.05–3.28 (m, 1.5H), 3.37–3.55 (m, 2H), 3.83 (s, 1H), 4.57–4.65 (m, 2H), 4.88 (d, 1H), 5.31 (q, 2H), 5.53 (s, 1H), 5.90–6.05 (m, 1H).

Example 7

Preparation of of N-α-t-butoxycarbonyl-N-omega-allyloxycarbonyl-argininal (6-hexanoyl-aminomethylated Polystyrene Resin) Cyclol

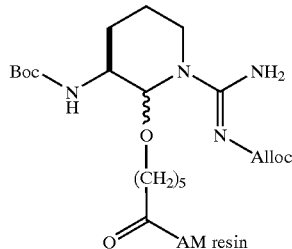

To aminomethylated polystyrene resin (22.6 g, 26.2 mmol, 1 equiv.), the compound of Example 6 (15.5 g, 34.0 mmol, 1.3 equiv.) and PyBOP (17.7 g, 34.0 mmol, 1.3 equiv.) in dimethylformamide (214 mL) at room temperature was added, followed by diisopropylethylamine (4.4 g, 34.0 mmol, 1.3 equiv.). The mixture was allowed to stir slowly in a round bottom flask overnight. The resin was washed with copious amounts of dichloromethane and methanol. The resin was dried under vacuum (a 3 mg sample of dried resin was taken out for Kaiser Test) and acetylated with dimethylformamide/acetic anhydride/triethylamine (8:1:1) for 30 minutes at ambient temperature. Once again, the resin was washed successively with organic solvents (dichloromethane and methanol), and dried under vacuum to afford the title compound (40.8 g; 92.0% yield by weight). Kaiser Test (O.D: 99% coupled); Resin substitution (approx. 0.75 mmol/g)

B. General Procedure for Solid-Phase Preparation of Smaller Quantities of Compounds Solid-phase synthesis is useful for the production of small amounts of certain compounds of the present invention. As with the conventional solid-phase synthesis of peptides, reactors for the solid-phase synthesis of peptidyl argininals are comprised of a reactor vessel with at least one surface permeable to solvent and dissolved reagents, but not permeable to synthesis resin of the selected mesh size. Such reactors include glass solid phase reaction vessels with a scintered glass frit, poylpropylene tubes or columns with frits, or reactor Kans™ made by Irori Inc., San Diego Calif. The type of reactor chosen depends on volume of solid-phase resin needed, and different reactor types might be used at different stages of a synthesis.

Example 8 describes the general procedure for solid-phase syntheses of small quantities of compounds of the present invention. See FIG. 2. Modifications of this procedure to yield additional compounds of the present invention are described in Examples 9 to 15.

Example 8

Solid-Phase Synthesis of isobutyloxycarbonyl-D-seryl-L-alanyl-argininal (Compound 1)

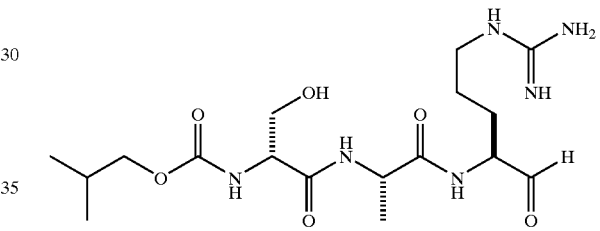

Step 1: Preparation of N-omega-allyloxycarbonyl-argininal (6-hexanoyl-aminomethylated polystyrene resin) cyclol

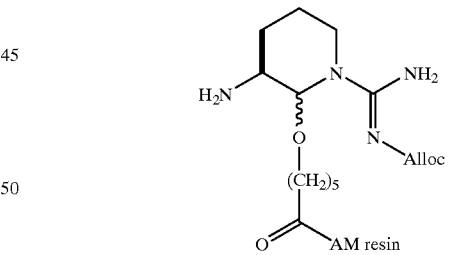

To a 60 mL solid phase reaction vessel was added 2.0 g of the compound of Example 7 (0.6–0.7 meq/g substitution), and a mixture of dichloromethane (12 mL), trifluoroacetic acid (6 mL), and thioanisole (2 mL). Nitrogen gas was bubbled for 15 minutes. The reactants were drained from the resin and the resin was washed successively with dichloromethane(2×20 mL), diisopropylethylamine (20 mL), dichloromethane (2×20 mL), diisopropylethylamine (20 mL), dichloromethane (2×20 mL), and diethyl ether (2×20 mL). The title compound was stored under vacuum. A ninhydrin test of the resin showed a dark blue color characteristic of the free amine produced by the removal of the t-t-butoxycarbonyl group.

Step 2: Preparation of N-α-Fmoc-alanyl-N-omega-allyloxycarbonyl-argininal (6-hexanoyl-aminomethylated polystyrene resin) cyclol

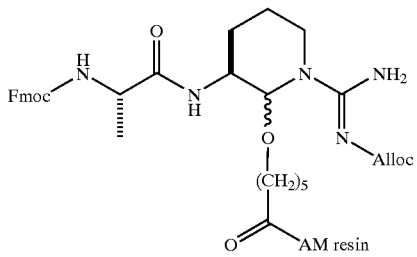

The compound of Step 1 (2.1 g) was placed in a solid phase reaction vessel to which were added Fmoc-alanine (1 g, 3.2 mmol), 1-hydroxybenzotriazole (0.5 g, 3.2 mmol), TBTU (1.024 g, 3.2 mmol) and diisopropylethylamine (600 μL, 3.4 mmol) in dimethylformamide (15–20 mL). Nitrogen gas was bubbled through the reactor at room temperature for 2 hours. The reagents were drained from the resin and the resin was washed successively with dimethylformamide (2×20 mL), dichloromethane (2×20 mL), dimethylformamide (2×20 mL), dichloromethane (2×20 mL), and diethyl ether (2×20 mL). The resin was vacuum dried and a small aliquot was taken for ninhydrin calorimetric analysis, which showed a 99.5% coupling efficiency in the production the title compound.

Step 3: Preparation of alanyl-N-omega-allyloxycarbonyl-argininal (6-hexanoyl-aminomethylated polystyrene resin) cyclol

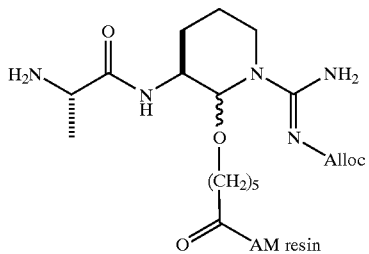

The compound of Step 2 was treated with 50% piperidine in dimethylformamide (20 mL) for 30 minutes at room temperature with nitrogen gas agitation. The resin was washed as above and vacuum dried to give the title compound. A ninhydrin assay on a small aliquot gave dark blue resin and solution showing a high yield for the deprotection.

Step 4: N-α-Fmoc-D-seryl(O-t-butyl)-alanyl-N-omega-allyloxycarbonyl-argininal (6-hexanoyl-aminomethylated polystyrene resin) cyclol

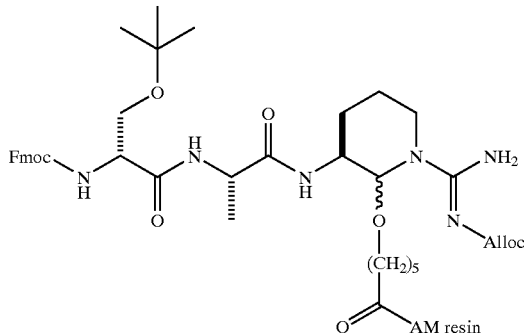

The compound of Step 3 (100 mg) was placed in an Irori Kan™ reaction vessel. The vessel was placed in a 20 mL vial containing dimethylformamide (4 mL), N-α-Fmoc-D-serine (O-t-butyl) (184 mg, 0.48 mmol), 1-hydroxybenzotriazole (73 mg, 0.48 mmol), TBTU (154 mg, 0.48 mmol), and diisopropylethylamine (84 μl, 0.48 mmol). The vessel was agitated for 3 hours on a shaker table. The vessel was drained, washed successively with dimethylformamide (2×3 mL), dichloromethane(2×3 mL), dimethylformamide(2×3 mL), dichloromethane(2×3 mL), isopropanol(2×3 mL), dichloromethane(2×3 mL), isopropanol(2×3 mL), and diethyl ether(2×3 mL). The resin was dried under vacuum to give the title compound.

Step 5: D-seryl(O-t-butyl)-alanyl-N-omega-allyloxycarbonyl-argininal (6-hexanoyl-aminomethylated polystyrene resin) cyclol

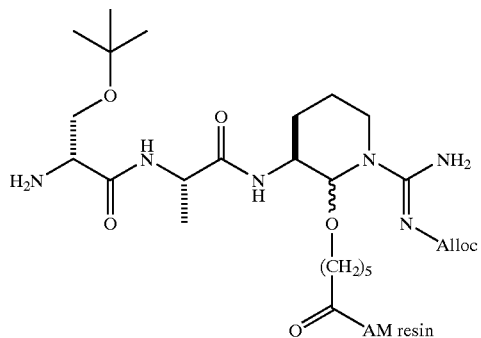

The vessel containing the compound of Step 4 was treated with 50% piperidine in dimethylformamide (5 mL) in a 20 mL vial for 45 minutes at room temperature while agitated on a shaker table. The resin was washed as above and vacuum dried to give the compound of Step 5. A ninhydrin assay on a small aliquot gave a dark blue resin and solution indicating a high yield for the deprotection.

Step 6: carbamate analogs of D-seryl(O-t-butyl)-alanyl-N-omega-allyloxycarbonyl-argininal (6-hexanoyl-aminomethylated polystyrene resin) cyclol such as

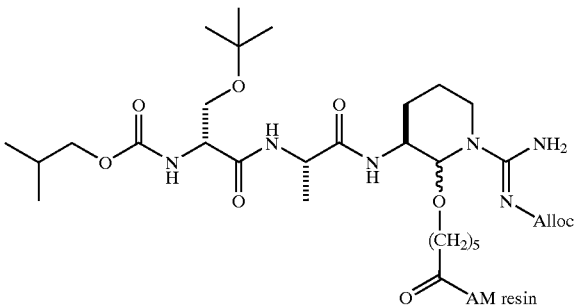

The vessel containing the compounds of Step 5, along with other vessels containing related resin-bound analogs (see Examples 9 to 14, below), were/are each placed in a 20 mL vial with 0.12M various individual chloroformates, including isobutylchloroformate, in dimethylformamide (5–10 mL). Diisopropylethylamine (105–210 μL, 0.6–1.2 mmol) was/is added, and the vials were/are shaken for 2.5 hours. All vessels are drained and washed successively with dimethylformamide(2×3 mL), dichloromethane(2×3 mL), dimethylformamide(2×3 mL), dichloromethane(2×3 mL), isopropanol(2×3 mL), dichloromethane(2×3 mL), isopropanol(2×3 mL), and diethyl ether(2×3 mL). The Kans™ were/are vacuum dried, including the one containing isobutyloxycarbonyl-D-seryl(O-t-butyl)-alanyl-N-ω-allyloxycarbonyl-argininal (6-hexanoyl-aminomethylated polystyrene resin) cyclol.

Step 7: carbamate analogs of D-seryl(O-t-butyl)-alanyl-argininal (6-hexanoyl-aminomethylated polystyrene resin) cyclol such as

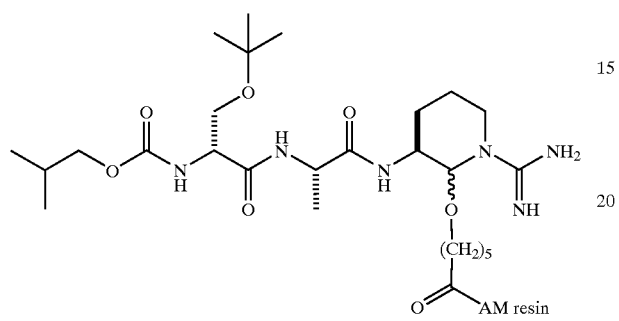

Removal of the allyloxy protecting group from the products of Step 5 was/is accomplished for several compounds of the present invention simultaneously by placing a collection of 38 vessels in a 250 mL polypropylene bottle and adding a mixture of methylsulfoxide (10 mL), tetrahydrofuran (10 mL), 1N HCl (2.5 mL), and morpholine (25 mL). Tetrakis triphenylphosphine palladium (0.87 g) was/is then added, and the bottle was/is shaken for 4 hours at room temperature. The vessels, including the one containing containing isobutyloxycarbonyl-D-seryl(O-t-butyl)-alanyl-argininal (6-hexanoyl-aminomethylated polystyrene resin) cyclol, were/are drained, washed successively with dimethylformamide(2×3 mL), dichloromethane(2×3 mL), dimethylformamide(2×3 mL), dichloromethane(2×3mL), isopropanol(2×3 mL), dichloromethane(2×3 mL), isopropanol(2×3 mL), and diethyl ether(2×3 mL), and vacuum dried to give individual title compounds in vessels.

Step 8: isobutyloxycarbonyl-D-seryl-alanyl-argininal

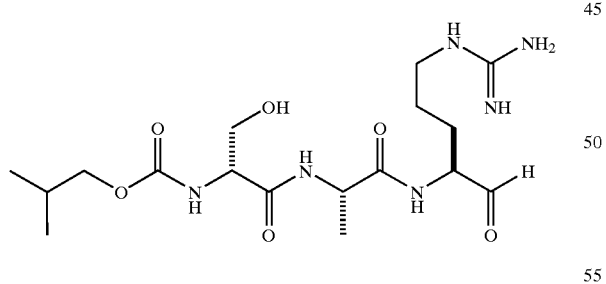

The vessel containing isobutyloxycarbonyl-D-seryl(O-t-butyl)-alanyl-argininal (6-hexanoyl-aminomethylated polystyrene resin) cyclol was emptied into a Whatman polypropylene mini-column containing trifluoroacetic acid/dichloromethane/water (1.5 mL of a 6:3:1 mixture). The column was shaken for 4 hours at room temperature. The reaction solution was drained into a test tube and the resin was washed with dichloromethane and water. The wash mixtures and the reaction mixtures were collected in the same test tube, and the mixture was agitated, then allowed to separate into two phases. The water layer was removed and filtered. The title compound (compound 1) was purified by semipreparative reverse-phase HPLC, lyophilized, and weighed, and analyzed by HPLC and mass spectrometry. An alternate route to synthesis of compound 1 is provided in Examples 35 to 40.

Example 9

Solid-phase Synthesis of benzyloxycarbonyl-D-seryl-alanyl-argininal (Compound 2)

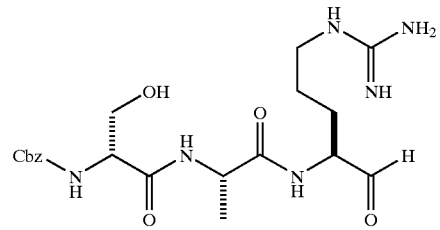

Steps 1 through 4 and 7 through 8 of Example 8 are followed to make benzyloxycarbonyl-D-seryl-alanyl-argininal, compound 2, with the substitution in Step 4 of Cbz-D-serine (O-t-butyl) for Fmoc-D-serine(O-t-butyl).

Example 10

Solid-phase Synthesis of Compounds 3 to 9 and 35 to 40

Steps 1 through 8 of Example 8 are followed to make the following compounds, with the noted substitution for isobutylchloroformate in Step 6:

| COMPOUND NUMBER | COMPOUND NAME | SUBSTITUTION IN STEP 6 |
|---|---|---|
| 3 | (−)menthyloxy-carbonyl-D-seryl-alanyl-argininal | (−)menthylchloroformate |
| 4 | 2-naphthyloxy-carbonyl-D-seryl-alanyl-argininal | 2-naphthylchloroformate |
| 5 | phenoxycarbonyl-D-seryl-alanyl-argininal | phenylchloroformate |
| 6 | 2-ethylhexyloxy-carbonyl-D-seryl-alanyl-argininal | 2-ethylhexylchloroformate |
| 7 | (+)menthyloxy-carbonyl-D-seryl-alanyl-argininal | (+)menthylchloroformate |
| 8 | methyloxycarbonyl-D-seryl-alanyl-argininal | methylchloroformate |
| 9 | n-butyloxycarbonyl-D-seryl-alanyl-argininal | n-butylchloroformate |
| 35 | 3-cyclohexylpropionyl-D-seryl-alanyl-argininal | 3-cyclohexylpropionyl chloride |
| 36 | cyclohexylmethyloxycarbonyl-D-seryl-alanyl-argininal | cyclohexylmethyl chloroformate |
| 37 | cyclohexylmethylazacarbonyl-D-seryl-alanyl-argininal | cyclohexylmethyl isocyanate |
| 38 | benzylazacarbonyl-D-seryl-alanyl-argininal | benzyl isocyanate |
| 39 | isovaleryl-D-seryl-alanyl-argininal | isovaleryl chloride |
| 40 | isopropyloxycarbonyl-D-seryl-alanyl-argininal | isopropyl chloroformate |

Example 11

Solid-phase Synthesis of fluorenylmethyloxycarbonyl-D-seryl-alanyl-argininal (Compound 10)

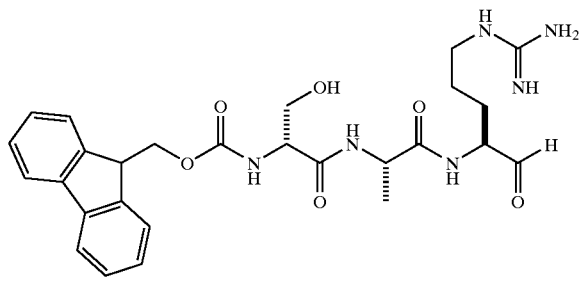

Steps 1 through 4 and Steps 7 and 8 of Example 8 are followed to make fluorenylmethyloxycarbonyl-D-seryl-alanyl-argininal, compound 10.

Example 12

Solid-phase Synthesis of Compounds 11 to 18

Steps 1 through 4 and 7 through 8 of Example 8 are followed to make compounds 11 to 18, with the substitution in Step 4 of Cbz-D-serine(O-t-butyl) Fmoc-D-serine(O-t-butyl), and the noted substitution in Step 2 for Fmoc-alanine.

| COMPOUND NUMBER | COMPOUND NAME | SUBSTITUTION IN STEP 2 |
|---|---|---|
| 11 | benzyloxycarbonyl-D-seryl-prolyl-argininal | Fmoc-proline |
| 12 | benzyloxycarbonyl-D-seryl-L-azetidine-2-carbonyl-argininal | Fmoc-L-azetidine-2-carbocylic acid |
| 13 | benzyloxycarbonyl-D-seryl-pipecolyl-argininal | Fmoc-pipecolic acid |
| 14 | benzyloxycarbonyl-D-seryl-2-aminobutanoyl-argininal | Fmoc-2-aminobutanoic acid |
| 15 | benzyloxycarbonyl-D-seryl-S-methylcysteinyl-argininal | Fmoc-S-methylcysteine |
| 16 | benzyloxycarbonyl-D-seryl-2-norvalyl-argininal | Fmoc-norvaline |
| 17 | benzyloxycarbonyl-D-seryl-2-glycyl-argininal | Fmoc-glycine |
| 18 | benzyloxycarbonyl-D-seryl-sarcosyl-argininal | Fmoc-sarcosine |

Example 13

Solid-phase Synthesis of Compounds 19 to 23

Steps 1 through 4 and Steps 7 through 8 of Example 8 are followed to make compounds 19 to 23, with the noted substitution in Step 4 for Fmoc-D-serine(O-t-butyl).

| COMPOUND NUMBER | COMPOUND NAME | SUBSTITUTION IN STEP 4 |
|---|---|---|
| 19 | benzyloxycarbonyl-D-allothreonyl-alanyl-argininal | Cbz-D-allothreonine (O-t-butyl) |
| 20 | benzyloxycarbonyl-threonyl-alanyl-argininal | Cbz-threonine (O-t-butyl) |
| 21 | benzyloxycarbonyl-D-alanyl-alanyl-argininal | Cbz-D-alanine |
| 22 | benzyloxycarbonyl-D-threonyl-alanyl-argininal | Cbz-D-threonine (O-t-butyl) |
| 23 | benzyloxycarbonyl-seryl-alanyl-argininal | Cbz-serine (O-t-butyl) |

Example 14

Solid-phase Synthesis of Compounds 24, 25, and 33

Steps 1 through 4 and 7 through 8 of Example 8 are followed to make compounds 24, 25, and 33 with the substitution in Step 4 of Cbz-D-allothreonine(O-t-butyl) for Fmoc-D-serine(O-t-butyl), and the noted substitution in Step 2 for Fmoc-alanine.

| COMPOUND NUMBER | COMPOUND NAME | SUBSTITUTION IN STEP 2 |
|---|---|---|
| 24 | benzyloxycarbonyl-D-allothreonyl-sarcosyl-argininal | Fmoc-sarcosine |
| 25 | benzyloxycarbonyl-D-allothreonyl-N-methylalanyl-argininal | Fmoc-N-methylalanine |

Example 15

Solid-phase Synthesis of Compounds 26 to 27

Steps 1 through 4 and 7 through 8 of Example 8 are followed to make compounds 26 to 27, with the substitution in Step 2 of Fmoc-proline for Fmoc-alanine, and the noted substitution in Step 3 for Fmoc-D-serine(O-t-butyl).

| COMPOUND NUMBER | COMPOUND NAME | SUBSTITUTION IN STEP 4 |
|---|---|---|
| 26 | benzyloxycarbonyl-D-threonyl-prolyl-argininal | Cbz-D-threonine(O-t-butyl) |
| 27 | benzyloxycarbonyl-D-homoseryl-prolyl-argininal | Cbz-D-homoserine (O-t-butyl) |

Example 16

Solid-phase Synthesis of Compounds 41 to 43

Steps 1 through 4 and 7 through 8 of Example 8 are followed to make compounds 41 to 43, with the substitution in Step 4 of N-α-Cbz-N-β-Fmoc-D-2,3-diaminopropionic acid for for Fmoc-D-serine(O-t-butyl), and the noted substitution in Step 6 for the individual chloroformates:

| COMPOUND NUMBER | COMPOUND NAME | SUBSTITUTION IN STEP 6 |
|---|---|---|
| 41 | N-α-benzyloxycarbonyl-N-β-2-phenylethylcarbonyl-D-2,3-diaminopropionyl-alanyl-argininal | hydrocinnamoyl chloride |
| 42 | N-α-N-β-dibenzyloxycarbonyl-D-2,3-diaminopropionyl-alanyl-argininal | benzyl chloroformate |
| 43 | N-α-benzyloxycarbonyl-N-β-methyloxycarbonyl-D-2,3-diaminopropionyl-alanyl-argininal | methyl chloroformate |

C. Alternate Synthetic Routes for Certain Compounds (i) Examples 17 to 21 describe the synthesis of benzenesufonyl-D-Ser-L-Ala-L-Arg-al, trifluoroacetate salt (compound 28) See FIG. 3.

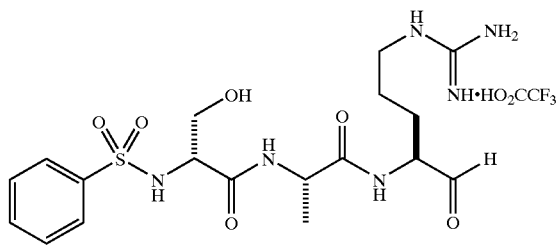

Example 17

Synthesis of D-Ser(O-t-Bu)-Ala-OMe, Acetate Salt

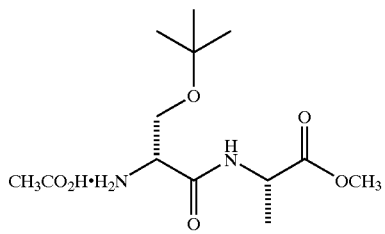

N-α-Cbz-D-serine (Bachem, 4.97 g, 16.8 mmol), alanine methyl ester, hydrochloride salt (Novabiochem, 4.7 g, 33.7 mmol), EDC (6.5 g, 33.7 mmol), and 1-hydroxybenzotriazole (2.6 g, 16.8 mmol) were combined, and acetonitrile (67 mL) was added. After stirring as a slurry for 10 minutes, diisopropylethylamine (14.4 mL, 84 mmol) was added, and the resulting clear mixture was stirred for an additional 18 hours. The solvent was removed under reduced pressure, and the residue was suspended in ethyl acetate (500 mL). The solution was washed with 0.5M HCl (2×100 mL), followed by saturated sodium bicarbonate (2×100 mL), and brine (100 mL). The organic layer was then dried with sodium sulfate, and the solvent was removed in vacuo to afford Cbz-D-Ser(O-t-Bu)-Ala-OMe in a quantitative yield as a single peak by reverse-phase (C18) HPLC $t_R$=16.9 at 0.1% trifluoroacetic acid in 5–75% aqueous acetonitrile over 20 minutes. Cbz-D-Ser(O-t-Bu)-Ala-OMe was then dissolved in ethanol/acetic acid/water (150 mL of a 4:1:1 mixture). The flask was charged with nitrogen, and 10% palladium on carbon (1.5 g) was added. This mixture was hydrogenated at 45 psi for 2 hours. The palladium catalyst was filtered, and solvent removed under reduced pressure to give 4.58 g of the title compound in a 95% yield as a single peak by reverse-phase (C18) HPLC ($t_R$=8.0 minutes at 0.1% trifluoroacetic acid in 5–75% aqueous acetonitrile over 20 minutes), and MS (M+H=247.2).

Example 18

Synthesis of benzenesufonyl-D-Ser(O-t-Bu)-Ala-OMe

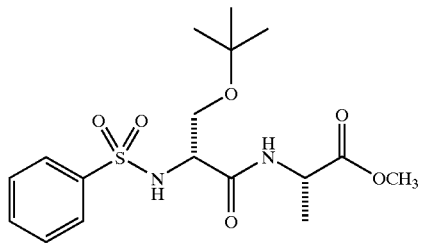

To a stirred slurry of the compound of Example 17 (1.0 g, 3.3 mmol) in acetonitrile (13 mL) was added benzenesufonyl chloride (0.87 g, 4.9 mmol). To this mixture diisopropylethylamine(1.67 mL,9.8 mmol) was added in five portions over a 1 hour period. The mixture was allowed to stir an additional hour. The solvent was removed under reduced pressure, and the residue was suspended in ethyl acetate (100 mL). The solution was washed with 0.5M HCl (2×10 mL), followed by saturated sodium bicarbonate (2×10 mL), and brine (1×10 mL). The organic layer was then dried with sodium sulfate, and solvent was removed under reduced pressure. The residue was purified by flash chromatography eluting with 50% hexanes/ethyl acetate, yielding 0.54 g, 1.4 mmol, of product in a 43% yield. The product was a single peak by reverse phase (C18) HPLC ($t_R$=20.2 minutes at 0.1% trifluoroacetic acid in 5–75% aqueous acetonitrile over 20 minutes). $^1$H NMR(CD$_3$OD): 7.5–7.9 ppm(m,5H), 4.3 ppm(q,1H), 3.9 ppm(t,1H), 3.7(s,3H), 3.4 ppm(m,1H),3.5 ppm(m,1H), 1.3 ppm(d,3H), 1.05 ppm(s, 9H).

Example 19

Synthesis of benzenesufonyl-D-Ser(O-t-Bu)-Ala-OH

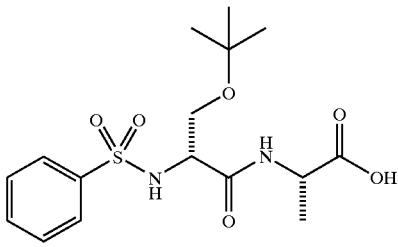

To the compound of Example 18 (0.53 g, 1.4 mmol) in methanol (9 mL) was added 1.0M lithium hydroxide (3.0 mL, 3 mmol). After stirring for 18 hours, the reaction mixture was poured over a column of 10 mL of DOWEX (50×8–400) ion exchange resin, and eluted with methanol/water (60 mL of a 1:1 mixture). The methanol was pumped off under reduced pressure and the remaining water was lyophilized, yielding 0.49 g, 1.3 mmol (95%) of the title compound as a single peak by reverse-phase (C18) HPLC ($t_R$=13.5 minutes at 0.1% trifluoroacetic acid in 5–75% aqueous acetonitrile over 20 minutes). $^1$H NMR(CD$_3$OD): 7.9 ppm(d,2H), 7.6 ppm(t,1H), 7.5 ppm(t,2H), 4.25 ppm(q, 1H), 3.9(t,1H), 3.5 ppm(m,1H), 3.4 ppm(m,1H),1.3 ppm(d, 3H), 1.075 ppm(s,9H).

Example 20

Synthesis of benzenesufonyl-D-Ser(O-t-Bu)-Ala-N$^g$-nitroargininal Ethyl Cyclol

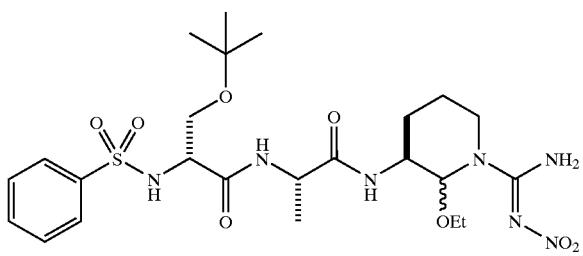

The compound of Example 19 (0.48 g, 1.3 mmol), L-N$^g$-nitroargininal ethyl cyclol, hydrochloride salt (0.41 g, 1.5 mmol), EDC (0.37 g, 1.9 mmol), and 1-hydroxybenzotriazole (0.20 g, 1.3 mmol) were combined and acetonitrile (5 mL) was added. After stirring the resulting slurry for 10 minutes, diisopropylethylamine (1.10 mL, 84 mmol) was added and the resulting clear mixture was stirred for an additional 18 hours. The solvent was removed under reduced pressure, and the residue was suspended in ethyl acetate (100 mL). The solution was washed with 0.5M HCl (2×10 mL), followed by saturated sodium bicarbonate (2×10 mL), and brine (1×10 mL). The organic layer was dried with sodium sulfate, and solvent was removed in vacuo to afford 0.72 g the title compound in 95% yield. The product was a single peak by reverse phase (C18) HPLC ($t_R$=15.2 minutes at 0.1% trifluoroacetic acid in 5–75% aqueous acetonitrile over 20 minutes), with MS(M+H=371).

Example 21

Synthesis of benzenesufonyl-D-Ser-L-Ala-L-Arg-al, Trifluoroacetate Salt (Compound 28)

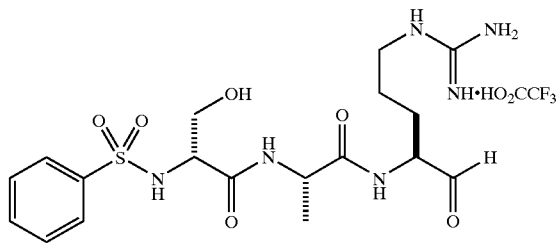

The compound of Example 20 (0.72 g, 1.23 mmol) was hydrogenated over 10% palladium on carbon (250 mg) in ethanol/acetic acid/water (24.5 mL of 4:1:1 mixture) at 50 psi for 18 hours. The catalyst was filtered, and the solvent was removed from the filtrate in vacuo to give a quantitative yield of benzylsufonyl-D-Ser(O-t-Bu)-L-Ala-L-argininal ethyl cyclol as a single peak by reverse-phase (C18) HPLC ($t_R$=12.8 minutes at 0.1% trifluoroacetic acid in 5–75% aqueous acetonitrile over 20 minutes), and MS(M+H=541).

Benzylsufonyl-D-Ser(O-t-Bu)-L-Ala-L-argininal ethyl cyclol was treated with 6M HCl (12.25 mL), stirred for 1 hour, then neutralized with 6.5M ammonium acetate to pH 4. This material was loaded directly onto a preparative HPLC column and eluted with a 0–20% aqueous acetonitrile gradient to afford 88 mg of the title compound in a 15% yield after lyophilization. The title compound had three peaks by reverse-phase (C18) HPLC ($t_R$=8.2 minutes, 9.2 minutes, and 9.5 minutes at 0.1% trifluoroacetic acid in 5–50% aqueous acetonitrile over 20 minutes), with MS(M+H=457).

(ii) Examples 22 to 26 describe the synthesis of benzylsulfonyl-D-Ser-L-Ala-L-Arg-al, trifluoroacetate salt (compound 29).

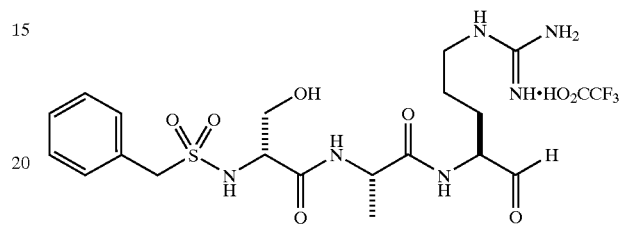

Example 22

Synthesis of benzylsulfonyl-D-Ser(O-t-Bu)-OMe

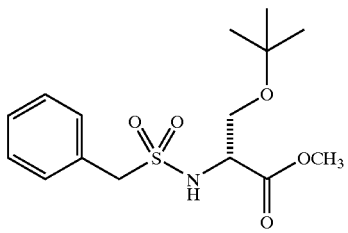

To a stirred solution of D-serine(O-t-Bu) methyl ester, hydrochloride salt (2.07 g, 9.8 mmol) in acetonitrile (39 mL) was added α-toluenesulfonyl chloride (1.86 g, 9.8 mmol). To this mixture of diisopropylethylamine (3.7 mL, 21.5 mmol) were added in five portions over a 1 hour period. The mixture was allowed to stir an additional hour. The solvent was removed under reduced pressure, and the residue was suspended in ethyl acetate (100 mL). The solution was washed with 0.5M HCl (2×10 mL), followed by saturated sodium bicarbonate (2×10 mL), and brine (1×10 mL). The organic layer was dried with sodium sulfate, and solvent was removed in vacuo to give 2.84 g of the title compound in 88% yield. $R_f$=0.04 (4:1 ethyl acetate:hexanes).

Example 23

Synthesis of benzylsulfonyl-D-Ser(O-t-Bu)-OH

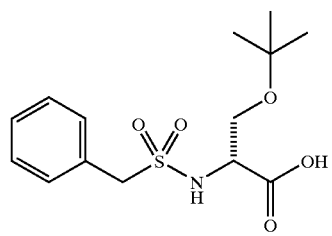

To a stirred solution of the compound of Example 22 (2.66 g, 8.1 mmol) in methanol (54 mL) was added 1.0M lithium hydroxide (17.8 mL, 17.8 mmol). The reaction mixture was allowed to stir for 18 hours, then poured over a column of 10 mL of DOWEX(50 X 8-400) ion exchange resin and eluted with methanol:water (60 mL of a 1:1 mixture). The methanol was removed under reduced pressure, and the remaining aqueous solution was lyophilized to afford 2.47 g of the title compound in 97% yield. $t_R$=14.8 minutes (0.1% trifluoroacetic acid in 5–75% aqueous acetonitrile over 20 minutes).

Example 24

Synthesis of benzylsulfonyl-D-Ser(O-t-Bu)-Ala-OMe

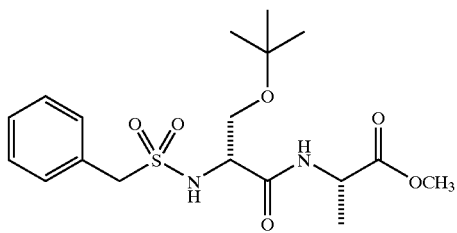

The compound of Example 23 (1.0 g, 3.2 mmol), alanine methyl ester, hydrochloride salt (Novabiochem, 0.89 g, 6.3 mmol), EDC (1.22 g, 6.3 mmol), and 1-hydroxybenzotriazole (0.49 g, 3.2 mmol) were combined and acetonitrile (13 mL) was added. After stirring the resulting slurry for 10 minutes, diisopropylethylamine (2.71 mL, 15.8 mmol) was added and the resulting clear mixture was stirred for an additional 18 hours. The solvent was removed under reduced pressure, and the residue was suspended in ethyl acetate (100 mL). The solution was washed with 0.5M HCl (2×10 mL), followed by saturated sodium bicarbonate (2×10 mL), and brine (1×10 mL). The organic layer was then dried with sodium sulfate, and solvent was removed in vacuo to afford 1.22 g of the title compound in 97% yield. $t_R$=16.2 minutes (0.1% trifluoroacetic acid in 5–7.5% aqueous acetonitrile over 20 minutes).

Example 25

Synthesis of benzylsulfonyl-D-Ser(O-t-Bu)-Ala-OH

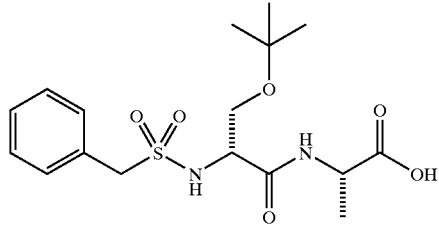

To the compound of Example 24 (1.22 g, 3.1 mmol) in methanol (22 mL) was added 1M lithium hydroxide (7.2 mL, 7.2 mmol). After stirring 18 hours, the reaction mixture was poured over a column of 10 mL of DOWEX(50 X 8-400) ion exchange resin and eluted with methanol:water (60 mL of a 1:1 mixture). The methanol was removed under reduced pressure, and the aqueous solution was lyophilized to afford 1.16 g of the title compound in 91% yield. $t_R$=13.2 minutes (0.1% trifluoroacetic acid in 5–75% aqueous acetonitrile over 20 minutes).

Example 26

Synthesis of benzylsulfonyl-D-Ser-Ala-Arg-al, Trifluoroacetate Salt (Compound 29)

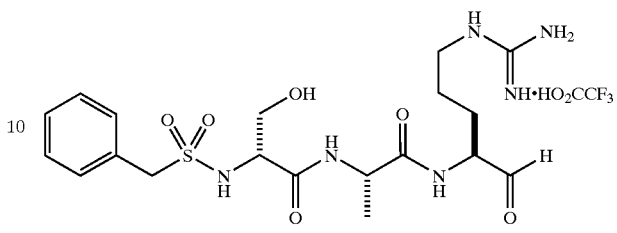

The title compound was synthesized from the compound of Example 25 following the procedures of Examples 20 and 21, with the compound of Example 25 replacing the compound of Example 19 in the procedure described in Example 20.

(iii) Examples 27 to 34 describe the synthesis of i-butoxycarbonyl-D-Ser-Ala-Arg-CO-phenethylamide, trifluoroacetate salt (compound 30). See FIG. 4.

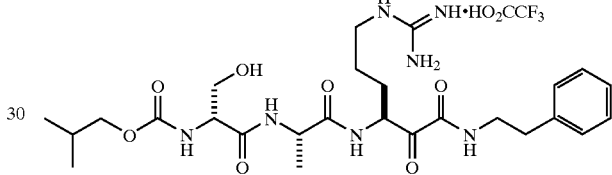

Example 27

Synthesis of N-α-t-butoxycarbonyl-$N^g$-nitroArg-COH-phenethylamide

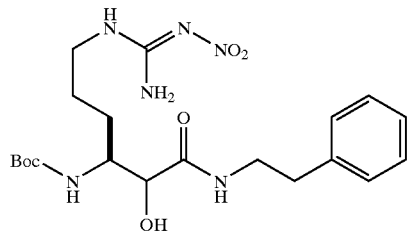

N-α-t-butoxycarbonyl-$N^g$-nitroArg-COH-COOH (1.07 g, 3 mmol) (prepared following the procedure in U.S. Pat. No. 5,371,072, Examples 2 to 5), phenethylamine (38 mL, 3 mmol), BOP (1.35 g, 3 mmol), and 1-hydroxybenzotriazole (0.23 g, 1.5 mmol) were combined and dimethylformamide (122 mL) was added. This mixture was stirred for 10 minutes followed by addition of 4-methylmorpholine (2.01 mL, 18 mmol), and the resulting clear mixture was stirred for an additional 18 hours. The solvent was removed under reduced pressure, and the residue was suspended in 100 mL of ethyl acetate. The solution was washed with 0.5M HCl (2×10 mL), followed by saturated sodium bicarbonate (2×10 mL), and brine(1×10 mL). The organic layer was then dried with sodium sulfate, and solvent was removed under reduced pressure. The residue was purified by flash chromatography eluting with ethyl acetate:hexanes (4:1) to afford 1.22 g of the title compound in 89% yield. $t_R$=13.2 minutes and 14.1 minutes (0.1% trifluoroacetic acid in 5–75% aqueous acetonitrile over 20 minutes).

Example 28

Synthesis of t-butoxycarbonyl-Ala-N$^g$-nitroArg-COH-phenethylamide

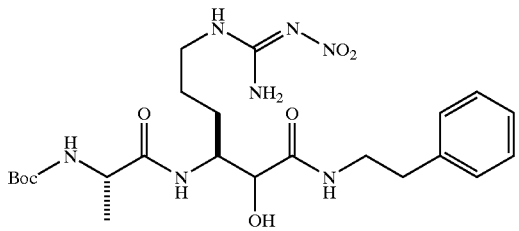

To a stirred solution of the compound of Example 27 (1.22 g, 2.7 mmol) in ethyl acetate (10 mL) was added 5M HCl in ethyl acetate (10 mL). After 2 hours the solid that formed was filtered, dried to give quantitative yields N$^g$-nitroArg-COH-phenethylamide, hydrochloride salt, which was combined with t-butoxycarbonyl-Ala-OH (Novabiochem, 0.77 g, 4.1 mmol), EDC (2.4 g, 5.4 mmol), and 1-hydroxybenzotriazole (0.42 g, 2.7 mmol), and acetonitrile (11 mL) was added. This mixture was stirred as a slurry for 10 minutes, and diisopropylethylamine (2.3 mL, 13.55 mmol) was added. The resulting clear mixture was stirred for an additional 18 hours. The solvent was removed under reduced pressure, and the residue was suspended in ethyl acetate (100 mL). The solution was washed with 0.5M HCl (2×10 mL), followed by saturated sodium bicarbonate (2×10 mL), and brine (1×10 mL). The organic layer was then dried with sodium sulfate, and solvent was removed in vacuo to afford 1.34 g of the title compound in a 95% yield. $t_R$=13.0 minutes and 13.6 minutes (0.1% trifluoroacetic acid in 5–75% aqueous acetonitrile over 20 minutes).

Example 29

Synthesis of HCl-Ala-N$^g$-nitroArg-COH-phenethylamide

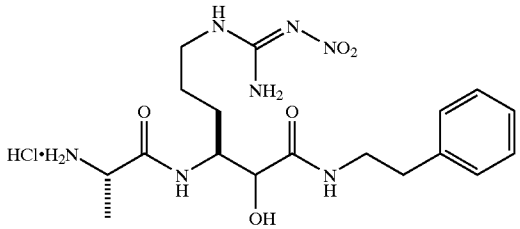

The compound of Example 28 (1.34 g, 2.6 mmol) was dissolved in 10 mL of ethyl acetate. To this 10 mL of 5M HCl in ethyl acetate were added and the mixture stirred. After 2 hours the solid that formed was filtered and dried to give 1.188 g of the title compound in 98% yield.

Example 30

Synthesis of t-butoxycarbonyl-D-Ser(OBn)-Ala-N$^g$-nitroArg-COH-phenethylamide

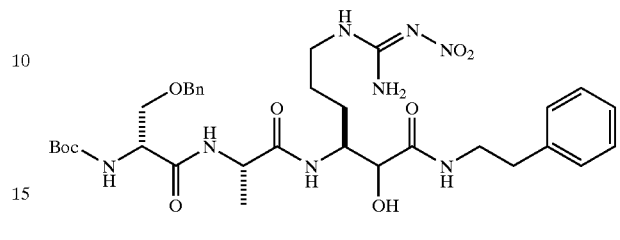

The compound of Example 29 (1.18 g, 2.4 mmol), t-butoxycarbonyl-D-serine benzylester (Novabiochem, 1.08 g, 3.6 mmol), EDC (2.15 g, 4.9 mmol), and 1-hydroxybenzotriazole (0.37 g, 2.4 mmol) were combined, and acetonitrile (10 mL) was added. To this slurry was added diisopropylethylamine (2.1 mL, 15 mmol) over a 10 minute period, and the resulting clear mixture was stirred for an additional 18 hours. The solvent was removed under reduced pressure, and the residue was suspended in ethyl acetate (100 mL). The solution was washed with 0.5M HCl (2×10 mL), followed by saturated sodium bicarbonate (2×10 mL), and brine (1×10 mL). The organic layer was then dried with sodium sulfate, and solvent was removed in vacuo to afford 1.56 g of the title compound in 92% yield. $t_R$=16.0 minutes and 16.5 minutes (0.1% trifluoroacetic acid in 5–75% aqueous acetonitrile over 20 minutes).

Example 31

Synthesis of HCl-D-Ser (OBn)-Ala-N$^g$-nitroArg-COH-phenethylamide

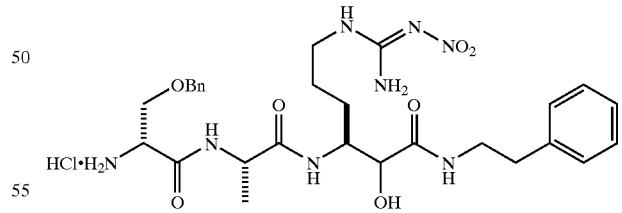

To a solution of the compound of Example 30 (1.5 g, 2.1 mmol) in ethyl acetate (10 mL) was added 5M HCl in ethyl acetate (10 mL). After stirring 2 hours, the solid that formed was filtered and dried to give 1.31 g of the title compound in 98% yield. $t_R$=11.8 minutes and 12.3 minutes at 0.1% trifluoroacetic acid in 5–75% aqueous acetonitrile over 20 minutes.

Example 32

Synthesis of i-butoxycarbonyl-D-Ser(OBn)-Ala-N$^g$-nitroArg-COH-phenethylamide

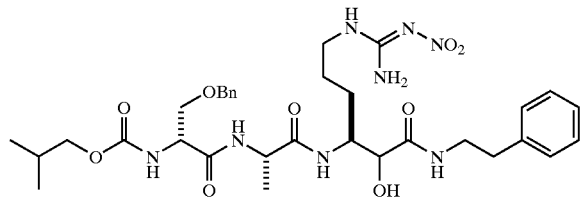

To a stirred solution of the compound of Example 31 (1.0 g, 1.6 mmol) in acetonitrile (6 mL) was added isobutylchloroformate (0.225 mL, 1.8 mmol), followed by diisopropylethylamine (0.81 mL, 4.74 mmol) and this mixture was stirred for 2 hours. The solvent was removed under reduced pressure, and the residue was suspended in ethyl acetate (100 mL). The solution was washed with 0.5M HCl (2×10 mL), followed by saturated sodium bicarbonate (2×10 mL), and brine (1×10 mL). The organic layer was then dried with sodium sulfate, and solvent was removed under reduced pressure. The residue was purified by flash chromatography eluting with ethyl acetate/hexanes (4:1) to afford 0.94 g of the title compound in 85% yield. $t_R$=20.2 minutes and 21.2 minutes (0.1% trifluoroacetic acid in 25–45% aqueous acetonitrile over 20 minutes).

Example 33

Synthesis of i-butoxycarbonyl-D-Ser(OBn)-Ala-N$^g$-nitroArg-CO-phenethylamide

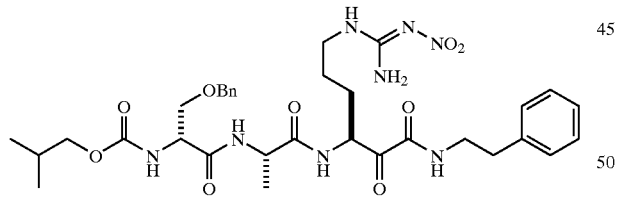

The compound of Example 32 (0.1 g, 0.143 mmol) was dissolved in DMSO (1.4 mL). EDC (0.14 g, 0.714 mmol) and dichloroacetic acid (0.12 mL, 1.43 mmol) were added, and the mixture stirred for 1 hour. The reaction mixture was then poured into ethyl acetate (50 mL) and washed with 0.5M HCl (2×10 mL), followed by saturated sodium bicarbonate (2×10 mL), and brine (1×10 mL). The organic layer was then dried with sodium sulfate, and solvent was removed under reduced pressure. The residue was purified by flash chromatography eluting with ethyl acetate/hexanes (4:1) to afford 68 mg of the title compound in 68% yield. $R_f$=0.32 (4:1 ethyl acetate/hexanes)

Example 34

Synthesis of i-butoxycarbonyl-D-Ser-Ala-Arg-CO-phenethylamide, Trifluoroacetate Salt

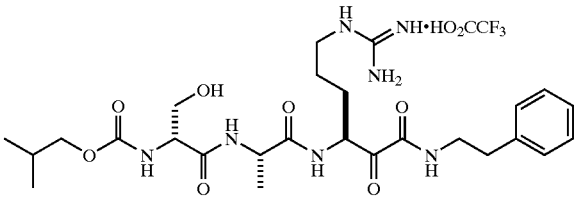

The compound of Example 33 (68 mg, 0.1 mmol) and anisole (1 mL) were added to an HF vessel. The mixture was treated with HF (10 mL) at −20° C. and stirred. After 30 minutes, the HF was evaporated. The residue was suspended in 20% acetic acid and washed with diethyl ether (3×). The aqueous layer was lyophilized. The crude lyophilate was purified by reverse phase prep HPLC (0.1% trifluoroacetic acid in 0–40% aqueous acetonitrile, C-18 reverse-phase), and lyophilized to afford 14.4 g of the title compound in 26% yield. $t_R$=12.5 minutes (0.1% trifluoroacetic acid in 5–75% aqueous acetonitrile over 20 minutes) and MS(M+H= 564.5).

(iv) Examples 35 to 40 describe an alternative synthetic route to make compound 1

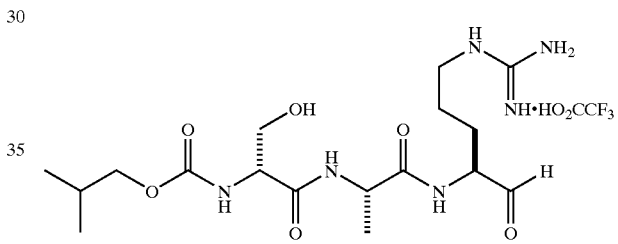

Example 35

Synthesis of i-butoxycarbonyl-D-Ser(O-t-Bu)-OMe

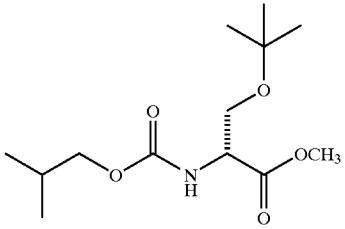

To a stirred homogeneous solution of HCl-D-Ser(O-t-Bu)-OMe (15 g, 71 mmol, Bachem) in tetrahydrofuran (200 mL) was added saturated sodium bicarbonate (80 mL), followed by isobutylchloroformate (19.45 g, 142 mmol). Layers were separated and the aqueous layer was washed with ethyl acetate (50 mL). The organic phases were combined, and solvent was removed under reduced pressure. The residue was suspended in ethyl acetate (100 mL) and washed with 1M HCl (100 mL), saturated sodium bicarbonate (100 mL), and brine (100 mL) The organic layer was dried with magnesium sulfate, treated with decolorizing charcoal, (such as that sold under the trade name Darco), filtered, and solvent removed under reduced pressure, giving quantitative yield of the title compound. R$_f$=0.3 (20% ethyl acetate/hexanes).

Example 36

Synthesis of i-butoxycarbonyl-D-Ser(O-t-Bu)-OH

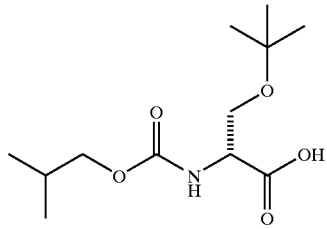

To a stirred solution of the compound of Example 35 (19.51 g, 70 mmol) in tetrahydrofuran (78 mL) was added lithium hydroxide (78 mmol, 3.28 g). The reaction mixture was stirred vigorously for 3 hours until no starting material was observed by TLC (20% ethyl acetate/hexanes). The solution was acidified with concentrated HCl to pH~2, and the solvent removed under reduced pressure. The crude product was suspended in ethyl acetate and extracted with saturated sodium bicarbonate (2×, 75 mL). The combined sodium bicarbonate washes were acidified with 6M HCl, and the oil that separated was extracted with ethyl acetate (2×100 mL). The combined organic layers were dried with magnesium sulfate, treated with Darco, filtered, and solvent removed under reduced pressure, giving quantitative yield of the title compound. R$_f$=0.01 (20% ethyl acetate in hexanes).

Example 37

Synthesis of i-butoxycarbonyl-D-Ser(O-t-Bu)-Ala-OMe

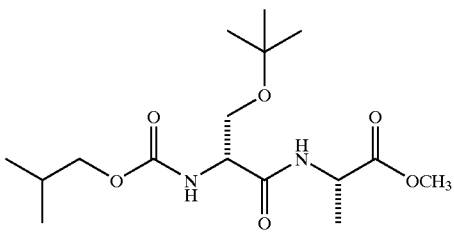

To a solution of the compound of Example 36 (16.5 g, 63 mmol), HCl-Ala-OMe (10.6 g, 76 mmol), 1-hydroxybenzotriazole (10.2 g, 76 mmol), and EDC (16.33 g, 85 mmol) in acetonitrile (280 mL) at 0° C., was added 4-methylmorpholine (35 mL, 315 mmol). This mixture was stirred for 1 hour at 0° C., then at ambient temperature for 72 hours. The solvent was removed under reduced pressure, and the resulting residue suspended in ethyl acetate(300 mL) and 1M HCl (350 mL). The aqueous layer was separated and washed with ethyl acetate (300 mL). The combined ethyl acetate layers were combined and washed with 1M HCl (300 mL), saturated sodium bicarbonate (400 mL), and brine (200 mL). The organic layer was dried with magnesium sulfate, treated with Darco, filtered and solvent removed under reduced pressure, yielding 21.48 g of the title compound (98% yield).

Example 38

Synthesis of i-butoxycarbonyl-D-Ser-Ala-OH

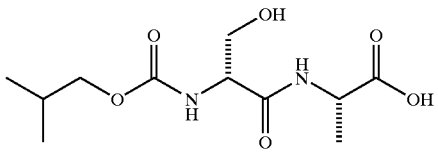

The compound of Example 37 (21 g, 58 mmol) was dissolved in trifluoroacetic acid (110 mL) and stirred for 35 minutes. The solution was cooled in an ice bath, and saturated sodium bicarbonate (630 mL) was added, followed by solid sodium bicarbonate (70 g) over 45 minutes to a resulting pH=7. The aqueous solution was extracted with ethyl acetate (3×250 mL). The combined organic extracts were combined, dried with magnesium sulfate, treated with Darco, filtered and solvent removed in vacuo, giving a quantitative yield of i-butoxycarbonyl-D-Ser-Ala-OMe. To a stirred solution of the crude residue in tetrahydrofuran (68 mL) was added lithium hydroxide (2.7 g, 64 mmol, 1.1 eq.) in water (17 mL) was added. The reaction mixture was stirred vigorously for 0.5 hours until there was no more of the starting material observed by TLC (9:1 dichloromethane/isopropanol). The solution was acidified with 6M HCl (13 mL) to pH~2, and the solvent removed under reduced pressure. The crude product was suspended in ethyl acetate (400 mL) and water (50 mL). The aqueous layer was extracted with ethyl acetate (200 mL). The combined organic layers were dried with magnesium sulfate, filtered, and solvent removed in vacuo, yielding 13.94 g of the title compound (86% yield). R$_f$=0.3 (90:30:5 chloroform/methanol/acetic acid).

Example 39

Synthesis of i-butoxycarbonyl-D-Ser-Ala-N$^g$-nitroArg-O(ethyl cyclol)

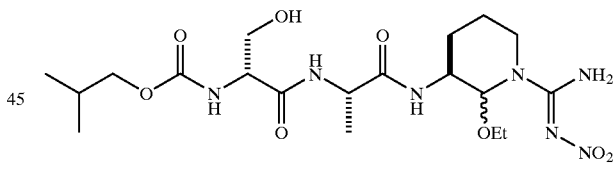

To mechanically stirred solution of 2,6-lutidine (30.5 mL, 272 mmol) in acetonitrile (520 mL) at 0° C. was added L-N$^g$-nitroargininal ethyl cyclol, hydrochloride salt (16.44 g, 61 mmol). To this mixture, the compound of Example 38 (13.94 g, 50.5 mmol) in acetonitrile (200 mL) was added, followed by 1-hydroxybenzotriazole (8.32 g, 33 mmol). The resulting mixture was stirred rapidly. EDC (12.9 g, 67 mmol) was added in small portions over 15 minutes. The ice bath was removed, and the mixture was stirred for an additional 69 hours. The solution was concentrated under reduced pressure, and the residue dissolved in ethyl acetate (300 mL) and 6M HCl (200 mL). The resulting precipitate was filtered and dried to give Lot I. The layers from the filtrate were separated, and the organic layer washed with 1M HCl (200 mL). The combined aqueous layers were saturated with NaCl and extracted with ethyl acetate (300 mL). The combined organic layers were washed with saturated sodium bicarbonate (300 mL) and brine (150 mL), dried over magnesium sulfate, and the solvent removed under reduced pressure to give Lot II. The sodium bicarbonate washes were extracted with 20% isopropanol in dichloromethane (2×150 mL). The combined organic layers were dried with magnesium sulfate, and the solvent removed under reduced pressure to give Lot III. Lots I, II, and III were each dissolved in minimum amount of hot acetonitrile and cooled overnight. The resulting solids were filtered and dried, yielding Lot I (4.15 g), Lot II (6.63 g), and Lot III (0.3 g). Lots I, II and III were identical by TLC and $^1$H NMR. The combined yield of the title compound was 11.08 g, (45% yield).

Example 40 i-butoxycarbonyl-D-Ser-Ala-Arg-al, Trifluoroacetate Salt (Compound 1)

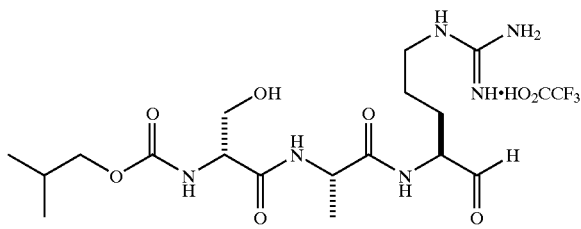

To a solution of the compound of Example 39 (11.48 g, 23.5 mmol) in ethanol/acetic acid (230 mL of a 1:1 mixture) was added 10% palladium on carbon (5.74 g), and the mixture was heated to 48° C. Over a period of 45 minutes ammonium formate (8.82 g, 140 mmol,) in water (9 mL) was added. The mixture was stirred for 3 hours, cooled and filtered. The residue was washed with ethanol and solvent removed under reduced pressure. The residue was dissolved in water (250 mL) and lyophilized, giving quantitative yield of i-butoxycarbonyl-D-Ser-Ala-L-argininal ethyl cyclol. $t_R$=12 minutes at 0.1% trifluoroacetic acid in 15–25% aqueous acetonitrile over 20 minutes. To i-butoxycarbonyl-D-Ser-Ala-L-argininal ethyl cyclol at 0° C., was added cold 6M HCl (115 mL). This mixture was stirred for 50 minutes. The ice bath was removed, and the reaction mixture was stirred at ambient temperature for 2 hours. After this time, the solution was recooled in ice bath, and sodium acetate (100 g) in water (200 mL) was added. The solution was filtered and purified by prep HPLC (using a 0.1% trifluoroacetic acid step gradient of 10,18,30,50% aqueous acetonitrile, C-18 reverse phase column) to afford three lots of the title compound: lot I (1.41 g, 14%, 99% purity), lot II (1.52 g, 16%, 98% purity), and lot III (3.13 g, 32%, 95% purity). $t_R$=9.46 minutes, 12.82 minutes and 13.87 minutes (reverse-phase HPLC, C-18, 0.1% trifluoroacetic acid in 10–20% aqueous acetonitrile over 20 minutes). MS(M+H=417.5).

(v) Examples 41 to 45 describe the synthesis of argininal-hydrazonylcarbonyl-aminomethylated polystyrene resin used to synthesize compounds of the present invention. See FIG. 6.

Example 41

Preparation of t-Butoxycarbonyl-Hydrazonyl-Carbonyl-Aminomethylated Polystyrene Resin

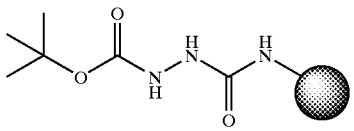

To a suspension of 1,1-carbonyldiimidiazole (29.19 g, 180 mmol, 6 equiv.) in dimethylformamide (300 mL) was added portionwise t-butylcarbazate (23.76 g, 180 mmol, 6 equiv.) with stirring at ambient temperature under a nitrogen atmosphere. After the addition was completed, the reaction mixture was allowed to stir at room temperature for 2½ hours and then poured into aminomethylated polystyrene resin (30 g, 1 meq/g, Advance Chemtech) in the peptide synthesis flask. The suspension was purged with nitrogen gas for 3 hours. The resin was filtered and washed with 3×350 mL portions of methylene chloride. Kaiser Test (solution and bead; light blue, clear). A double coupling was undertaken to ensure a quantitative reaction, however double coupling is optional. Thus, a solution of 1,1-carbonyldiimidiazole (14.60 g, 90 mmol, 3 equiv.) and t-butylcarbazate (11.88 g, 90 mmol, 3 equiv.) in 150 dimethylformamide was stirred at ambient temperature for 30 minutes and then poured into the previously prepared resin. After purging with nitrogen gas for 1 hour, the resin was filtered and washed with 6×350 mL portions each of methylene chloride, methanol, methylene choloride, methanol, methylene chloride, and methanol. Kaiser Test (solution and bead; clear and clear). The resin was dried under vacuum and acetylated with DMF/acetic anhydreide/Et$_3$N (8:1:1; about 300 mL) for 30 minutes at ambient temperature. The resin was successively washed 3 times each with solvents (methylene chloride and methanol) and dried under vacuum to afford product in quantitative yield.

Example 42

Hydrazonylcarbonyl-Aminomethylated Polystyrene Resin

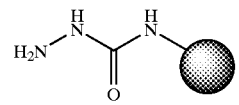

A solution of DCM/TFA (1:1) (300 mL) and thioanisole (10 mL) was added to the resin of Example 41 (30 g) to effect deprotection. The mixture was purged slowly with the nitrogen gas in the peptide synthesizer flask at ambient temperature for 30 minutes. The deprotected resin was filtered and washed with DCM (2×), DCM/DIEA (2×), DCM (2×) and alternatively with organic solvents (methylene chloride, methanol). The resulting title resin was dried under vacuum. Kaiser Test (solution and bead; light blue, sand color); afforded overall yield 30.64 g resin (approx. 0.85 meq semicarbazide/g).

Alternatively, the title resin was prepared as follows: to amino methylated polystyrene resin (1.0 g, 1.0 mmol, Advanced Chemtech) in N,N-dimethylformamide (12 mL) was added 1,1-carbonyldiimidazole (3.89 g, 24.0 mmol, 24 equiv.). The suspension was shaken at room temperature for 5 hours and then filtered in a peptide synthesis flask. The resin was washed with copious amounts of methylene chloride. Kaiser Test (solution and bead; light blue, white). A 2M solution of hydrazine in N,N-dimethyl formamide (12 mL) was added to the resin and allowed to shake at ambient temperature overnight. The resin was filtered and washed alternately with organic solvents (methylene chloride and methanol) and dried under vacuum to afford title product 1.06 g (approx. 0.94 mmol/g).

Example 43

Preparation of N-α-fluorenylmethyloxycarbonyl-omega, omega'-di-N-t-butoxycarbonyl-arginine Methyl Ester

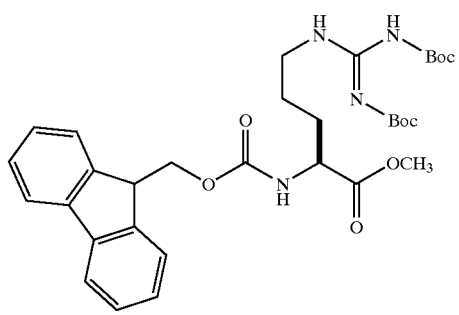

To a solution of N-α-fluorenylmethyloxycarbonyl-omega, omega'-di-N-t-butoxycarbonyl-arginine (4.97 g, 8.329 mmol, Advanced Chemtech) in acetonitrile (82 mL) was added potassium carbonate (1.38 g, 10 mmol) and methyl iodide (1.037 mL, 16.66 mmol). The mixture was warmed to 50° C. After stirring for 4.5 hours at 50° C., the reaction mixture was poured into ethyl acetate (500 mL) and washed successively with water (1×50 mL), saturated sodium bicarbonate (1×50 mL), and brine (1×50 mL). The organic phase was dried with sodium sulfate, and solvent was removed under reduced pressure yielding 4.7 g of the title compound.

Example 44

Preparation of N-α-fluorenylmethyloxycarbonyl-omega, omega'-di-N-t-butoxycarbonyl-argininol

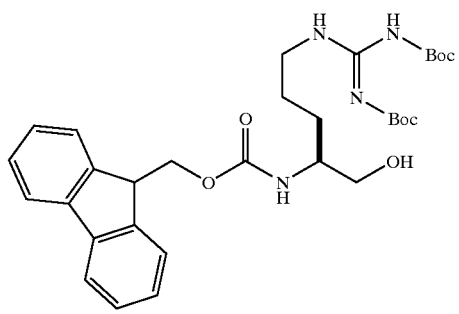

To a solution of the compound of Example 43 (5.675 g, 9.29 mmol) in tetrahydrofuran (15.5 mL) and methanol (93 mL) was added calcium chloride(2.06 g, 18.58 mmol), and the mixture was cooled in an ice bath. Sodium borohydride (1.4 g, 37.17 mmol) was added slowly in portions to the stirred cooled solution. After 1.5 hours solvent was removed under reduced pressure. The residue was suspended in ethyl acetate (500 mL) and water (300 mL). The phases were separated, and the organic layer was washed successively with 0.5M HCl (200 mL), and brine (200 mL). The combined aqueous washes were back extracted with ethyl acetate. The ethyl acetate layers were combined, silica was added (30 g), and solvent was removed under reduced pressure. This silica was loaded onto a 150×80 mm silica flash column, and the product was eluted with 50% ethyl acetate/hexanes to afford 3.855 g (71% yield) of the title compound. 0.938 g (17% yield) of the compound of Example 43 (starting material) was recovered. Rf=0.30 (50% ethyl acetate/hexanes). $^1$H NMR (CDCl3): 8.35 ppm (bs, 1H), 7.75 ppm(m, 2H), 7.6 ppm(m, 2H), 7.38 ppm(m, 2H), 7.3 ppm(m, 2H), 5.45 ppm(m, 1H), 4.4 ppm(d, 2H), 4.2 ppm(m, 1H), 3.7 ppm(m, 2H), 3.57 ppm(m, 1H), 3.45 ppm(m, 1H), 3.35 ppm(m, 2H), 2.15 ppm(m, 1H), 1.6 ppm(m, 4H), 1.45 ppm(d, 18H).

Example 45

Preparation of N-α-fluorenylmethyloxycarbonyl-omega, omega'-di-N-t-butoxycarbonyl Argininal Hydrazonylcarbonyl Aminomethylated Polystyrene Resin

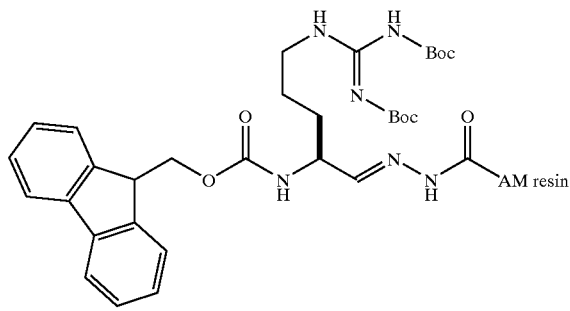

To a solution of the compound of Example 44 (3.62 g, 6.21 mmol) in methyl sulfoxide (31 mL) and toluene (31 mL) cooled in an ice bath was added EDC (11.93 g, 62.1 mmol) and dichloroacetic acid (2.56 mL, 31.06 mmol). The reaction mixture was stirred for 40 minutes until no starting material was observed by TLC (50% ethyl acetate/hexanes). Water (150 mL) and ethyl acetate (500 mL) were added, and the phases were separated. The organic layer was then washed successively with 0.5M HCl (100 mL), saturated sodium bicarbonate (2×100 mL), and brine (100 mL). The organic layer was dried with sodium sulfate, and solvent removed under reduced pressure. This residue was the dissolved in dichloromethane (45 mL), added to the compound of Example 42 (3.65 g, 3.1 mmol), and stirred in a sealed tube end over end overnight. The resin was filtered and washed successively with dichloromethane (3×50 mL), dimethylformamide (3×50 mL), and methanol (3×50 mL), and dried under high vacuum. Yield of title compound was 4.3 g. The piperidine fulvene determination of the loading showed 0.37 mmol/g (60% coupling).

(vi) Example 46 describes the synthesis of benzenesulfonyl-D-seryl-azetidyl-argininal, trifluoroacetate salt (compound 31). See FIG. 7.

Example 46

Preparation of benzenesulfonyl-D-seryl-azetididyl-argininal, Trifluoracetate Salt

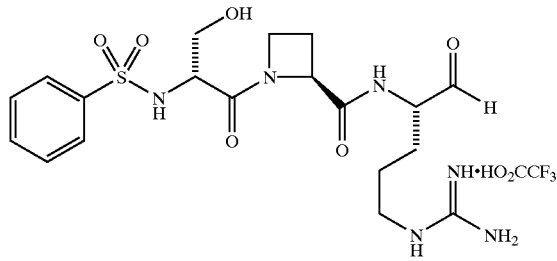

Step 1: omega, omega'-di-N-t-butoxycarbonyl-Argininal Hydrazonylcarbonyl Aminomethylated Polystyrene Resin

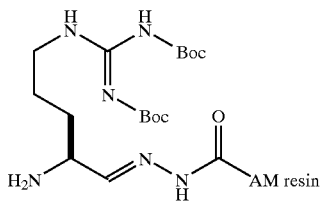

The resin product of Example 45, (125 mg) was treated with 30% piperidine/dimethylformamide (1.5 mL) in a 4 mL polypropylene column. After 30 minutes, the resin was drained, washed successively with dichloromethane (2×3 mL) and methanol (2×3 mL), and dried under vacuum to give the title compound. A ninhydrin assay on a small aliquot gave dark blue resin and solution showing a high yield for the deprotection.

Step 2: Preparation of N-α-Fmoc-azetidine-2-carbonyl-omega, omega'-di-N-t-butoxycarbonyl-argininal Hydrazonylcarbonyl Aminomethylated Polystyrene Resin

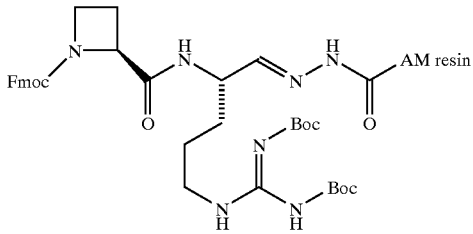

To the compound of Step 1 (0.12 g) in a 4 mL polypropylene column were added N-α-Fmoc-azetidine-2-carboxylic acid (110 mg, 0.34 mmol), 1-hydroxybenzotriazole (7.7 mg, 0.057 mmol), TBTU (37 mg, 0.11 mmol) and diisopropylethylamine (29.8 μL, 0.17 mmol) in dimethylformamide (95 μL). The reaction mixture was shaken at room temperature overnight. The reagents were drained from the resin and the resin was washed successively with dichloromethane (2×3 mL), and methanol (2×3 mL). The resin was vacuum dried and a small aliquot was taken for ninhydrin calorimetric analysis which showed a 97% coupling efficiency in the production the title compound.

Step 3: Azetidine-2-carbonyl-omega, omega'-di-N-t-butoxycarbonyl-Argininal Hydrazonylcarbonyl Aminomethylated Polystyrene Resin

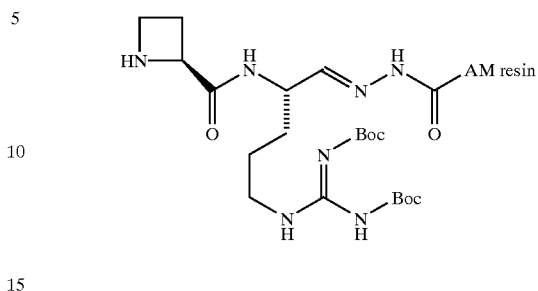

The compound of Step 2 was treated with 30% piperidine/dimethylformamide (1.5 mL) in a 4 mL polypropylene column. After 30 minutes, the resin was drained, washed successively with dichloromethane (2×3 mL) and methanol (2×3 mL), and dried under vacuum to give the title compound. A ninhydrin assay on a small aliquot gave dark blue resin and solution showing a high yield for the deprotection.

Step 4: Preparation of N-α-Fmoc-seryl(O-t-Bu)-azetidine-2-carbonyl-N-omega, omega'-di-N-t-butoxycarbonyl-argininal Hydrazonylcarbonyl Aminomethylated Polystyrene Resin

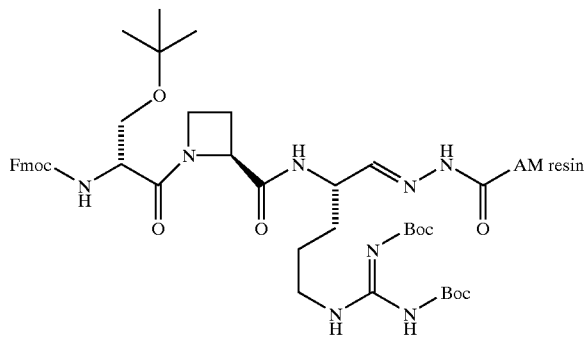

To the compound of Step 3 (0.12 g) in a 4 mL polypropylene column were added N-α-Fmoc-D-serine t-butyl ether (43 mg, 0.11 mmol), 1-hydroxybenzotriazole (7.7 mg, 0.057 mmol), TBTU (37 mg, 0.11 mmol) and diisopropylethylamine (29.8 μL, 0.17 mmol) in dimethylformamide (95 μL). The reaction mixture was shaken 4 hours at room temperature. The reagents were drained from the resin, and the resin was washed successively with dichloromethane (2×3 mL), and methanol (2×3 mL). The resin was dried under vacuum, then double coupled using N-α-Fmoc-serine O-t-butyl ether (43 mg, 0.11 mmol), 1-hydroxybenzotriazole (7.7 mg, 0.057 mmol), TBTU (37 mg, 0.11 mmol) and diisopropylethylamine (29.8 μL, 0.17 mmol) in dimethylformamide (95 μL). The reaction mixture was shaken 2 hours at room temperature. The reagents were drained from the resin, and the resin was washed successively with dichloromethane (2×3 mL), and methanol (2×3 mL). The resin was dried under vacuum, and a small aliquot was taken for ninhydrin colorimetric analysis which showed a 97.4% coupling efficiency in the production the title compound.

Step 5: Seryl(O-t-Bu)-azetidine-2-carbonyl-omega, omega'-di-N-t-butoxycarbonyl-argininal Hydrazonylcarbonyl Aminomethylated Polystyrene Resin

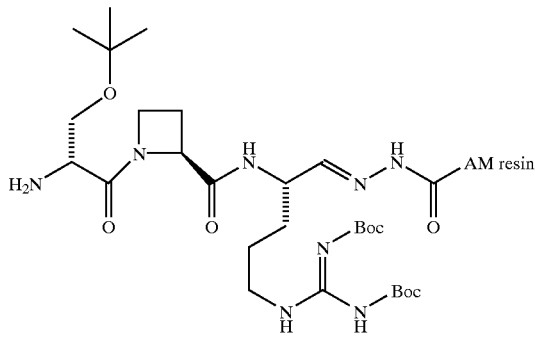

The compound of Step 4 was treated with 30% piperidine/dimethylformamide (1.5 mL) in a 4 mL polypropylene column. After 30 minutes, the resin was drained, washed successively with dichloromethane (2×3 mL) and methanol (2×3 mL), and dried under vacuum to give the title compound. A ninhydrin assay on a small aliquot gave dark blue resin and solution showing a high yield for the deprotection.

Step 6: Preparation of N-α-benzenesulfonyl-D-seryl(O-t-Bu)-azetidine-2-carbonyl-omega, omega'-di-N-t-butoxycarbonyl-argininal Hydrazonylcarbonyl Aminomethylated Polystyrene Resin

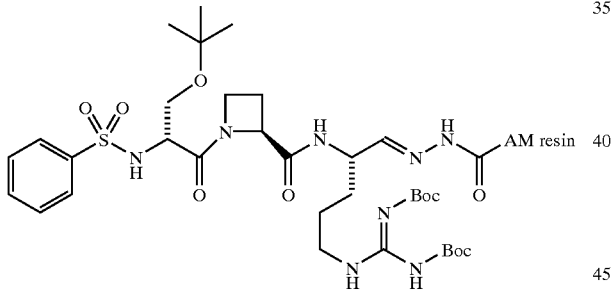

To the compound of Step 5 (0.12 g) in a 4 mL polypropylene column were added benzenesulfonyl chloride (17 µL, 0.133 mmol), and diisopropylethylamine (46.3 µL, 0.27 mmol) in dimethylformamide (888 µL). The reaction mixture was shaken overnight at room temperature. The reagents were drained from the resin, and the resin was washed successively with dichloromethane (2×3 mL), and methanol (2×3 mL). The resin was dried under vacuum, then double coupled with benzenesulfonyl chloride (17 µL, 0.133 mmol), and diisopropylethylamine (46.3 µL, 0.27 mmol) in dimethylformamide (888 µL). The reaction mixture was shaken 3 hours at room temperature. The reagents were drained from the resin, and the resin was washed successively with dichloromethane (2×3 mL), and methanol (2×3 mL). The resin was dried under vacuum, and a small aliquot was taken for ninhydrin colorimetric analysis which showed a 96% coupling efficiency in the production the title compound.

Step 7: benzenesulfonyl-D-seryl-azetidine-2-carbonyl-argininal, Trifluoroacetate Salt

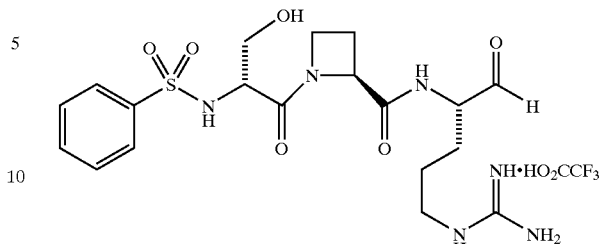

The compound of Step 6 (45 mg) in a 4 mL polypropylene fritted column was treated with trifluoroacetic acid/water (0.5 mL of a 9:1 mixture). The column was shaken for 1.5 hours at room temperature. The reaction solution was drained into a test tube and the resin was washed with water to a total volume of 5.2 mL filtrate. The title compound was purified by semipreparative reverse-phase HPLC (0.1% trifluoroacetic acid in 0–40% aqueous acetonitrile, C-18 reverse-phase), and lyophilized to afford 14.4 g of the title compound in 26% yield. The pure fractions, as analyzed by HPLC, were combined and lyophilized to afford the title compound (2.1 mg). MS (M+H=469).

(vii) Examples 47 to 50 describe the synthesis of N-α-(3-phenylpropyl)-D-seryl-alanyl-argininal, trifluoroacetate salt (compound 32).

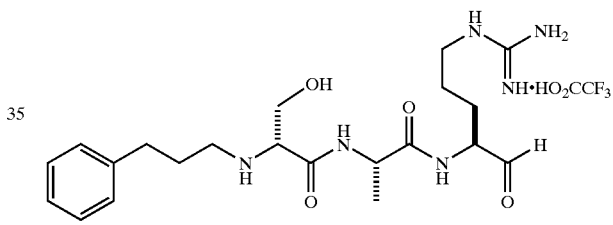

Example 47

Preparation of N-α-(3-phenylpropyl)-D-serine-t-butyl Ether Methyl Ester

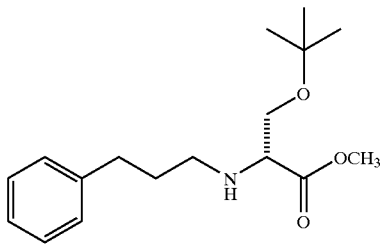

Serine O-t-butyl ether methyl ester (1.50 g, 7.1 mmol), hydrocinnamaldehyde (1.40 mL, 10.6 mmol), and triethylamine (1.18 mL, 8.5 mmol) were refluxed in tetrahydrofuran (70 mL) for 4 hours. After the solution was allowed to cool to room temperature, sodium borohydride (0.46 g, 12 mmol) was added in two portions to the stirred solution. The reaction mixture was stirred at ambient temperature for 30 minutes, and the solution was concentrated under reduced pressure. The residue was partitioned between ethyl acetate 1.0M HCl. The organic layer was washed with 1.0N HCl.

The aqueous layer was basified with 40% NaOH to pH 10, then extracted with ethyl acetate (2x). The combined organic layers were dried over sodium sulfate, and the solvent was removed in vacuo. The residue was purified by flash chromatography over silica gel (1×6 inch column) eluting with 10–30% ethyl acetate/hexanes to afford 150 mg (7% yield) of the title compound. $R_f$=0.60 (50% ethyl acetate/hexanes).

Example 48

Preparation of N-α-t-butoxycarbonyl-N-α-(3-phenylpropyl)-D-serine-t-butyl Ether Methyl Ester

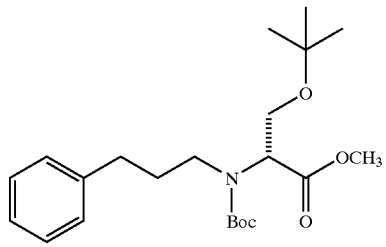

The compound of Example 47 (150 mg, 0.51 mmol), di-t-butyldicarbonate (167 mg, 0.77 mmol) and diisopropylethylamine (0.13 mL, 0.77 mmol) were stirred in tetrahydrofuran (2 mL) at ambient temperature overnight. The reaction mixture was concentrated under reduced pressure. The residue was diluted with ethyl acetate (20 mL), washed successively with 1.0N HCl (2x), saturated sodium bicarbonate (2x), and brine (1x), and the solvent was removed in vacuo to afford 206 mg of the title compound in quanititative yield. $R_f$=0.74 (50% ethyl acetate/hexanes).

Example 49

Preparation of N-α-t-butoxycarbonyl-N-α-(3-phenylpropyl)-D-serine-t-butyl Ether

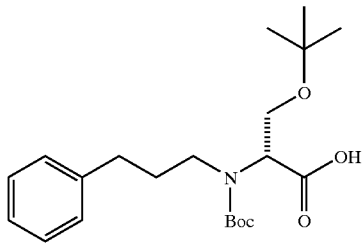

To a solution of the compound of Example 48 (206 mg, 0.52 mmol) in methanol (3.5 mL) was added dropwise 1.0N LiOH (0.63 mL, 0.63 mmol). The solution became cloudy, then became homogeneous in 5 minutes. The reaction mixture was allowed to stir at ambient temperature overnight. Additional 1.0N LiOH (1.47 mL) was added. After 2 hours, additional 1.0N LiOH (1.0 mL) was added. After no starting material was observed by TLC (50% ethyl acetate/hexanes), the reaction mixture was acidified to pH4 with DOWEX (50×8-400) ion exchange resin. The solution was filtered, rinsing with methanol, then water. The solution was concentrated under reduced pressure, then lyophilized to afford 189 mg of the title compound in 95% yield as a yellow oil. $R_f$=0.04 (50% ethyl acetate/hexanes).

Example 50

Preparation of N-α-(3-phenylpropyl)-D-seryl-alanyl-argininal, Trifluoroacetate Salt (Compound 32)

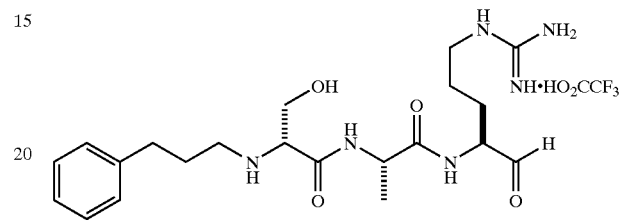

Steps 1 through 4 and Step 7 of Example 46 were followed, with the substitution in Step 2 of N-α-Fmoc-alanine for N-α-Fmoc-azetidine, and with the substitution in Step 4 of the compound of Example 49 for N-α-Fmoc-D-serine O-t-butyl ether, to make the title compound.

(viii) Examples 51 to 53 describe solid phase synthesis of certain compounds of the present invention.

Example 51

Solid Phase Synthesis of Compounds 44, 47, and 48

Steps 1 through 4 and Step 7 of Example 46 are followed, with the noted substitution in Step 4 for Fmoc-D-serine(O-t-buytl):

| COMPOUND NUMBER | COMPOUND NAME | SUBSTITUTION IN STEP 4 |
|---|---|---|
| 44 | benzyloxycarbonyl-D-2-aminobutyryl-L-alanyl-argininal | Cbz-D-2-aminobutyric acid |
| 47 | 2-phenylethylsulfonyl-D-seryl-alanyl-argininal | 2-phenylethyl-sulfonyl-D-serine-(O-t-butyl) |
| 48 | 3-phenylpropylsulfonyl-D-seryl-alanyl-argininal | 3-phenylpropyl-sulfonyl-D-serine (O-t-butyl) |

For synthesis of 2-phenylethylsulfonyl-D-serine-O-t-butyl, the procedures of Examples 22 and 23 were followed with two substitutions in Example 22. Either 2-phenylethylsulfonyl chloride or 3-phenylpropylsulfonyl chloride was substituted for α-toluenesulfonyl chloride, and 4-methylmorpholine was used in place of diisopropylethylamine.

Example 52

Solid Phase Synthesis of Compounds 45, 46, and 49 to 51

Steps 1 through 4 and Step 7 of Example 46 are followed, with the substitution of Cbz-D-serine(O-t-butyl) for Fmoc-D-serine(O-t-butyl) in Step 4, and the noted substitution in Step 2 for Fmoc-L-azetidine-2-carboxylic acid:

| COMPOUND NUMBER | COMPOUND NAME | SUBSTITUTION IN STEP 2 |
|---|---|---|
| 45 | benzyloxycarbonyl-D-seryl-L-seryl-argininal | Fmoc-L-serine-O-t-butyl |
| 46 | benzyloxycarbonyl-D-seryl-L-β-cyanoalanine-argininal | Fmoc-L-β-cyanoalanine |
| 49 | benzyloxycarbonyl-D-seryl-L-cis-4-hydroxyprolyl-argininal | Fmoc-cis-4-hydroxyproline |
| 50 | benzyloxycarbonyl-D-seryl-L-3,4-dehydroprolyl-argininal | Fmoc-L-3,4-dehydroproline |
| 51 | benzyloxycarbonyl-D-seryl-L-propargylglycyl-argininal | Fmoc-L-propargylglycine |
| 52 | benzyloxycarbonyl-D-seryl-L-allylglycyl-argininal | Fmoc-L-allylglycine |

Example 53

Solid Phase Synthesis of trans-β-styrenesulfonyl-D-seryl-L-alanyl-argininal (Compound 53)

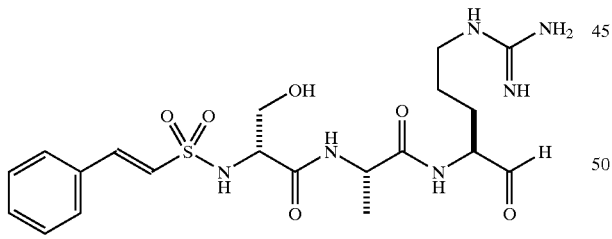

Steps 1 through 7 of Example 46 are followed, with the substitution of Fmoc-L-alanine for N$^\alpha$Fmoc-azetidine-2-carboxylic acid in Step 2, and the substitution of trans-β-styrenesulfonyl chloride for benzenesulfonyl chloride in Step 6, to make the title compound.

(ix) Examples 54 to 59 describe an alternate synthesis method for compound 1. See FIG. 5.

Example 54

Preparation of i-butoxycarbonyl-D-Ser(O-t-butyl)-OH

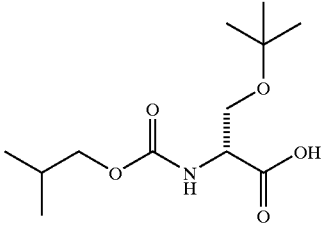

To a solution of D-serine-O-t-butyl ether (10.5 g, 65.3 mmol) in water (51 mL) was added sodium carbonate (20.1 g, 196.2 mmol) followed by isobutyl chloroformate (9.8 mL, 75.2 mmol). After 3 hours this mixture became cloudy and and was stirred for an additional 3 hours. After 6 hours the solution was acidified with 6M HCl (~50 mL). The reaction mixture was then extracted with ethyl acetate (3×200 mL). After initial extraction the aqueous layer was saturated with sodium chloride and extracted with ethyl acetate (2×200 mL). The ethyl acetate layers were combined and dried with sodium sulfate, followed by removal of the solvent in vacuo yielding 17.0 g (99.5% yield) of the title compound as a white solid. HPLC: t=18.5 minutes in a 5% to 75% acetonitrile gradient in 0.1% aqueous TFA buffer on a 4.6×250 mm, 5 micron particle, 100 angstrom pore, C18 column at a 1 mL/min flow rate. NMR(CDCl$_3$): 5.5 ppm(m,1H), 4.45 ppm(bs,1H), 3.82–3.95 ppm(m,3H), 3.52–3.6 ppm(m,1H), 1.85–1.97 ppm(m,1H), 1.2 ppm(s,9H), 0.9 ppm(d,6H).

Example 55

Preparation of i-butoxycarbonyl-D-Ser(tBu)-L-Ala-OtBu

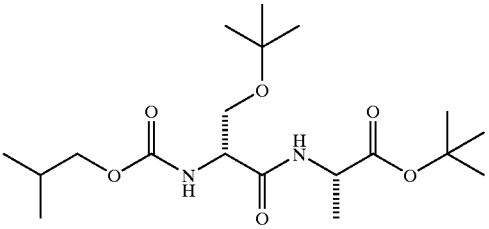

A solution of the compound of Example 54 (10 g, 38.3 mmol), L-alanine t-butyl ester, HCl salt (10.43 g, 57.4 mmol), EDC (11.05 g, 57 mmol), and hydroxybenzotriazole (5.85 g, 38.3 mmol) in acetonitrile (153 mL) was stirred for 15 minutes at room temp. Diisopropylethylamine (32.7 mL, 191 mmol) was added, and the reaction stirred for 18 hours. The solvent was removed under reduced pressure, and the resulting residue resuspended in ethyl acetate (1000 mL) and 1M HCl (100 mL). The ethyl acetate layer was washed with 0.5M HCl (100 mL), saturated with sodium bicarbonate (2×100 mL), and brine (100 mL). The ethyl acetate was dried with sodium sulfate, and solvent removed in vacuo, resulting in a quantitative yield of title compound. HPLC: t$_r$=18.7 minutes in a 5% to 90% acetonitrile gradient in 0.1% aqueous TFA buffer on a 4.6×250 mm, 5 micron particle, 100 angstrom pore, C18 column at a 1 mL/minute flow rate. NMR(CDCl$_3$): 7.15 ppm(bs, 1H), 5.6 ppm(bs, 1H), 4.4–4.5 ppm(m, 1H), 4.2 ppm(bs, 1H), 3.87–3.95 ppm(m, 3H), 3.3–3.4 ppm(m, 1H), 1.85–1.95 ppm(m, 1H), 1.45 ppm(s, 9H), 1.39 ppm(d, 3H), 1.2 ppm(s, 9H), 0.9 ppm(d, 6H).

Example 56

Preparation of i-butoxycarbonyl-D-Ser-L-Ala-OH

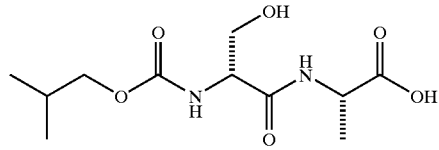

To a solution of the compound of Example 55 (7.15 g, 18.4 mmol) in dichloromethane (35 mL) was added trifluoroacetic acid (35 mL). This mixture was stirred for two hours, then solvent removed under reduced pressure. Toluene was added and the solvents were removed in vacuo to remove the trifluoroacetic acid. A quantitative yield of the title compound as a viscous yellow oil was then carried on to the next step. $t_r$=10.5 minutes in a 5% to 90% acetonitrile gradient in 0.1% aqueous TFA buffer on a 4.6×250 mm, 5 micron particle, 100 angstrom pore, C18 column at a 1 mL/minute flow rate.

Example 57

Preparation of i-butoxycarbonyl-D-Ser-L-Ala-N$^g$-nitroargininal-ethyl cyclol

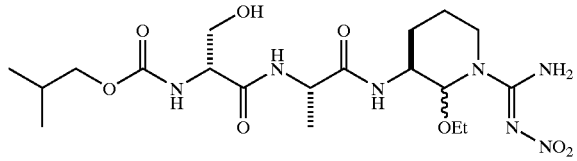

A solution of the compound of Example 56 (5.09 g, 18.4 mmol), N$^g$-nitroargininal ethyl cyclol, HCl salt (6.4 g, 23.9 mmol), EDC (5.31 g, 27.6 mmol), and hydroxybenzotriazole (2.82 g, 18.4 mmol) in acetonitrile (74 mL) was stirred for 15 minutes at ambient temperature. Diisopropylethylamine (15.7 mL, 92 mmol) was added, and the reaction mixture stirred for 18 hours. The solvent was removed under reduced pressure, and the resulting residue resuspended in ethyl acetate (1000 mL) and 0.5M HCl (100 mL). The ethyl acetate layer was washed with 0.5M HCl (100 mL), saturated sodium bicarbonate (2×100 mL), brine (100 mL), and dried with sodium sulfate. The solvent was removed under reduced pressure to a volume of ~25 ml resulting in a white precipitate. The reaction mixture was then left overnight at 4° C. The precipitate was then filtered and dried, resulting in 4.6 g (50% yield) of title compound as a single peak by HPLC: t=11.5 min in a 5% to 90% acetonitrile gradient in 0.1% aqueous TFA buffer on a 4.6×250 mm, 5 micron particle, 100 angstrom pore, C18 column at a 1 mL/minute flow rate.

Example 58

Preparation of i-butoxycarbonyl-D-Ser-L-Ala-Argininal-ethyl cyclol

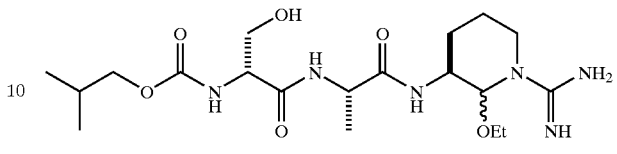

A solution of the compound of Example 57 (4.55 g, 9.3 mmol) in ethanol:water:acetic acid (55 mL of a 4:1:1 mixture) was flushed with nitrogen before palladium on carbon (1.15 g, 10% palladium, 50% water) was added. This mixture was hydrogenated at 50 psi for 18 hours. The reaction was then filtered to remove palladium, and solvent was removed in vacuo to give a quantitative yield of the title compound. HPLC: $t_r$=14.2 minutes in a 5% to 50% acetonitrile gradient in 0.1% aqueous TFA buffer on a 4.6×250 mm, 5 micron particle, 100 angstrom pore, C18 column at a 1 mL/minute flow rate.

Example 59

Preparation of i-butoxycarbonyl-D-Ser-L-Ala-Argininal (Compound 1)

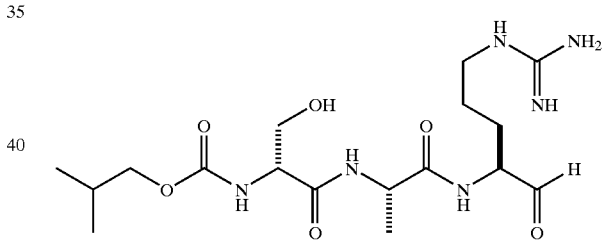

A solution of the compound of Example 58 (9.3 mmol) in 3M HCl was allowed to stir for three hours. This material was then loaded directly onto a 50×300 mm, 15 micron particle, 100 angstrom pore, C18 column at a 80 mL/minute flow rate in three lots. The fractions containing product were pooled and lyophilized, yielding 2.38 g (61% yield) of the title compound that was 97% pure by analytical HPLC. HPLC: t=16.4 minutes, 18.9 minutes and 19.6 minutes in a 5% to 25% acetonitrile gradient in 0.1% aqueous TFA buffer on a 4.6×250 mm, 5 micron particle, 100 angstrom pore, C18 column at a 1 mL/min flow rate. Mass spec (M+H)= 417. NMR(D$_2$O): 5.4 ppm(s, 1H), 4.25–4.37 ppm(m, 1H), 4.1–4.25 ppm(m, 1H), 3.75–3.95 ppm(m, 5H), 3.42–3.52 ppm(m, 1H), 3.2–3.3 ppm(m, 1H), 1.58–1.98 ppm(m, 5H), 1.35 ppm(d, 3H), 0.85 ppm(d, 6H).

(x) Examples 60 to 72 describe synthesis of certain intermediates which may be used in synthesis of compounds of the present invention. See FIG. 8 (Examples 60 to 64) and FIG. 9 (Examples 65 to 72).

Example 60

Preparation of N-(t-butoxycarbonyl)-3-(3-pyridyl)-L-alanine Methyl Ester

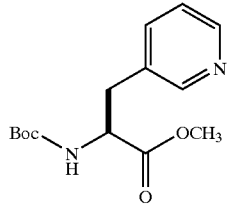

To a solution of N-(t-butoxycarbonyl)-3-(3-pyridyl) alanine (5.0 g, 18.8 mmol) in methanol (100 mL), was added thionyl chloride (2M solution in dichloromethane, 66 mL, 132 mmol). The resulting solution was stirred overnight at ambient temperature. The methanol was removed under reduced pressure to a minimum volume and ethyl acetate (100 mL) was added. The resulting white precipitate was collected in a fritted funnel. To a solution of the collected precipitate in a mixture of tetrahydrofuran/water (40 mL each), was added di-tert-butyl dicarbonate (4.8 g, 21.99 mmol) and sodium carbonate (1.95 g, 18.4 mmol). After stirring for 12 hours at ambient temperature, the reaction mixture was diluted with ethyl acetate (40 mL) and washed with a solution of saturated sodium bicarbonate (25 mL). The organic layer was dried over anhydrous sodium sulfate and concentrated under vacuum to give crude product. This product was subjected to flash column chromatography on silica gel (230–400 mesh) using a 8×52 cm column and eluting with a 10:90 mixture of ethyl acetate/hexane, followed by a 60:40 mixture of ethyl acetate/hexane. 4 g (74%) of the title compound was obtained as an oil. Thin-layer chromatography (silica gel; ethyl acetate), $R_f$=0.68.

Example 61

Preparation of N-(t-butoxycarbonyl)-3-([R,S]-3-piperidyl)-L-alanine Methyl Ester, Acetate Salt

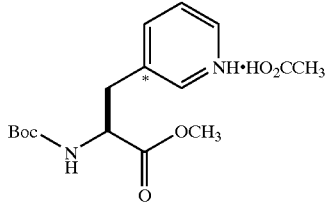

A solution of the compound of Example 60 (5 g, 17.8 mmol) in ethanol (24 mL), acetic acid (6 mL) and water (6 mL) was hydrogenated over platinum oxide (500 mg) at 45 psi for three hours. The catalyst was filtered off and the filtrate was concentrated under vacuum to an oily residue (6.89 g) which was used in the procedure described in Example 62 without further purification. Thin-layer chromatography yielded two spots corresponding to two diastereomers with $R_f$ values of 0.16 and 0.26, respectively (silica gel; 4:1:1 n-butanol/acetic acid/water).

Example 62

Preparation of N-(t-butoxycarbonyl)-3-[(R,S)-3-piperidyl-(N-guanidino(bis-benzyloxycarbonyl))]-L-alanine Methyl Ester

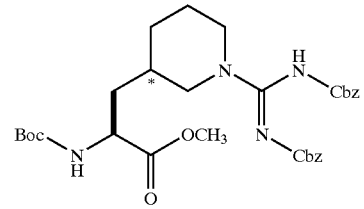

To a solution of the compound of Example 61 (6.89 g, 19.9 mmol) in tetrahydrofuran (80 mL), was added S-methylisothiourea bis-benzyloxycarbonyl (7.13 g, 19.9 mmol), followed by N-methylmorpholine (4.37 mL). The reaction mixture was stirred at ambient temperature for 18 hours. The reaction mixture then was concentrated under vacuum and the resulting residue was dissolved in ethyl acetate (100 mL) and washed with 1N sodium bisulfate and saturated sodium chloride (50 mL each). After drying over anhydrous sodium sulfate, the solvents were removed under vacuum; the crude title compound was subjected to flash column chromatography on silica gel (230–400 mesh) using a 8×52 cm column and eluting with 1:9 ethyl acetate/hexanes (two column volumes) followed by 1:1 ethyl acetate/hexanes. 2.75 g the title compound was obtained as a mixture of two diastereomers. Thin-layer chromatography gave two spots with $R_f$ values of 0.57 and 0.62, respectively (silica gel; 1:1 ethyl acetate/hexanes).

Example 63

Preparation of N-(t-butoxycarbonyl)-3-[(R,S)-3-piperidyl-(N-guanidino(bis-benzyloxycarbonyl))]-L-alaninol

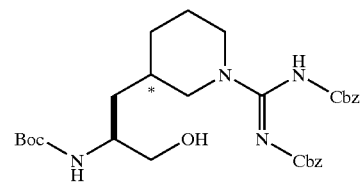

To a stirred solution of the compound of Example 62 (2.23 g, 3.7 mmol) in absolute ethanol (8 mL) and anhydrous tetrahydrofuran (4 mL), was added calcium chloride (844 mg, 7.6 mmol) and sodium borohydride (575 mg, 15.2 mmol). After stirring 12 hours at ambient temperature, the reaction mixture was concentrated under vacuum and the resulting residue was partitioned between ethyl acetate and 1N sodium bisulfate (10 mL each). The two layers were separated; the organic layer was washed twice more with 1N sodium bisulfate, dried over anhydrous sodium sulfate and concentrated under vacuum to give a residue. Flash column chromatography of the residue on silica gel (230–400 mesh) using a 5.5×45 cm column and eluting with ethyl acetate gave 1.3 g of the title compound as a white foam. Thin layer chromatography yielded two spots corresponding to two diastereomers with $R_f$ values of 0.18 and 0.27, respectively (silica gel; 1:1 ethyl acetate/hexanes).

Example 64

Preparation of 3-[(R,S)-3-piperidyl-(N-guanidino (bis-benzyloxycarbonyl))]-L-alaninol, Hydrochloride Salt

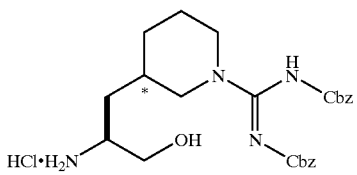

The compound of Example 63 (290 mg, 0.57 mmol) was treated with 2.5N anhydrous hydrochloric acid in ethyl acetate (2.0 mL) at ambient temperature for one hour. The solvent was removed under vacuum to a sticky-white solid (260 mg). This solid is used without further isolation to prepare a compound of the present invention having a 3-piperidinyl-(N-guanidino)-alaninal at P1. $^1$H NMR spectrum taken in CD$_3$OD showed no t-butoxycarbonyl protons at 1.4 ppm.

Example 65

Preparation semicarbazid-4-yl diphenylmethane, Trifluoroacetate Salt

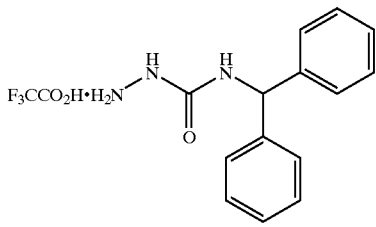

Step 1

A solution of carbonyldiimidazole (16.2 g, 0.10 mole) in 225 mL of dimethylformamide was prepared at room temperature and allowed to stir under nitrogen. A solution of t-butyl carbazate (13.2 g, 0.100 mole) in 225 mL dimethylformamide was then added dropwise over a 30 minute period. Next, diphenylmethylamine (18.3 g, 0.10 mole) was added over a 30 minute period. The reaction mixture was allowed to stir at room temperature under nitrogen for one hour. Water (10 mL) was added and this mixture was concentrated to about 150 mL under vacuum. This solution was poured into 500 mL water and then extracted with 400 mL of ethyl acetate. The ethyl acetate phase was extracted two times each with 75 mL 1N HCl, water, saturated sodium bicarbonate and brine, and then was dried with anhydrous magnesium sulfate. The mixture was filtered and the solution was concentrated to give 29.5 g (85% yield) of 1-t-butoxycarbonyl-semicarbazid-4-yl diphenylmethane as a white foam. This material may be purified by recrystalization from ethyl acetate/hexane, but was pure enough to use directly in step 2: mp 142–143☐ C. $^1$H NMR (CDCl$_3$) delta 1.45 (s, 9H), 6.10 (dd, 2H), 6.42 (s, 1H), 6.67 (bs, 1H), 7.21–7.31 (m, 10H). Analysis calculated for C$_{19}$H$_{23}$N$_3$O$_3$: C, 66.84; H, 6.79; N, 12.31. Found: C, 66.46; H, 6.75; N; 12.90.

Step 2

A solution of 3.43 g (10 mmol) of 1-t-butoxycarbonyl-semicarbazid-4-yl diphenylmethane in 12.5 mL of dichloromethane was treated with 12.5 mL of trifluoroacetic acid at 0° C. The reaction mixture was allowed to stir for 30 minutes at this temperature. The reaction mixture was then added dropwise to 75 mL of diethyl ether to give a precipitate. The resulting precipitate was filtered off and washed with diethyl ether to give 2.7 g (80% yield) of the title compound; mp 182–184° C.

Example 66

Preparation of 3-thioamidobenzyl-N-acetylaminomalonic Acid Diethyl Ester

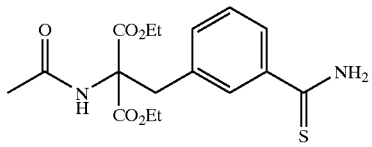

To a stirred solution of α-bromo-meta-tolunitrile (45.0 g, 0.24 mole), diethyl acetamidomalonate (48.0 g, 0.22 mole) and potassium iodide (3.0 g, 0.018 mole) in dioxane (500 mL), was added 2.5M sodium ethoxide in ethanol (100 mL) dropwise under an argon atmosphere. After the addition was complete, the solution was refluxed for 6 hours. The reaction mixture was allowed to stand overnight at room temperature, then diluted with brine (250 mL) and water (250 mL), and extracted with ethyl acetate four times (1.0 L total). The combined extracts were washed with water (100 mL), 10% citric acid (100 mL), water (100 mL) and brine (2×50 mL), then dried over anhydrous magnesium sulfate and filtered; the solvent was removed under vacuum. The crude residue was recrystallized from ethyl acetate and diethyl ether in two crops to yield 43.51 g (60%) of the 3-cyanobenzyl-N-acetylaminomalonic acid diethyl ester as yellow crystals.

H$_2$S(g) was bubbled into a rapidly stirring solution of 3-cyanobenzyl-N-acetylaminomalonic acid diethyl ester (44.3 g, 0.13 mmol) in pyridine (300 mL) and triethylamine (100 mL) for 40 minutes. The reaction mixture was stirred at room temperature for 16 hours, then poured into 3.0 L of water. A yellow precipitate formed immediately. The solution was allowed to stand at 4° C. for 4 hours, then was filtered. The crude title compound was recrystallized from ethyl acetate and hexanes to yield 48.1 g (98% yield) of the title compound as yellow crystals, m.p. 183–1860° C. $^1$H NMR (CDCl$_3$): delta 1.31 ( t, J=7.1 Hz, 6H), 2.06 (s, 3H), 3.70 (s, 2H), 4.29 (q, J=7.1 Hz, 4H), 4.80–4.87 (m, 1H), 6.60 (s, 1H), 7.10–7.20 (m, 1H), 7.27–7.35 (m, 2H), 7.60–7.70 (m, 2H). Analysis calculated for C$_{17}$H$_{22}$N$_2$O$_5$S: C, 55.72; H, 6.05; N, 7.64. Found: C, 55.55; H, 5.96; N, 7.76.

Example 67

Preparation of 3-amidino-D,L-phenylalanine, Dihydrochloride Salt

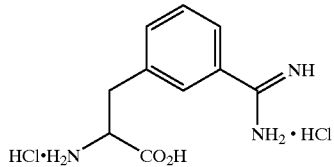

The compound of Example 66 (48.1 g, 0.13 mmol) was dissolved in acetone (800 mL). Iodomethane (18.3 mL, 0.19 mole, 1.5 equivalents) was added, and the solution was refluxed for 30 minutes. The solution was cooled to room temperature, and the intermediate thioimidate was filtered, dried and dissolved in methanol (500 mL). Ammonium acetate (14.8 g, 0.19 mole, 1.5 equivalents) was added. The reaction mixture was refluxed for 1 hour, then cooled to room temperature, and poured into ether (1.2 L). The solution was allowed to stand at 4° C. for 72 hours. The crude 3-amidinobenzyl-N-acetylaminomalonic acid diethyl ester was filtered, washed with ether, air dried, and then refluxed in concentrated HCl (250 mL) for 3 hours. The reaction mixture was concentrated under vacuum, diluted with water (0.5 L), and concentrated under vacuum again. These steps were repeated. The crude title compound was purified by cation-exchange (Sephadex SP-C25) using a gradient of 0–1.0N HCl as eluent to yield 10.8 g (30% yield) of the title compound as an off-white solid. $^1$H NMR (D$_2$O): delta 3.14–3.29 (2H, m), 4.17 (dd, J=7.4, 6.2 Hz, 1H), 7.42–7.69 (4H, m). Analysis calculated for $C_{10}H_{13}N_3O_2 \cdot 2HCl \cdot 9H_2O$: C, 38.20; H, 6.03; N, 13.36. Found: C, 38.51; H, 5.64; N, 12.89.

Example 68

Preparation of N-α-Boc-N-omega-4-methoxy-2,3,6-trimethylbenzenesulfonyl-3-amidino-D,L-phenylalanine

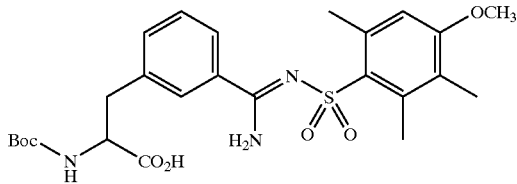

3-amidino-D,L-phenylalanine (the compound of Example 67,) (4.00 g, 13 mmol) was dissolved in 50% aqueous dioxane (20 mL). Sodium bicarbonate (3.38 g, 40 mmol) was added, followed by di-t-butyl dicarbonate (2.93 g, 13 mmol) in dioxane (4 mL). The reaction mixture was stirred for 18 hours at room temperature. The solution was cooled in an ice bath, and 4.0 N sodium hydroxide was added dropwise until the solution was pH 12. 4-methoxy-2,3,6-trimethylbenzenesulfonyl chloride (8.01 g, 32 mmol) in dioxane (10 mL) was added dropwise. 4.0 N sodium hydroxide was added as needed to keep the pH at 12. The ice bath was removed. After 1 hour, 1.0 N HCl was added to bring the solution to pH 7–8. The solution was diluted with an additional 50 mL of water and then was washed with ethyl acetate two times (20 mL each). The aqueous layer was acidified to pH 1.0 with 1.0 N HCl and extracted with ethyl acetate three times (100 mL total). The combined organic layers were washed with water (20 mL) and brine twice (10 mL each). The organic layer was dried over anhydrous magnesium sulfate and the solvent was removed under vacuum. The residue was dissolved in a minimum amount of dichloromethane, then added dropwise to ether (25 mL). Solid impurities were removed by filtering and the solvent removed from the filtrate under vacuum to give 4.90 g (68% crude yield) of the title compound as an off-white foam. A 30 mg sample of the title compound was further purified by preparative thin-layer chromatograph developing with 1% acetic acid/5% isopropanol/dichloromethane to give 9 mg of the title compound in a purer form. Rf=0.16 (1% acetic acid/5% isopropanol/dichloromethane). $^1$H NMR (CD$_3$OD): delta 1.32 (s, 9H), 2.14 (s, 3H), 2.63 (s, 3H), 2.71 (s, 3H), 2.93 (dd, J=13.7, 9.3 Hz, 1H), 3.22 (dd, J=13.7, 4.3 Hz, 1H), 3.85 (s, 3H), 4.34–4.37 (m, 1H), 6.72 (s, 1H), 7.35–7.47 (2H, m), 7.69–7.75 (m, 2H).

Example 69

Preparation of N-α-Boc-N-omega-4-methoxy-2,3,6-trimethylbenzenesulfonyl-3-amidino-D,L-phenylalanine-N-methyl-O-methyl-carboxamide

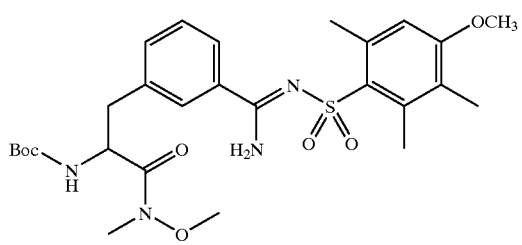

To a stirred solution of compound of Example 68 (1.00 g, 1.92 mmol), O,N-dimethyl hydroxylamine hydrochloride (375 mg, 3.85 mmol), hydroxybenzotriazole hydrate (294 mg, 1.92 mmol) and 4-methylmorpholine (1.06 mL, 9.62 mmol) in tetrahydrofuran (4 mL), cooled in an ice bath, was added EDC (406 mg, 2.12 mmol). The ice bath was removed, and the reaction mixture was stirred for 2 hours at room temperature. The reaction mixture was diluted with ethyl acetate (75 mL), washed with water, 10% citric acid, water, saturated sodium bicarbonate, and brine. The organic layer was dried over anhydrous magnesium sulfate and the solvent was removed under vacuum. 750 mg (69% yield) of the title compound was isolated. $^1$H NMR (CDCl$_3$): delta 1.33 (s, 9H), 2.14 (s, 3H), 2.66 (s, 3H), 2.75 (s, 3H), 2.80–2.88 (m, 1H), 3.06–3.20 (m, 4H), 3.70 (s, 3H), 3.84 (s, 3H), 4.98–5.06 (m, 1H), 5.21 (d, J=8.7 Hz, 1H), 6.48 (bs, 1H), 6.58 (s, 1H), 7.30–7.34 (m, 2H) 7.60–7.68 (m, 2H), 8.11 (bs, 1H). Analysis calculated for $C_{27}H_{38}N_4O_7S \cdot 0.5H_2O$: C, 56.73; H, 6.88; N, 9.80. Found: C, 56.97; H, 6.66; N, 9.43.

Example 70

Preparation of N-α-Boc-N-omega-4-methoxy-2,3,6-trimethylbenzenesulfonyl-D,L-3-amidinophenylalaninal

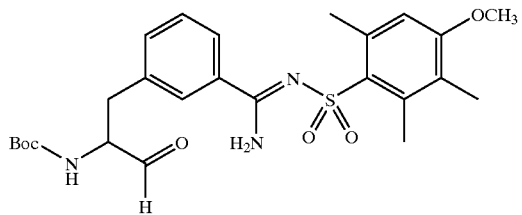

To a stirred solution of LiAlH$_4$ (2.00 mL of a 1.0 M solution in tetrahydrofuran, 1.24 mmol) in tetrahydrofuran (8 mL), cooled in a dry ice/acetone bath, the compound of Example 69 (0.75 g, 1.9 mmol in tetrahydrofuran (5 mL)) was added dropwise. The cooling bath was removed and the reaction mixture was allowed to warm to 5° C. The reaction mixture was re-cooled in the dry ice acetone bath and quenched with 3.0 mL of a 1:2.7 wt./wt. solution of potassium bisulfate in water. The reaction mixture was allowed to warm to room temperature, stirred for 3 hours, filtered and concentrated under vacuum. The residue was dissolved in ethyl acetate (20 mL), and washed with 10% citric acid (2 mL), water (2 mL), saturated sodium bicarbonate (2 mL) and brine (2 mL). The organic layer was dried over anydrous magnesium sulfate and the solvent was removed under vacuum to yield 580 mg (86%) of the title compound. $^1$H NMR (CDCl$_3$): delta 1.31 (s, 9H), 2.07 (s, 3H), 2.57 (s, 3H), 2.67 (s, 3H), 2.90–3.17 (2H, m), 3.77 (s, 3H), 4.33–4.40 (1H, m), 5.02–5.08 (1H, m), 6.48 (1H, s), 7.23–7.31 (2H, m), 7.50–7.62 (2H, m), 7.94, (1H, bs), 8.05 (1H, bs), 9.55 (1H, s). Analysis calculated for $C_{25}H_{33}N_3O_6S \cdot 0.5H_2O$: C, 58.58; H, 6.69; N, 8.20. Found: C, 58.57; H, 6.72; N, 7.98.

Example 71

Preparation of N-α-Boc-N-γ-4-methoxy-2,3,6-trimethylbenzenesulfonyl-D,L-3-amidinophenylalaninal-semicarbazonyl-4-N-diphenylmethane

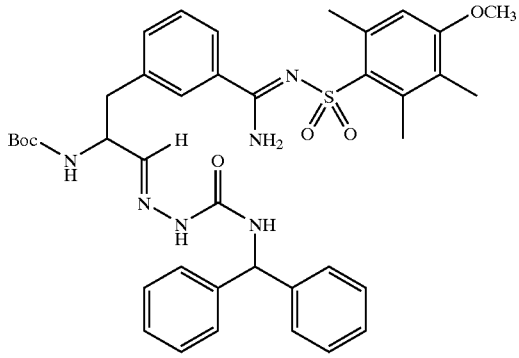

The compound of Example 70 (0.58 g, 1.9 mmol), the compound of Example 65 (410 mg, 1.15 mmol) and sodium acetate trihydrate (188 mg, 1.38 mmol) were refluxed in 75% aqueous ethanol (10 mL) for 1 hour. After the reaction mixture was cooled to room temperature, it was diluted with ethyl acetate (50 mL), washed with 1.0N HCl (5 mL), water (5 mL), saturated sodium bicarbonate (5 mL) and brine (2×5 mL), and dried over anhydrous magnesium sulfate. The solvent was removed under vacuum to yield 750 mg (89% yield) of the title compound as an off-white foam. Analysis calculated for $C_{39}H_{46}N_6O_6S \cdot 1.0\ H_2O$: %C, 62.88; %H, 6.49; %N, 11.28. Found: %C, 63.14; %H, 6.35 %N, 11.10. Calculated molecular weight was 726.90.

Example 72

Preparation of N-omega-4-methoxy-2,3,6-trimethylbenzene sulfonyl-D,L-3-amidinophenylalaninal-semicarbazonyl-4-N-diphenylmethane, Trifluoroacetate Salt

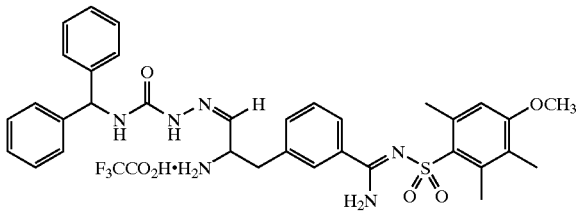

The compound of Example 71 (750 mg, 1.9 mmol) was treated with 50% trifluoroacetic acid/dichloromethane (3 mL) for 30 minutes at room temperature. The reaction mixture was added dropwise to ether (50 mL). The solution was allowed to stand at 4° C. for 18 hours. The product was filtered, and dried under vacuum to yield 600 mg (79% yield) of the title compound as an off-white solid. Analysis calculated for $C_{34}H_{38}N_6O_4S \cdot 1.3CF_3CO_2H$: %C, 56.72; %H, 5.11; %N, 10.84. Found: %C, 56.34; %H, 5.47; %N, 11.49. The salt had a calculated molecular weight of 740.8.

Example 73

Preparation of Compound 10-6

Compound 10-6 of FIG. 10 is prepared according to the method of Examples 60 to 64 with the substitution of t-butoxycarbonyl-4-(4-pyridyl) alanine in Example 60.

Example 74

Preparation of Compound 11-7

Compound 11-7 of FIG. 11 is prepared according to the reaction scheme shown in FIG. 11.

Example 75

Preparation of Compound 12-5

Compound 12-5 of FIG. 12 is prepared according to the reaction scheme shown in FIG. 12.

By following the teachings of the Detailed Description of the Invention and the Examples and using the appropriate starting materials and reagents, the following compounds were made:

N-alpha-(2-phenylethyl)sulfonyl-D-seryl-azetidine-2-carbonyl-argininal;
benzyloxycarbonyl-D-seryl-4-hydroxyprolyl-argininal; and
benzyloxycarbonyl-D-seryl-3-trans-hydroxyprolyl-argininal.

By following the teachings of the Detailed Description of the Invention and the Examples and using the appropriate starting materials and reagents, the following compound is made:

N-alpha-(2-phenylethyl)sulfonyl-D-seryl-3,4-dihydro-prolyl-argininal.

Example A

In Vitro Enzyme Assays for Specificity Determination

The ability of compounds of the present invention to act as selective inhibitors of urokinase catalytic activity was assessed by determining the concentration of test compound which inhibited the activity of this enzyme by 50%, ($IC_{50}$), and comparing this value to that determined for all or some of the following related serine proteases: recombinant tissue plasminogen activator (rt-PA), plasmin, activated protein C, chymotrypsin, factor Xa, thrombin and trypsin.

The buffer used for all assays was HBSA (10 mM HEPES, pH 7.5, 150 mM sodium chloride, 0.1% bovine serum albumin).

The assay for $IC_{50}$ determinations was conducted by combining in appropriate wells of a Corning microtiter plate, 50 microliters of HBSA, 50 microliters of the test compound at a specified concentration (covering a broad concentration range) diluted in HBSA (or HBSA alone for $V_0$ (uninhibited velocity) measurement), and 50 microliters of the enzyme diluted in HBSA. Following a 30 minute incubation at ambient temperature, 50 microliters of the substrate at the concentrations specified below were added to the wells, yielding a final total volume of 200 microliters (about 4 times Km). The initial velocity of chromogenic substrate hydrolysis was measured by the change in absorbance at 405 nm using a Thermo Max® Kinetic Microplate Reader over a 5 minute period in which less than 5% of the added substrate was utilized. The concentration of added inhibitor which caused a 50% decrease in the initial rate of hydrolysis was defined as the $IC_{50}$ value.

Urokinase Assay

Urokinase catalytic activity was determined using the chromogenic substrate 150 mM S-2444 (L-Pyroglutamyl-glycyl-L-arginine-p-nitroanilide hydrochloride), obtained from DiaPharma Group, Inc. Urokinase (Abbokinase), manufactured by Abbott Laboratories, was obtained from Priority Pharmaceuticals and diluted to 750 pM in the HBSA assay buffer prior to use. The assay buffer was HBS (10 mM HEPES, 150 mM sodium chloride pH 7.4) with 0.1% BSA.

Thrombin (fIIa) Assay

Enzyme activity was determined using the chromogenic substrate, Pefachrome t-PA ($CH_3SO_2$-D-hexahydrotyrosine-glycyl-L-Arginine-p-nitroanilide, obtained from Pentapharm Ltd.). The substrate was reconstituted in deionized water prior to use. Purified human α-thrombin was obtained from Enzyme Research Laboratories, Inc. The buffer used for all assays was HBSA (10 mM HEPES, pH 7.5, 150 mM sodium chloride, 0.1% bovine serum albumin).

$IC_{50}$ determinations were conducted where HBSA (50 μL), α-thrombin (50 μl) (the final enzyme concentration is 0.5 nM) and inhibitor (50 μl) (covering a broad concentration range), were combined in appropriate wells and incubated for 30 minutes at room temperature prior to the addition of substrate Pefachrome-t-PA (50 μl) (the final substrate concentration is 250 μM, about 5 times Km). The initial velocity of Pefachrome t-PA hydrolysis was measured by the change in absorbance at 405 nm using a Thermo Max® Kinetic Microplate Reader over a 5 minute period in which less than 5% of the added substrate was utilized. The concentration of added inhibitor which caused a 50% decrease in the initial rate of hydrolysis was defined as the $IC_{50}$ value.

Factor Xa

Factor Xa catalytic activity was determined using the chromogenic substrate S-2765 (N-benzyloxycarbonyl-D-arginine-L-glycine-L-arginine-p-nitroaniline), obtained from DiaPharma Group (Franklin, Ohio). All substrates were reconstituted in deionized water prior to use. The final concentration of S-2765 was 250 μM (about 5-times Km). Purified human Factor X was obtained from Enzyme Research Laboratories, Inc. (South Bend, Ind.) and Factor Xa (FXa) was activated and prepared from it as described [Bock, P. E., Craig, P. A., Olson, S. T., and Singh, P. Arch. Biochem. Biophys. 273:375–388 (1989)]. The enzyme was diluted into HBSA prior to assay in which the final concentration was 0.25 nM.

Recombinant Tissue Plasminogen Activator (rt-PA) Assay rt-PA catalytic activity was determined using the substrate, Pefachrome t-PA ($CH_3SO_2$-D-hexahydrotyrosine-glycyl-L-arginine-p-nitroanilide, obtained from Pentapharm Ltd.). The substrate was made up in deionized water followed by dilution in HBSA prior to the assay in which the final concentration was 500 micromolar (about 3-times Km). Human rt-PA (Activase®) was obtained from Genentech Inc. The enzyme was reconstituted in deionized water and diluted into HBSA prior to the assay in which the final concentration was 1.0 nM.

Plasmin Assay

Plasmin catalytic activity was determined using the chromogenic substrate, S-2366 [L-pyroglutamyl-L-prolyl-L-arginine-p-nitroaniline hydrochloride], which was obtained from DiaPharma Group. The substrate was made up in deionized water followed by dilution in HBSA prior to the assay in which the final concentration was 300 micromolar (about 2.5-times Km). Purified human plasmin was obtained from Enzyme Research Laboratories, Inc. The enzyme was diluted into HBSA prior to assay in which the final concentration was 1.0 nM.

Activated Protein C (aPC) Assay aPC catalytic activity was determined using the chromogenic substrate, Pefachrome PC (delta-carbobenzyloxy-D-lysine-L-prolyl-L-arginine-p-nitroaniline dihydrochloride), obtained from Pentapharm Ltd.). The substrate was made up in deionized water followed by dilution in HBSA prior to the assay in which the final concentration was 400 micromolar (about 3 times Km). Purified human aPC was obtained from Hematologic Technologies, Inc. The enzyme was diluted into HBSA prior to assay in which the final concentration was 1.0 nM.

Chymotrypsin Assay

Chymotrypsin catalytic activity was determined using the chromogenic substrate, S-2586 (methoxy-succinyl-L-arginine-L-prolyl-L-tyrosyl-p-nitroanilide), which was obtained from DiaPharma Group. The substrate was made up in deionized water followed by dilution in HBSA prior to the assay in which the final concentration was 100 micromolar (about 9-times Km). Purified (3×-crystallized; CDI) bovine pancreatic α-chymotrypsin was obtained from Worthington Biochemical Corp. The enzyme was reconstituted in deionized water and diluted into HBSA prior to assay in which the final concentration was 0.5 nM.

Trypsin Assay

Trypsin catalytic activity was determined using the chromogenic substrate, S-2222 (benzoyl-L-isoleucine-L-glutamic acid-[gamma-methyl ester]-L-arginine-p-nitroanilide), which was obtained from DiaPharma Group. The substrate was made up in deionized water followed by dilution in HBSA prior to the assay in which the final concentration was 250 micromolar (about 4-times Km). Purified (3×-crystallized; TRL3) bovine pancreatic trypsin was obtained from Worthington Biochemical Corp. The enzyme was reconstituted in deionized water and diluted into HBSA prior to assay in which the final concentration was 0.5 nM.

Table I

Table I lists the determined $IC_{50}$ values for certain of the enzymes listed above for compounds of the present invention that demonstrate a high degree of specificity for the inhibition of urokinase compared to other serine proteases.

TABLE I

| Compound No. | Example No. | uPA* | tPA* | plasmin* |
|---|---|---|---|---|
| 1 | 8 | A | D | C |
|  | 35–40 |  |  |  |
|  | 54–59 |  |  |  |
| 2 | 9 | A | C | C |
| 3 | 10 | A | D | NT |
| 4 | 10 | A | D | NT |
| 5 | 10 | A | D | NT |
| 6 | 10 | A | D | NT |
| 7 | 10 | A | D | NT |
| 8 | 10 | A | D | NT |
| 9 | 10 | A | D | NT |
| 10 | 11 | A | D | NT |
| 11 | 12 | A | D | C |
| 12 | 12 | A | D | C |
| 13 | 12 | B | D | NT |
| 14 | 12 | A | D | NT |
| 15 | 12 | B | D | NT |
| 16 | 12 | B | D | NT |
| 17 | 12 | B | D | NT |
| 18 | 12 | C | D | NT |
| 19 | 13 | A | D | C |
| 20 | 13 | B | D | NT |
| 21 | 13 | B | NT | NT |
| 22 | 13 | C | D | NT |
| 23 | 13 | C | D | NT |
| 24 | 14 | B | NT | NT |
| 25 | 14 | B | NT | NT |
| 26 | 15 | B | D | NT |
| 27 | 15 | B | D | A |
| 28 | 17–21 | A | D | C |
| 29 | 22–26 | A | D | C |
| 30 | 27–34 | B | D | C |
| 31 | 46 | A | NT | C |
| 32 | 47–50 | A | D | C |
| 35 | 10 | C | D | D |
| 36 | 10 | A | D | C |
| 37 | 10 | B | D | D |
| 38 | 10 | B | D | D |
| 39 | 10 | C | D | D |
| 40 | 10 | A | D | D |
| 41 | 16 | C | D | C |
| 42 | 16 | B | D | B |
| 43 | 16 | C | D | C |
| 44 | 51 | C | D | C |
| 45 | 52 | B | D | C |
| 46 | 52 | A | D | C |
| 47 | 51 | A | D | C |
| 48 | 51 | A | D | C |
| 49 | 52 | A | D | C |
| 50 | 52 | A | D | B |
| 51 | 52 | A | D | C |
| 52 | 52 | B | D | C |
| 53 | 53 | A | D | C |

*
A = less than 100 nm
B = 100–250 nm
C = 250-2500 nm
D = greater than 2500 nm
NT = Not tested

What is claimed is:

1. A compound of the formula:

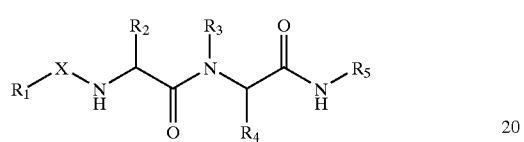

(I)

wherein:

(a) X is selected from the group consisting of —S(O)$_2$—, —N(R')—S(O)$_2$—, —(C=O)—, —OC(=O)—, —NH—C(=O)—, —P(O)(R')—, and a direct link, wherein R' is independently hydrogen, alkyl of 1 to 4 carbon atoms, aryl of 6 to 14 carbon atoms or aralkyl of 7 to 16 carbon atoms, with the proviso that when X is —P(O)(R')—, then R' is not hydrogen;

(b) R$_1$ is selected from the group consisting of:

(1) alkyl of 1 to 12 carbon atoms which is optionally substituted with Y$_1$, (2) alkyl of 1 to 3 carbon atoms substituted with cycloalkyl of 5 to 8 carbon atoms which is optionally mono-, di- or tri-substituted on the ring with Y$_1$, Y$_2$, and/or Y$_3$, (3) cycloalkyl of 3 to 15 carbon atoms, which is optionally mono-, di-, or tri-substituted on the ring with Y$_1$, Y$_2$, and/or Y$_3$, (4) heterocycloalkyl of 4 to 10 ring atoms with the ring atoms selected from carbon and heteroatoms, wherein the heteroatoms are selected from the group consisting of oxygen, nitrogen, and S(O)$_i$, wherein i is 0, 1 or 2, which is optionally mono-, di-, or tri-substituted on the ring with Y$_1$, Y$_2$, and/or Y$_3$, (5) heterocyclo of 4 to 10 ring atoms with the ring atoms selected from carbon and heteroatoms, wherein the heteroatoms are selected from the group consisting of oxygen, nitrogen, and S(O)$_i$, wherein i is 0, 1, or 2, which is optionally mono-, di-, or tri-substituted on the ring carbons with Y$_1$, Y$_2$, and/or Y$_3$, (6) alkenyl of 2 to 6 carbon atoms which is optionally substituted with cycloalkyl of 5 to 8 carbon atoms, which is optionally mono-, di-, or tri-substituted on the ring with Y$_1$, Y$_2$, and/or Y$_3$, (7) aryl of 6 to 14 carbon atoms which is optionally mono-, di- or tri-substituted with Y$_1$, Y$_2$, and/or Y$_3$, (8) heteroaryl of 5 to 14 atoms with the ring atoms selected from carbon and heteroatoms, wherein the heteroatoms are selected from oxygen, nitrogen, and sulfur, and which is optionally mono-, di- or , tri-substituted with Y$_1$, Y$_2$, and/or Y$_3$, (9) aralkyl of 7 to 15 carbon atoms which is optionally mono-, di-, or tri-substituted on the aryl ring with Y$_1$, Y$_2$, and/or Y$_3$,

(10) heteroaralkyl of 6 to 11 atoms with the ring atoms selected from carbon and heteroatoms, wherein the heteroatoms are selected from oxygen, nitrogen, and sulfur, and which is optionally substituted on the alkyl chain with hydroxy or halogen and optionally mono-, di- or tri-substituted on the ring with Y$_1$, Y$_2$, and/or Y$_3$,

(11) aralkenyl of 8 to 15 carbon atoms which is optionally mono-, di-, or tri-substituted on the aryl ring with Y$_1$, Y$_2$, and/or Y$_3$,

(12) heteroaralkenyl of 7 to 12 atoms with the ring atoms selected from carbon and heteroatoms, wherein the heteroatoms are selected from oxygen, nitrogen, and sulfur, and which is optionally mono-, di- or tri-substituted on the ring carbons with Y$_1$, Y$_2$, and/or Y$_3$,

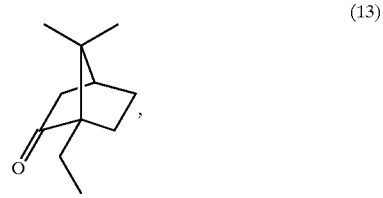

(13)

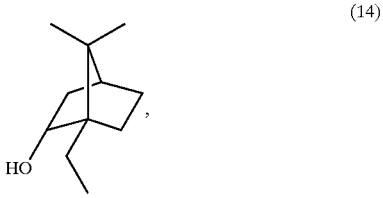

(14)

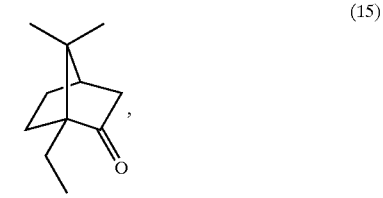

(15)

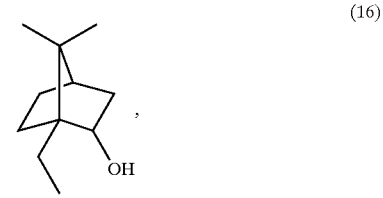

(16)

(17) fused carbocyclic alkyl of 9 to 15 carbon atoms;

(18) difluoromethyl or perfluoroalkyl of 1 to 12 carbon atoms,

(19) perfluoroaryl of 6 to 14 carbon atoms,

(20) perfluoroaralkyl of 7 to 15 carbon atoms, and
(21) hydrogen when X is a direct link; wherein each $Y_1$, $Y_2$, and $Y_3$ is independently selected and is
  (i) selected from the group consisting of halogen, cyano, nitro, tetrazolyl, guanidino, amidino, methylguanidino, —$CF_3$, —$CF_2CF_3$, —$CH(CF_3)_2$, —$C(OH)(CF_3)_2$, —$OCF_3$, —$OCF_2H$, —$OCF_2CF_3$, —$OC(O)NH_2$, —$OC(O)NHZ_1$, —$OC(O)NZ_1Z_2$, —$NHC(O)Z_1$, —$NHC(O)NH_2$, —$NHC(O)NZ_1$, —$NHC(O)NZ_1Z_2$, —$C(O)OH$, —$C(O)OZ_1$, —$C(O)NH_2$, —$C(O)NHZ_1$, —$C(O)NZ_1Z_2$, —$P(O)_3H_2$, —$P(O)_3(Z_1)_2$, —$S(O)_3H$, —$S(O)_mZ_1$, —$Z_1$, —$OZ_1$, —OH, —$NH_2$, —$NHZ_1$, —$NZ_1Z_2$, —N-morpholino, —$S(CF_2)_qCF_3$, and —$S(O)_m(CF_2)_qCF_3$, wherein m is 0, 1 or 2, q is an integer from 0 to 5, and $Z_1$ and $Z_2$ are independently selected from the group consisting of alkyl of 1 to 12 carbon atoms, aryl of 6 to 14 carbon atoms, heteroaryl of 5 to 14 atoms having 1 to 9 carbon atoms, aralkyl of 7 to 15 carbon atoms, and heteroaralkyl of 6 to 11 atoms having 3 to 9 carbon atoms, or
  (ii) $Y_1$ and $Y_2$ are selected together to be —O[C($Z_3$)($Z_4$)]$_r$O—, wherein r is an integer from 1 to 4 and $Z_3$ and $Z_4$ are independently selected from the group consisting of hydrogen, alkyl of 1 to 12 carbon atoms, aryl of 6 to 14 carbon atoms, heteroaryl of 5 to 14 atoms having 1 to 9 carbon atoms, aralkyl of 7 to 15 carbon atoms, and heteroaralkyl of 5 to 14 atoms having 3 to 9 carbon atoms;
(c) $R_2$ is selected from the group consisting of H, —CH($R_6$)OH, and —$CH_2$NH—X'—$R_6$ wherein X' is selected from the group consisting of —(C=O)—, and —C(=O)—O—, and wherein $R_6$ is selected from the group consisting of hydrogen, methyl, 2-phenylethyl and benzyl;
(d) $R_3$ is selected from H or methyl, or $R_3$ and $R_4$ are selected together as set forth in (f),
(e) the carbon bearing $R_4$ is of the S configuration and $R_4$ is selected from the group consisting of H, —$CH_2$—S—$CH_3$, —$CH_{2OH}$, —$CH_2$CN, lower alkyl of 1 to 3 carbon atoms, —$CH_2$C≡CH, —$CH_2$CH=$CH_2$ and —CH=$CH_2$ or $R_3$ and $R_4$ are selected together as set forth in (f);
(f) the carbon bearing $R_4$ is of the S configuration and $R_3$ and $R_4$ are selected together to give a group at P2 selected from the group consisting of prolyl, pipecolyl, azetidine-2-carbonyl, 4-hydroxyprolyl, 3-hydroxyprolyl, and 3,4-dehydroprolyl;
(g) $R_5$ is selected from the group consisting of

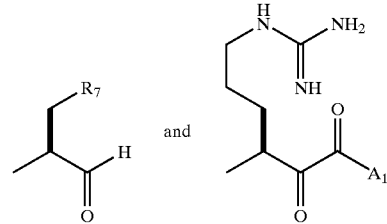

wherein $R_7$ is selected from

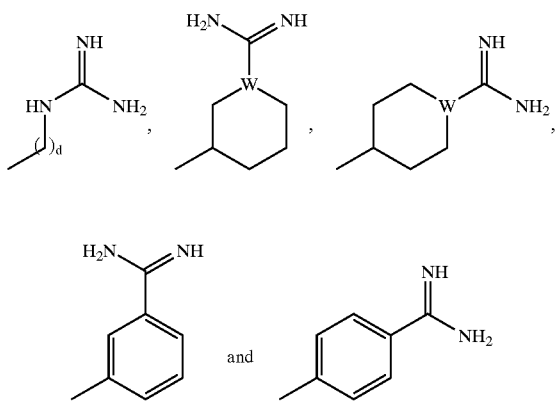

wherein d is an integer from 1 to 3 and W is —N— or —CH—; and
(h) $A_1$ is —$NHR_8$, wherein $R_8$ is alkyl of 1 to 12 carbon atoms, aryl of 6 to 14 carbon atoms or aralkyl of 6 to 15 carbon atoms, all optionally mono-, di or tri-substituted with $Y_1$, $Y_2$ and/or $Y_3$ or is hydrogen; and pharmaceutically acceptable salts thereof with the proviso that when $R_5$ is

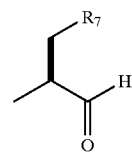

where $R_7$ is —$(CH_2)_2$NHC(=NH)$NH_2$, then $R_1$ is not hydrogen.

2. A compound according to claim 1 wherein $R_5$ is:

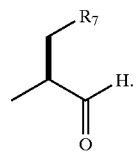

3. A compound according to claim 2 wherein $R_7$ is:

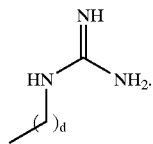

4. A compound according to claim 3 wherein d is 2.

5. A compound according to claim 4 wherein $R_2$ is H or —CH($R_6$)OH where $R_6$ is H or $CH_3$.

6. A compound according to claim 5 wherein $R_2$ is —CH($CH_3$)OH and wherein both the carbon bearing the $R_2$ group (alpha carbon) and $R_6$ (beta carbon) have the R configuration.

7. A compound according to claim 5 wherein $R_3$ is hydrogen.

8. A compound according to claim 7 wherein $R_4$ is methyl or propargyl.

9. A compound according to claim 5 wherein $R_3$ and $R_4$ are selected together to give a group at $P_2$ selected from the group consisting of prolyl, pipecolyl, azetidine-2-carbonyl, 4-hydroxyprolyl, 3-hydroxyprolyl and 3,4-dehydroprolyl.

10. A compound according to claim 9 wherein $R_3$ and $R_4$ are selected together to give a group at $P_2$ selected from the group consisting of prolyl, 4-cis-hydroxyprolyl, 3,4-dehydroprolyl and azetidine-2-carbonyl.

11. A compound according to claim 5 wherein $R_6$ is H.

12. A compound according to claim 5 wherein $R_2$ is —$CH_2OH$ and has the R configuration.

13. A compound according to claim 1 wherein X is selected from —$S(O)_2$—, —$OC(=O)$—, —$NH$—$C(=O)$— and a direct link.

14. A compound according to claim 13 wherein X is —$S(O)_2$— or —$OC(=O)$—.

15. A compound according to claim 14 wherein $R_1$ is selected from phenyl, benzyl, 2-phenylethyl, isobutyl and 3-phenylpropyl.

16. A compound according to claim 15 wherein $R_1$—X— is selected from phenyl-$S(O)_2$—, benzyl-$S(O)_2$—, 2-phenylethyl-$S(O)_2$—, 3-phenylpropyl-$S$—$(O)_2$—, benzyl-$OC(=O)$— and isobutyl-$OC(=O)$—.

17. A compound according to claim 16 wherein $R_2$ is selected to give a group at P3 selected from glycyl, D-seryl, (R,R)D-allothreonyl, D-2-aminobutyryl, N-β-methyloxycarbonyl-D-2,3-N-β-(2-phenylethylcarbonyl)-D-2,3-diaminopropionyl, and N-β-benzyloxycarbonyl-D-2,3-diaminopropionyl.

18. A compound according to 17 wherein the group at P3 is D-seryl or (R,R)D-allothreonyl.

19. A compound according to claim 1 wherein $R_3$ is hydrogen.

20. A compound according to claim 1 wherein $R_4$ is methyl or propargyl.

21. A compound according to claim 1 wherein $R_3$ and $R_4$ are selected together to give a group at P2 selected from the group consisting of prolyl, pipecolyl, azetidine-2-carbonyl, 4-hydroxyprolyl, 3-hydroxyprolyl and 3,4-dehydroprolyl.

22. A compound according to claim 21 wherein $R_3$ and $R_4$ are selected together to give a group at P2 selected from prolyl, 4-cis-hydroxyprolyl, 3,4-dehydroprolyl and azetidine-2-carbonyl.

23. A compound according to claim 1 wherein $R_2$ is selected to give a group at P3 selected from D-seryl and (R,R)D-allothreonyl, and $R_5$ is selected to give an arginine aldehyde at P1.

24. A compound according to claim 23 wherein $R_3$ is hydrogen and $R_4$ is methyl.

25. A compound according to claim 24 wherein $R_3$ and $R_4$ are selected together to give a group at P2 selected from prolyl, azetidine-2-carbonyl and 3,4-dehydroprolyl.

26. A compound according to claim 1 wherein R is

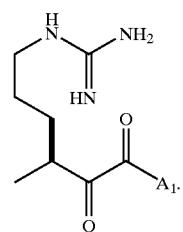

27. A compound according to claim 2 wherein X is selected from —$S(O)_2$—, —$N(R')$—$S(O)_2$— and —$P(O)(R')$—.

28. The compound according to claim 27 of the formula:

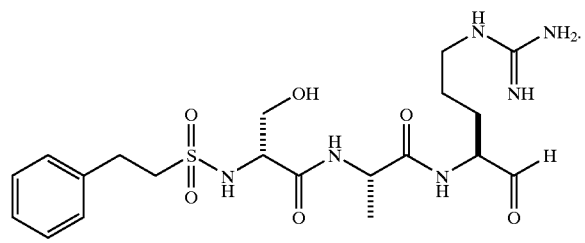

29. A compound according to claim 1 selected from the group consisting of

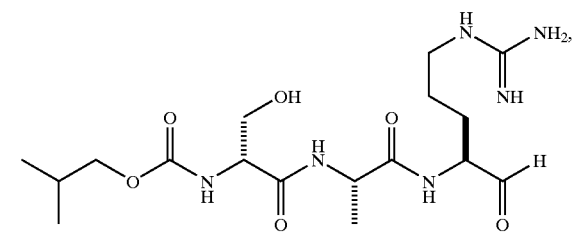

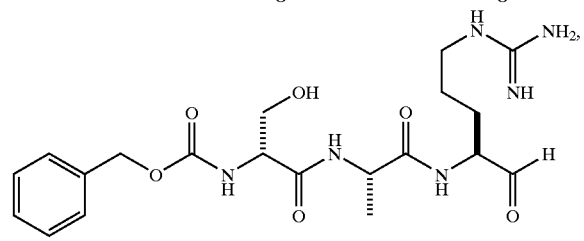

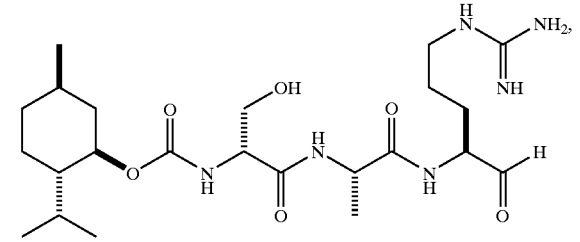

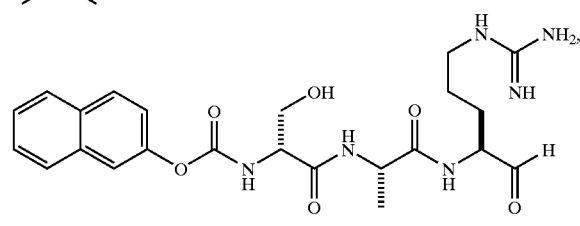

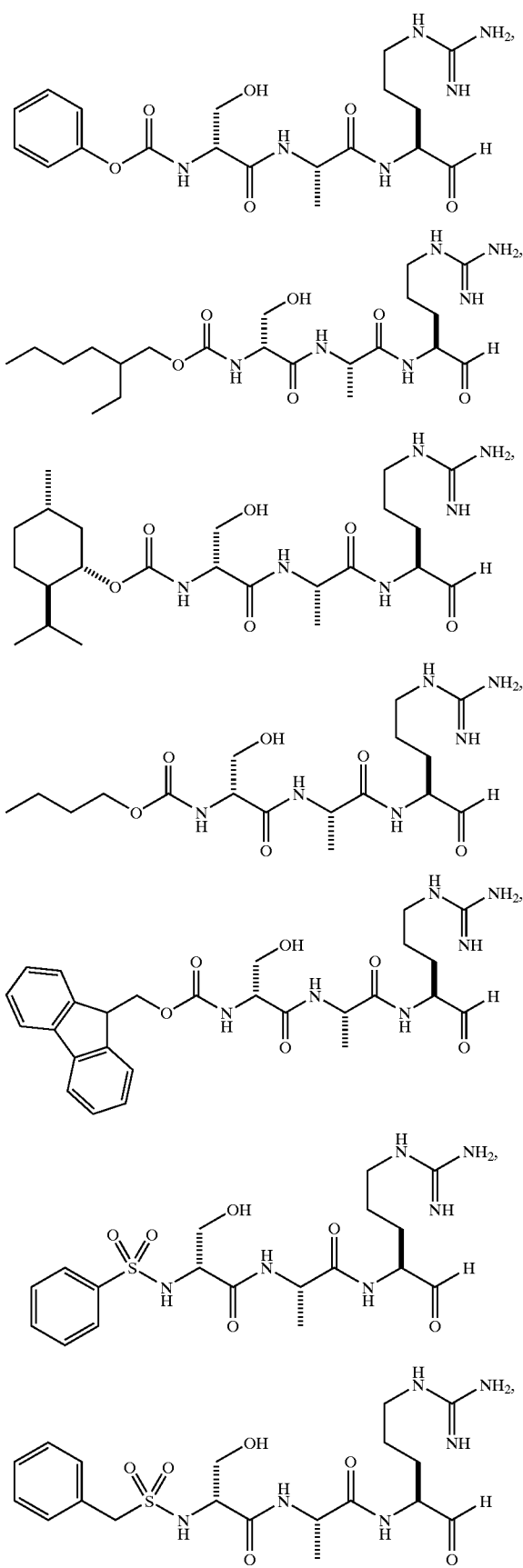

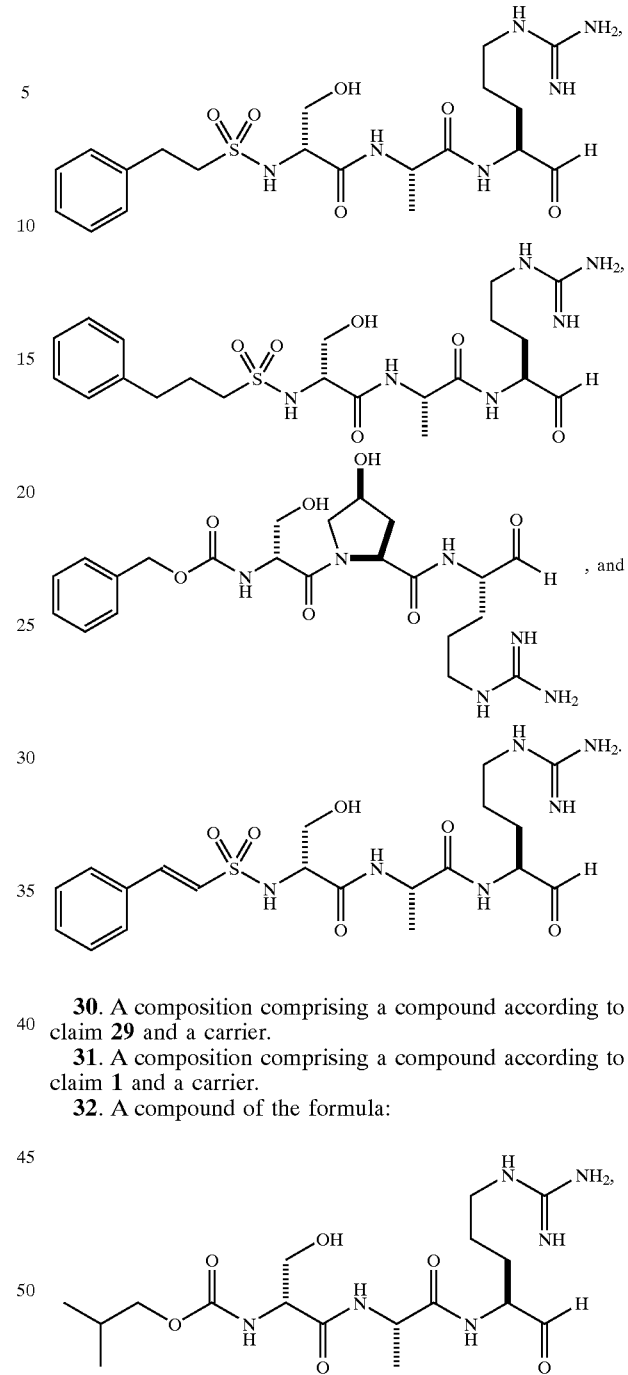

30. A composition comprising a compound according to claim 29 and a carrier.

31. A composition comprising a compound according to claim 1 and a carrier.

32. A compound of the formula:

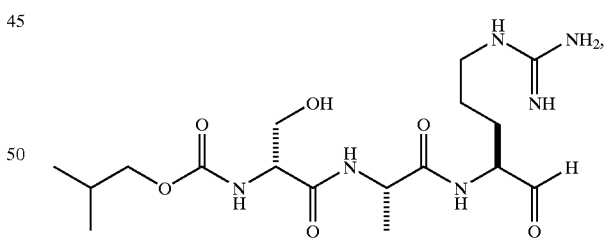

or a pharmaceutically acceptable salt thereof.

33. A composition comprising a compound according to claim 32 and a carrier.

34. A method of inhibiting angiogenesis comprising administering to a mammal in need thereof a compound according to claim 1 for a time and under conditions effective to inhibit urokinase.

35. A method of inhibiting growth of tumor cells comprising administering to a mammal in need thereof a compound according to claim 1 for a time and under conditions effective to inhibit urokinase.

36. A method of inhibiting growth of tumor cells comprising administering to a mammal in need thereof a compound according to claim 4 for a time and under conditions effective to inhibit uorkinase.

37. A method of inhibiting angiogenesis comprising administering to a mammal in need thereof a compound according to claim 4 for a time and under conditions effective to inhibit urokinase.

38. A method of inhibiting urokinase comprising administering to a mammal in need thereof a compound according to claim 4 for a time and under conditions effective to inhibit urokinase.

39. A method of inhibiting urokinase comprising administering to a mammal in need thereof a compound according to claim 10 for a time and under conditions effective to inhibit urokinase.

40. A method of inhibiting angiogenesis comprising administering to a mammal in need thereof a compound according to claim 10 for a time and under conditions effective to inhibit urokinase.

41. A method of inhibiting growth of tumor cells comprising administering to a mammal in need thereof a compound according to claim 10 for a time and under conditions effective to inhibit urokinase.

42. A method of inhibiting angiogenesis comprising administering to a mammal in need thereof a compound according to claim 16 for a time and under conditions effective to inhibit urokinase.

43. A method of inhibiting growth of tumor cells comprising administering to a mammal in need thereof a compound according to claim 16 for a time and under conditions effective to inhibit urokinase.

44. A method of inhibiting urokinase comprising administering to a mammal in need thereof a compound according to claim 16 for a time and under conditions effective to inhibit urokinase.

45. A method of inhibiting urokinase comprising administering to a mammal in need thereof a compound according to claim 23 for a time and under conditions effective to inhibit urokinase.

46. A method of inhibiting angiogenesis comprising administering to a mammal in need thereof a compound according to claim 23 for a time and under conditions effective to inhibit urokinase.

47. A method of inhibiting growth of tumor cells comprising administering to a mammal in need thereof a compound according to claim 23 for a time and under conditions effective to inhibit urokinase.

48. A method of inhibiting urokinase comprising administering to a mammal in need thereof a compound according to claim 1 for a time and under conditions effective to inhibit urokinase.

49. A method of inhibiting urokinase comprising administering to a mammal in need thereof a compound according to claim 18 for a time and under conditions effective to inhibit urokinase.

50. A method of inhibiting growth of tumor cells comprising administering to a mammal in need thereof a compound according to claim 18 for a time and under conditions effective to inhibit urokinase.

51. A method of inhibiting angiogenesis comprising administering to a mammal in need thereof a compound according to claim 18 for a time and under conditions effective to inhibit urokinase.

52. A method of inhibiting urokinase comprising administering to a mammal in need thereof a compound according to claim 29 for a time and under conditions effective to inhibit urokinase.

53. A method of inhibiting angiogenesis comprising administering to a mammal in need thereof a compound according to claim 29 for a time and under conditions effective to inhibit urokinase.

54. A method of inhibiting growth of tumor cells comprising administering to a mammal in need thereof a compound according to claim 29 for a time and under conditions effective to inhibit urokinase.

* * * * *

SEQUENCE LISTING

<160> NUMBER OF SEQ ID NOS: 2

<210> SEQ ID NO 1
<211> LENGTH: 5
<212> TYPE: PRT
<213> ORGANISM: Homo sapiens

<400> SEQUENCE: 1

Ser Ala Arg Met Ala
1               5

<210> SEQ ID NO 2
<211> LENGTH: 5

```
<212> TYPE: PRT
<213> ORGANISM: Homo sapiens

<400> SEQUENCE: 2

Thr Gly Arg Thr Gly
1               5
```